United States Patent
Zhang et al.

(10) Patent No.: US 12,297,453 B2
(45) Date of Patent: May 13, 2025

(54) GENERATION OF NOREPINEPHRINE NEURONS FROM HUMAN STEM CELLS

(71) Applicant: Wisconsin Alumni Research Foundation, Madison, WI (US)

(72) Inventors: Su-Chun Zhang, Waunakee, WI (US); Yunlong Tao, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 241 days.

(21) Appl. No.: 17/563,844

(22) Filed: Dec. 28, 2021

(65) Prior Publication Data
US 2022/0204925 A1 Jun. 30, 2022

Related U.S. Application Data

(60) Provisional application No. 63/133,180, filed on Dec. 31, 2020.

(51) Int. Cl.
*C12N 5/0793* (2010.01)
*G01N 33/50* (2006.01)

(52) U.S. Cl.
CPC ....... *C12N 5/0619* (2013.01); *G01N 33/5058* (2013.01); *C12N 2500/32* (2013.01); *C12N 2500/38* (2013.01); *C12N 2501/13* (2013.01); *C12N 2501/15* (2013.01); *C12N 2501/16* (2013.01); *C12N 2501/415* (2013.01); *C12N 2501/999* (2013.01); *C12N 2506/02* (2013.01)

(58) Field of Classification Search
CPC .............. C12N 5/0619; C12N 2501/13; C12N 2501/15; C12N 2501/16; C12N 2501/415; C12N 2506/02; C12N 2501/155; G01N 33/5058

See application file for complete search history.

(56) References Cited

FOREIGN PATENT DOCUMENTS

CN 111 484 977 8/2020

OTHER PUBLICATIONS

Calatayud, C., Carola, G., Fernández-Carasa, I. et al. CRISPR/Cas9-mediated generation of a tyrosine hydroxylase reporter iPSC line for live imaging and isolation of dopaminergic neurons. Sci Rep 9, 6811 (Year: 2019).*
Rehman S, Rahimi N, Dimri M. Biochemistry, G Protein Coupled Receptors. [Updated Jul. 30, 2023]. In: StatPearls [Internet]. Treasure Island (FL): StatPearls Publishing (Year: 2023).*
Satoh, Motonobu, Hiromu Sugino, and Touho Yoshida. "Activin promotes astrocytic differentiation of a multipotent neural stem cell line and an astrocyte progenitor cell line from murine central nervous system." Neuroscience letters 284.3 (2000): 143-146. (Year: 2000).*
Suzuki, Kotaro, et al. "Activin A induces neuronal differentiation and survival via ALK4 in a SMAD-independent manner in a subpopulation of human neuroblastomas." Biochemical and biophysical research communications 394.3 (2010): 639-645. (Year: 2010).*
Rodríguez-Martínez G, Molina-Hernández A, Velasco I (2012) Activin A Promotes Neuronal Differentiation of Cerebrocortical Neural Progenitor Cells. PLOS ONE 7(8): e43797 (Year: 2012).*
Mahabadi et al: "In Vitro Differentiation of Neural Stem Cells into Noradrenergic-Like Cells", IJMCM, vol. 4, No. 1 Dec. 17, 2014 (Dec. 17, 2014), XP055914721, (Year: 2014).*
Mong, Jamie, et al. "Transcription factor-induced lineage programming of noradrenaline and motor neurons from embryonic stem cells." Stem Cells 32.3 (2014): 609-622. (Year: 2014).*
Braak H, Del Tredici K. Neuroanatomy and pathology of sporadic Alzheimer's disease. Adv Anat Embryol Cell Biol. 2015;215:1-162. PMID: 25920101. (Year: 2015).*
International Search Report and Written Opinion for PCT/US2021/065381, mailed May 3, 2022.
Boergermann et al. "Dorsomorphin and LDN-193189 inhibit BMP-mediated Smad, p38 and Akt signalling in C2C12 cells." Int. J Biochem. Cell Biol. 42(11):1802-1807, (Nov. 2010).
Chambers et al. "Highly efficient neural conversion of human ES and iPS cells by dual inhibition of SMAD signaling." Nature Biotech 27(3):275-280, (Mar. 2009).
Chalermpalanupap et al. "Targeting norepinephrine in mild cognitive impairment and Alzheimer's disease." Alzheimers Res Ther 5: 21, (Apr. 2013).
Cuny et al. "Structure-activity relationship study of bone morphogenetic protein (BMP) signaling inhibitors." Bioorg. Med Chem. Lett. 18(15):4388-4392, (Aug. 2008).
Cong et al. "Multiplex genome engineering using CRISPR/Cas systems." Science 339(6121):819-823, (Feb. 2013).
Delaville et al. "Noradrenaline and Parkinson's disease." Front Syst Neurosci 5:31, (May 2011).
Dong et al. "Mechanism and consequence of abnormal calcium homeostasis in Rett syndrome astrocytes." Elife 7, doi: 10.7554/eLife.33417, (Mar. 2018).
Feng et al. "A Genetically Encoded Fluorescent Sensor for Rapid and Specific In Vivo Detection of Norepinephrine." Neuron 102(4):745-761, (Mar. 2019).
Fornai et al. "Noradrenaline in Parkinson's Disease: From Disease Progression to Current Therapeutics." Curr Med Chem 14(12): 2330-2334, (Sep. 2007).

(Continued)

*Primary Examiner* — Maria G Leavitt
*Assistant Examiner* — Michael Angelo Riga
(74) *Attorney, Agent, or Firm* — McDonnell Boehnen Hulbert & Berghoff LLP

(57) ABSTRACT

Methods for obtaining populations of norepinephrine (NE) neuronal progenitor cells and creating enriched populations of NE neurons are provided herein. Also provided herein are methods for obtaining genetically modified NE neurons expressing a NE sensor or a TH-reporter, and methods for using NE neurons obtained according to the methods of this disclosure.

8 Claims, 42 Drawing Sheets

Specification includes a Sequence Listing.

(56) References Cited

OTHER PUBLICATIONS

Forno. "Neuropathology of Parkinson's disease." J Neuropathol Exp Neural, 55(3):259-272, (Mar. 1996).
Gannon et al. "Noradrenergic dysfunction in Alzheimer's disease." Front Neurosci 9: 220, (Jun. 2015).
Gesi et al. "The role of the locus coeruleus in the development of Parkinson's disease." Neurosci Biobehav Rev 24(6): 655-668, (Aug. 2000).
Gottesmann. "The involvement of noradrenaline in rapid eye movement sleep mentation." Front Neurol 2: 81, (Dec. 2011).
Haglund et al. "Locus ceruleus degeneration is ubiquitous in Alzheimer's disease: Possible implications for diagnosis and treatment." Neuropathology 26(6): 528-532, (Nov. 2006).
Hirsch et al. "Control of noradrenergic differentiation and Phox2a expression by MASH1 in the central and peripheral hervous system." Development, 125(4):599-608, (Feb. 1998).
Huang et al. "Time-Course Gene Expression Profiling Reveals a Novel Role of Non-Canonical WNT Signaling During Neural Induction." Sci Rep, 6:32600, doi: 10.1038/srep32600, (Sep. 2016).
Jinek et al. "A programmable dual-RNA-guided DNA endonuclease in adaptive bacterial immunity." Science 337 (6096): 816-821, (Aug. 2012).
Kikuchi et al. "Human iPS cell-derived dopaminergic neurons function in a primate Parkinson's disease model." Nature, 548:592-596, (Aug. 2017).
Leanza et al. "Noradrenergic Hypothesis Linking Neurodegeneration-Based Cognitive Decline and Astroglia." Front Mal Neurosci 11: 254, (Jul. 2018).
Lu et al. "Generation of serotonin neurons from human pluripotent stem cells." Nature Biotech 34:89-94, (Jan. 2016).
Marien et al. "Noradrenergic mechanisms in neurodegenerative diseases: a theory." Brain Res Brain Res Rev 45(1): 38-78, (Apr. 2004).
Matthews et al. "Noradrenergic changes, aggressive behavior, and cognition in patients with dementia." Biol Psychiatry 51(5): 407-416, (Mar. 2002).
Mitchell & Weinshenker. "Good night and good luck: norepinephrine in sleep pharmacology." Biochem Pharmacol 79(6): 801-809, (Mar. 2010).
Montoya et al. "The noradrenergic paradox: implications in the management of depression and anxiety." Neuropsychiatr Dis Treat 12: 541-557, (Mar. 2016).
Moret & Briley. "The importance of norepinephrine in depression." Neuropsychiatr Dis Treat 7(Suppl 1): 9-13, (May 2011).
Morin et al. "Defects in sensory and autonomic ganglia and absence of locus coeruleus in mice deficient for the homeobox gene Phox2a." Neuron 18(3):411-423, (Mar. 1997).
Neely et al. "DMHI, a highly selective small molecule BMP inhibitor promotes neurogenesis of hiPSCs: comparison of PAX6 and SOXI expression during neural induction." ACS Chem Neurosci 3(6): 482-491, (Jun. 2012).
Nobuta et al. "Dysregulation of locus coeruleus development in congenital central hypoventilation syndrome." Acta Neuropathol 130(2): 171-183, (May 2015).
Pattyn et al. "Specification of the central noradrenergic phenotype by the homeobox gene Phox2b." Mol Cell Neurosci, 15(3):235-243, (Mar. 2000).
Remy et al. "Depression in Parkinson's disease: loss of dopamine and noradrenaline innervation in the limbic system." Brain 128(Pt 6): 1314-1322, (Jun. 2005).
Robertson et al. "Developmental origins of central norepinephrine neuron diversity." Nat Neurosci, 16(8):1016-1023, (Jul. 2013).
Roux et al. "Progressive noradrenergic deficits in the locus coeruleus of Mecp2 deficient mice." J Neurosci Res 88(7):1500-1509, (May 2010).
Stewart et al. "Comparative RNA-seq Analysis in the Unsequenced Axolotl: The Oncogene Burst Highlights Early Gene Expression in the Blastema." PLoS Comput. Biol. 9(3): e1002936, (Mar. 2013).
Steyer et al. "Scarless Genome Editing of Human Pluripotent Stem Cells via Transient Puromycin Selection." Stem Cell Reports, 10(2): 642-654, (Feb. 2018).
Taneja et al. "Pathophysiology of Locus Ceruleus Neurons in a Mouse Model of Rett Syndrome." J Neurosci 29(39): 12187-12195, (Sep. 2009).
Ulke et al. "Adult attention deficit/hyperactivity disorder is associated with reduced norepinephrine transporter availability in right attention networks: a (S,S)-O-[11C]methylreboxetine positron emission tomography study." Transl Psychiatry 9: 301, (Nov. 2019).
Viemari et al. "Mecp2 deficiency disrupts norepinephrine and respiratory systems in mice." J Neurosci 25(50):11521-11530, (Dec. 2005).
Weinshenker. "Long Road to Ruin: Noradrenergic Dysfunction in Neurodegenerative Disease." Trends Neurosci 41(4): 211-223, (Apr. 2018).
Yu et al. "BMP type I receptor inhibition reduces heterotopic ossification." Nat Med 14:1363-1369, (Nov. 2008).
Ernsberger et al., "The expression of dopamine beta-hydroxylase, tyrosine hydroxylase, and Phox2 transcription factors in sympathetic neurons: evidence for common regulation during noradrenergic induction and diverging regulation later in development," Mech Dev, 92(2):169-77 (2000).
Li et al., "Conversion of Astrocytes and Fibroblasts into Functional Noradrenergic Neurons", Cell Reports, 28(3):682-697.e7 (2019).
Stanke et al., "Interaction of Mash1 and Phox2b in sympathetic neuron development," Mol Cell Neurosci., 25(3):374-82 (2004).
Tao et al., "Neural Subtype Specification from Human Pluripotent Stem Cells," Cell Stem Cell, 19(5):573-586 (2016).
Zhimin Xu et al., "Induced Dopaminergic Neurons: A New Promise for Parkinson's Disease," Redox Biol., 11, 606-612 (2017).

* cited by examiner

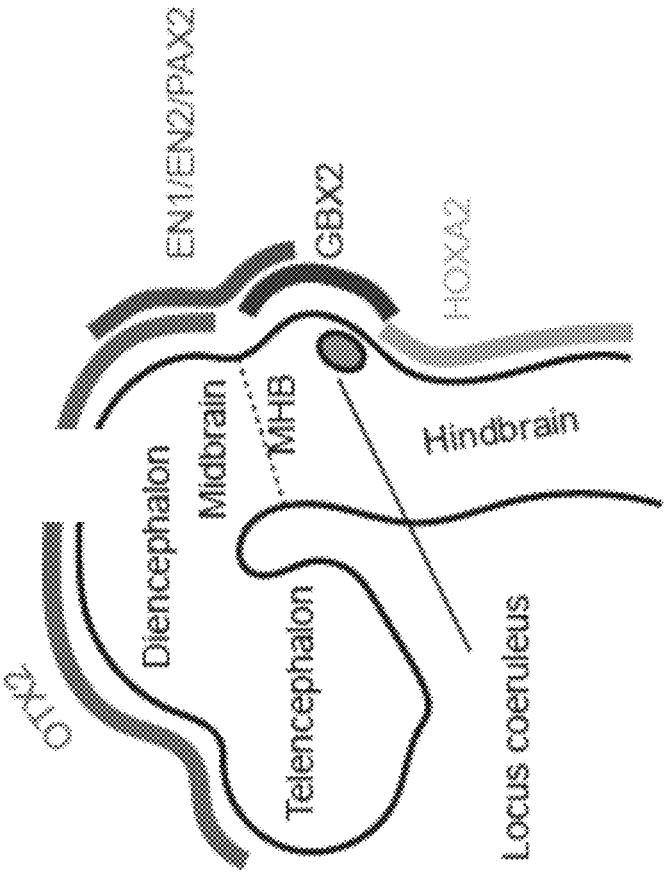
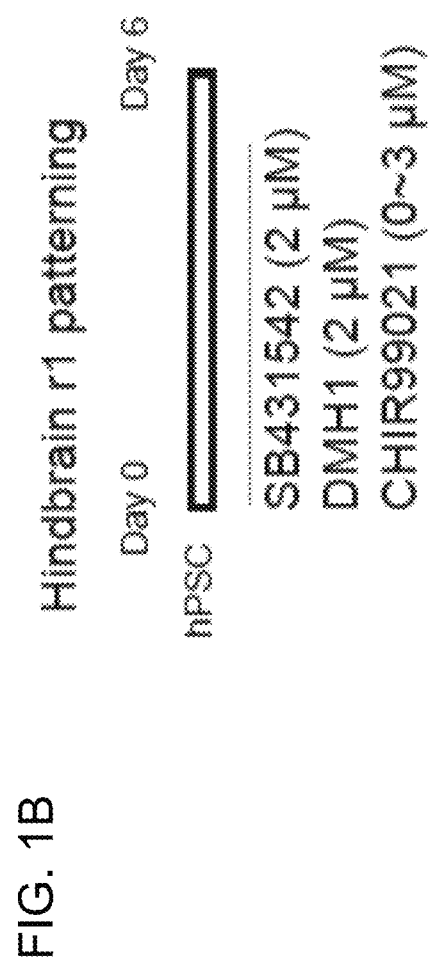
FIG. 1A
FIG. 1B

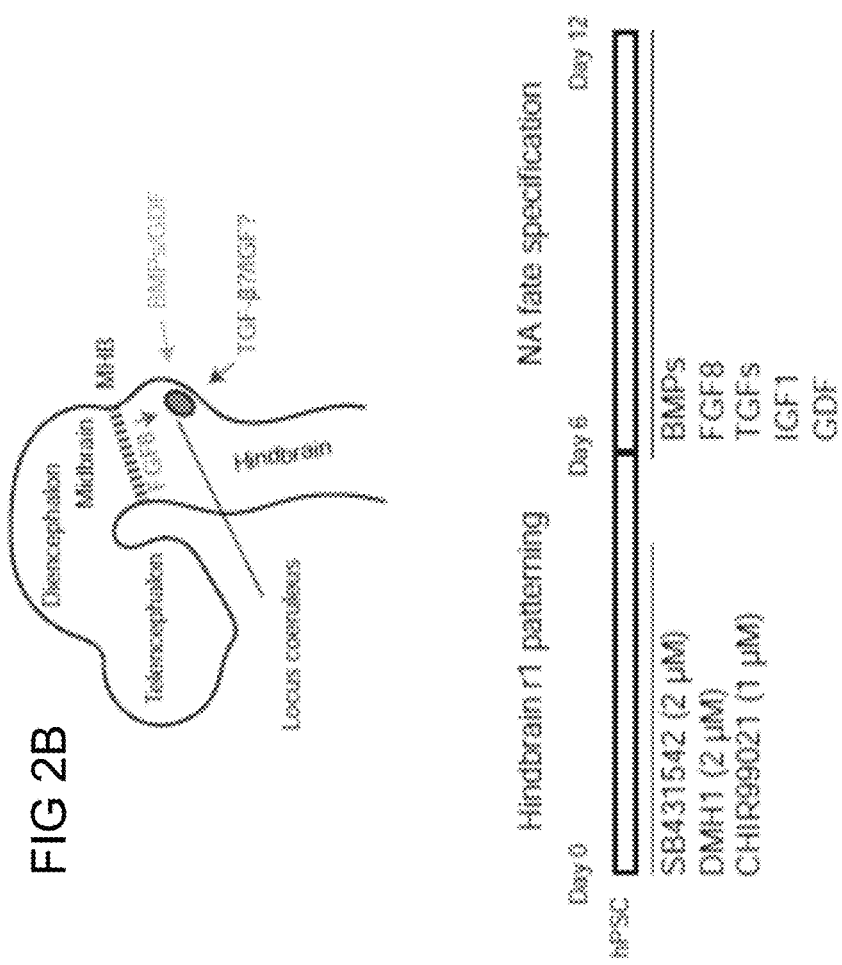
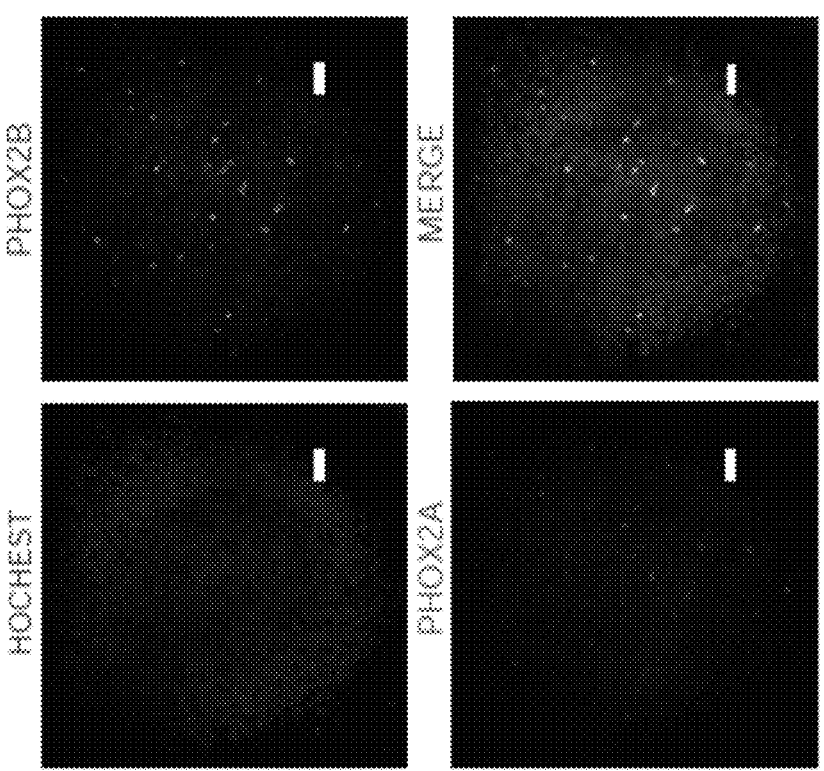
FIG. 2A  FIG 2B  FIG 2C

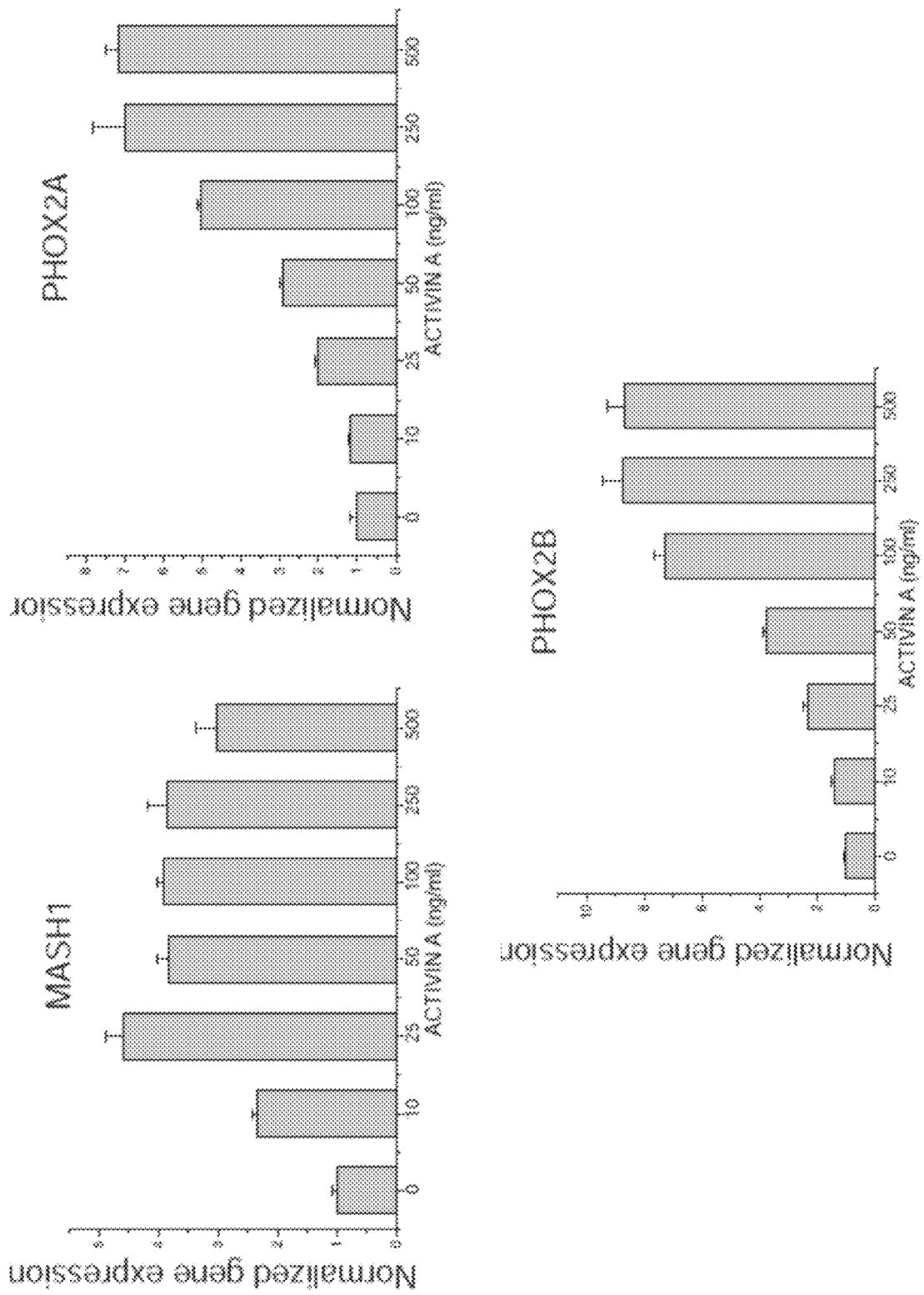

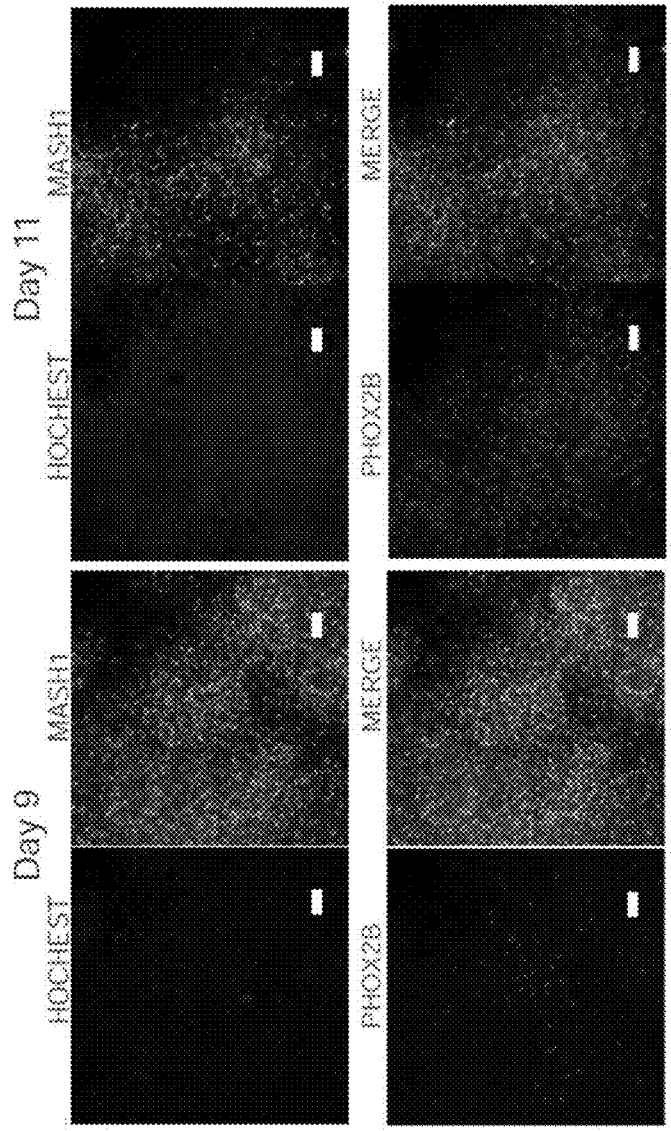
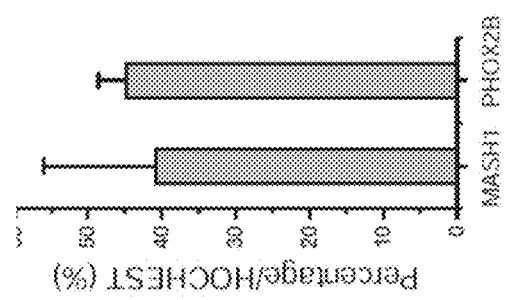
FIG. 3J  FIG. 3K  FIG. 3L

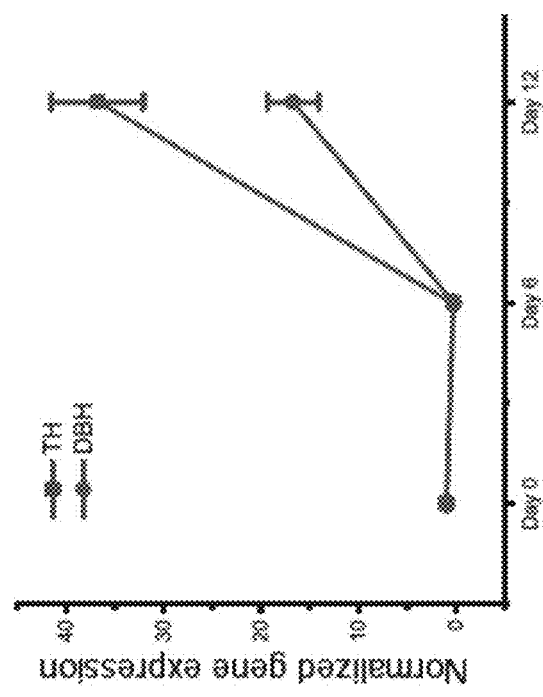
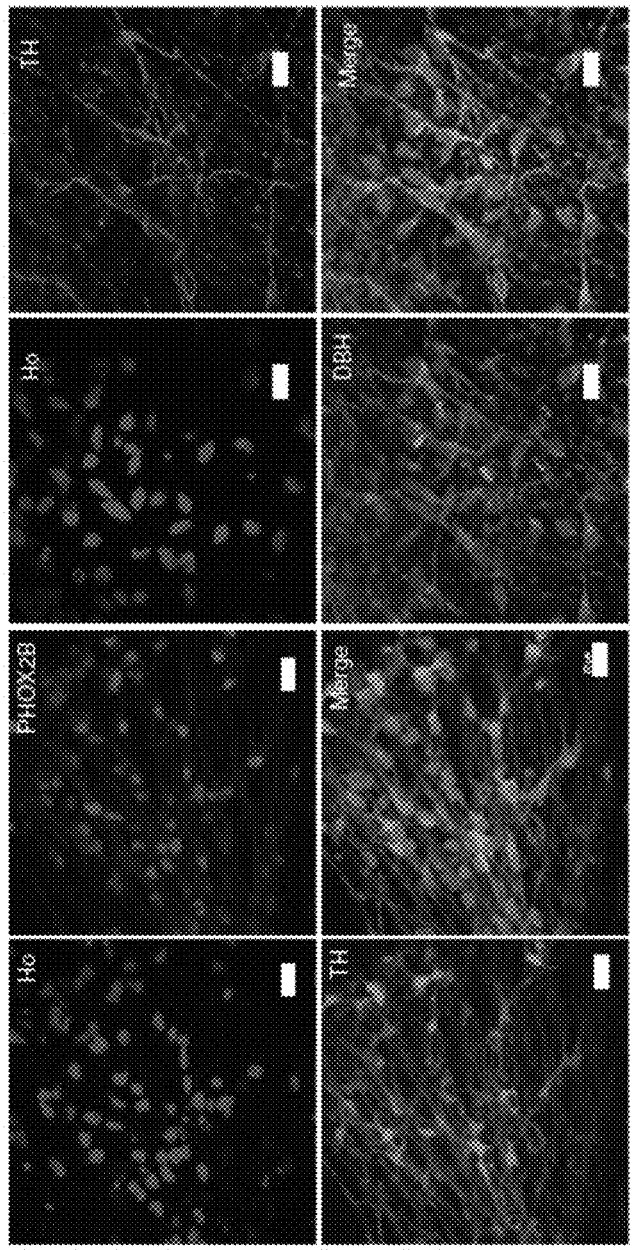
FIG. 4A
FIG. 4B
FIG. 4C

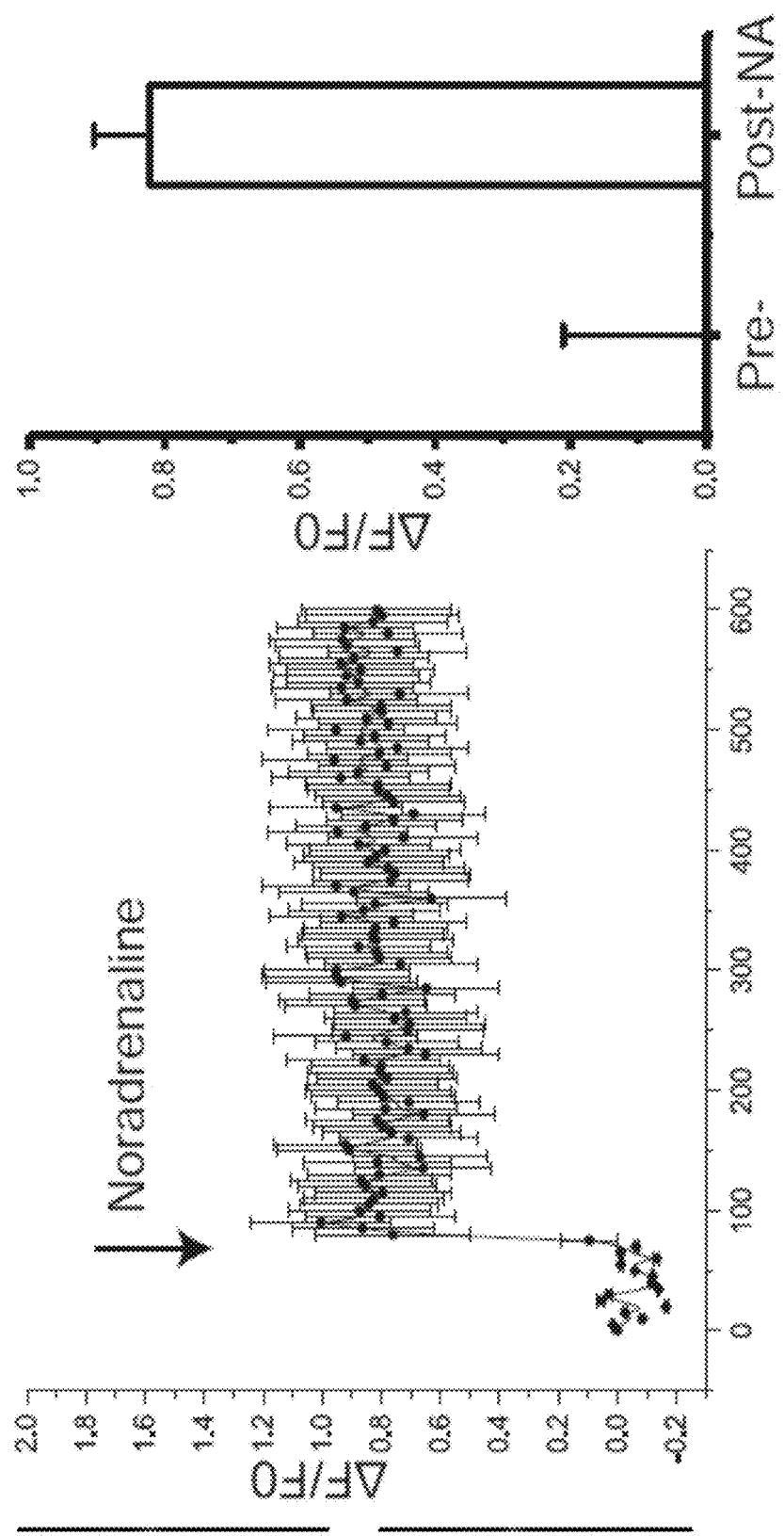

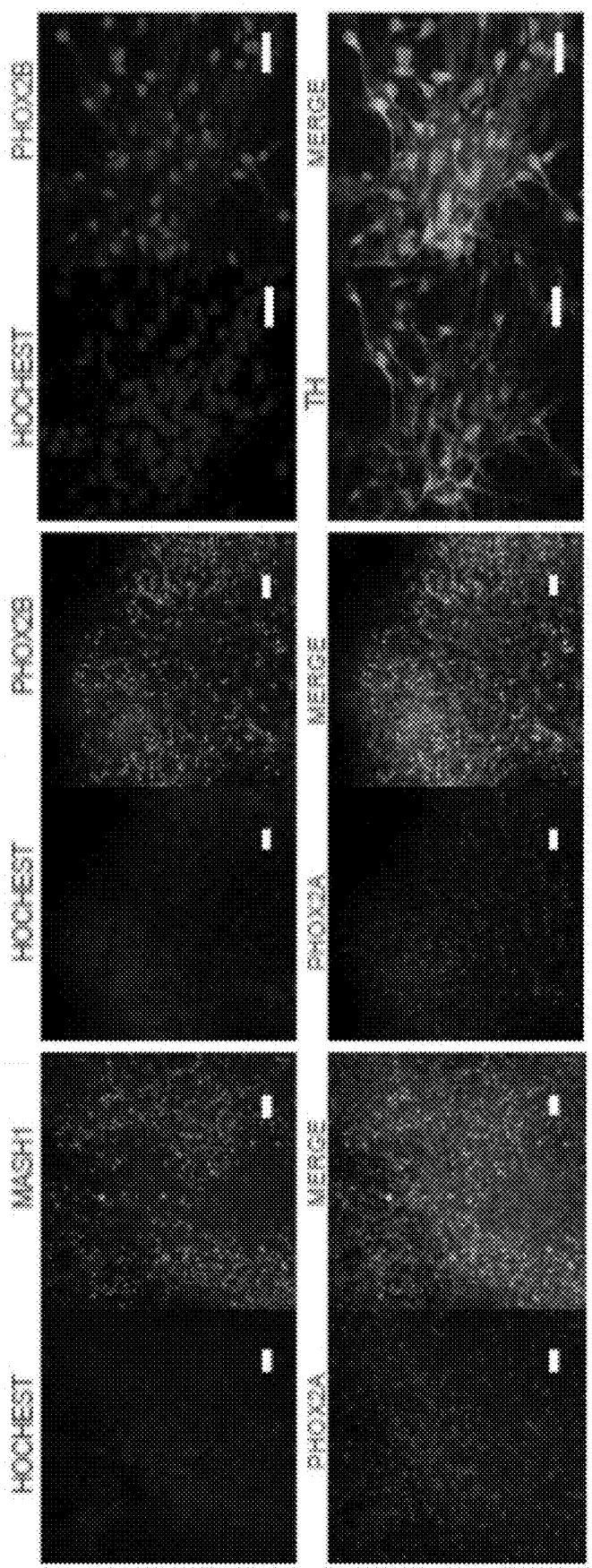

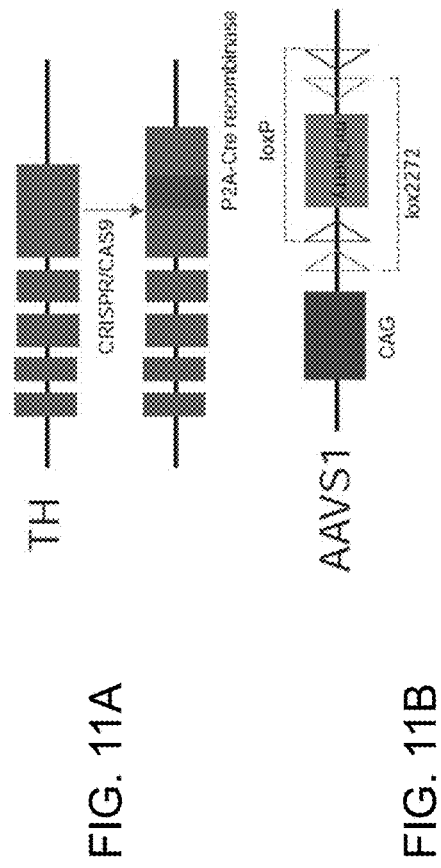
FIG. 11A
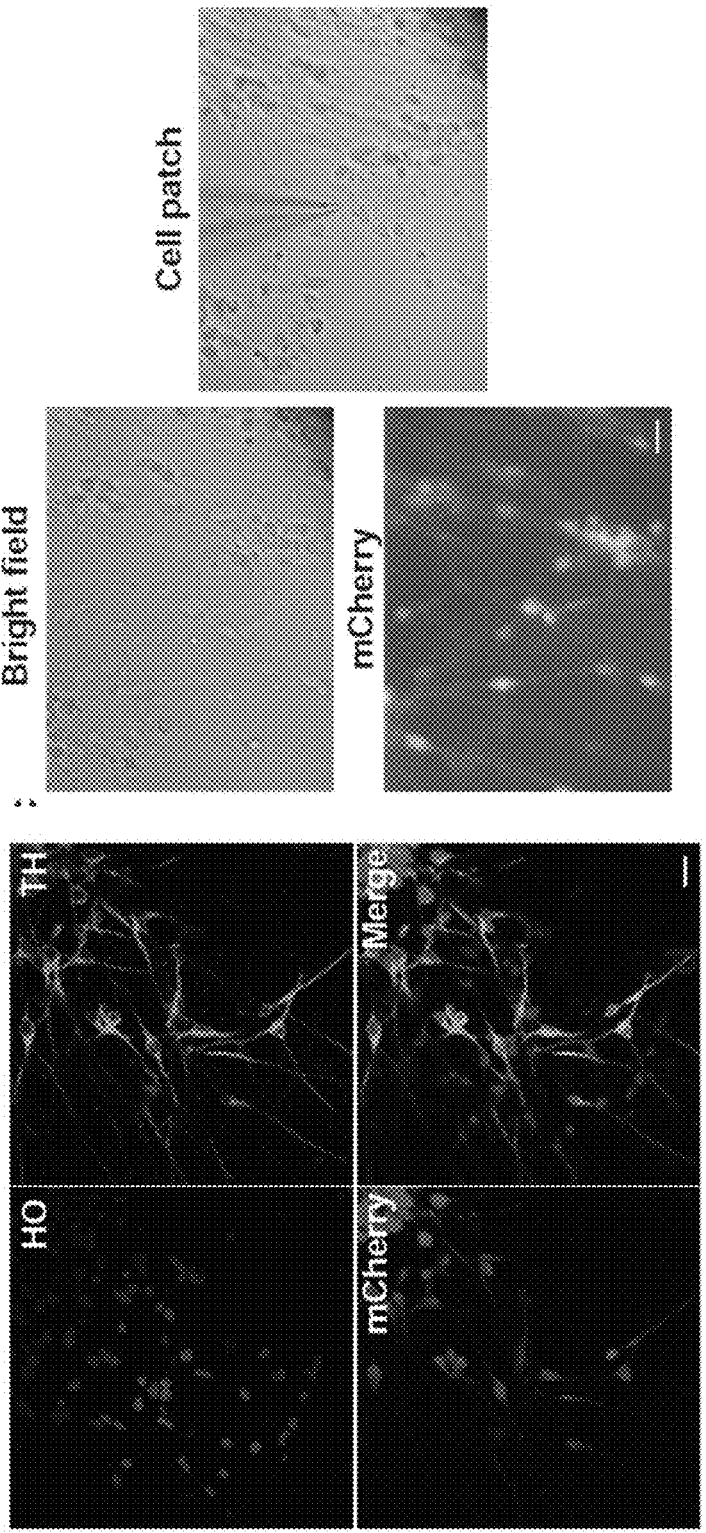
FIG. 11B
FIG. 11C

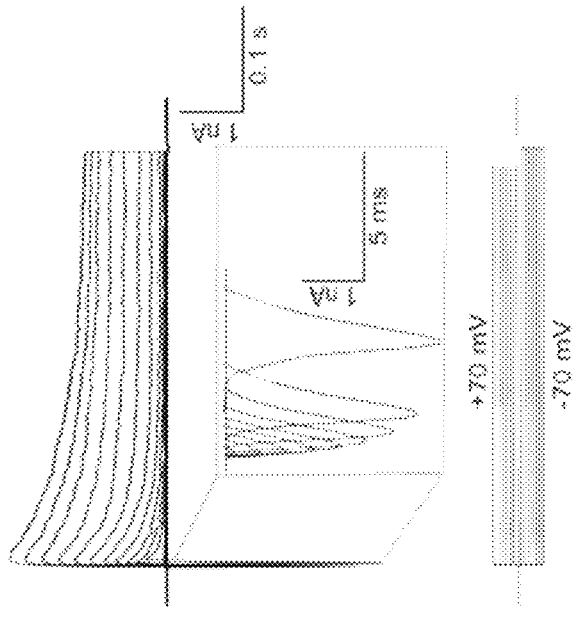
FIG. 11D
FIG. 11E
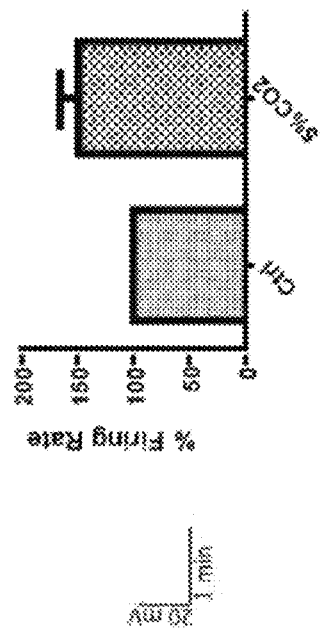
FIG. 11G
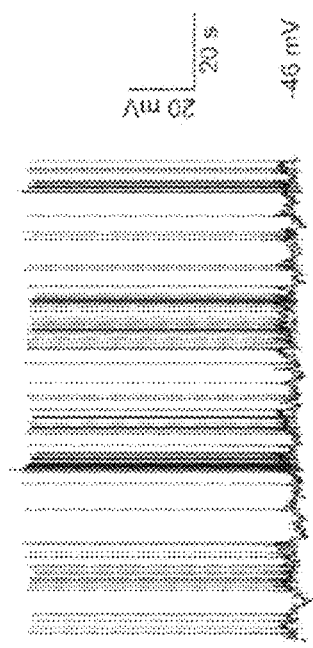
FIG. 11F
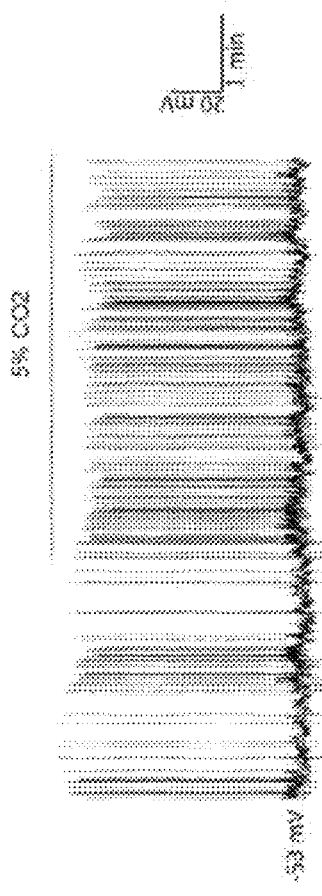

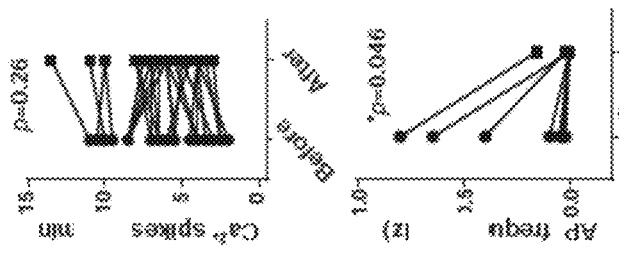
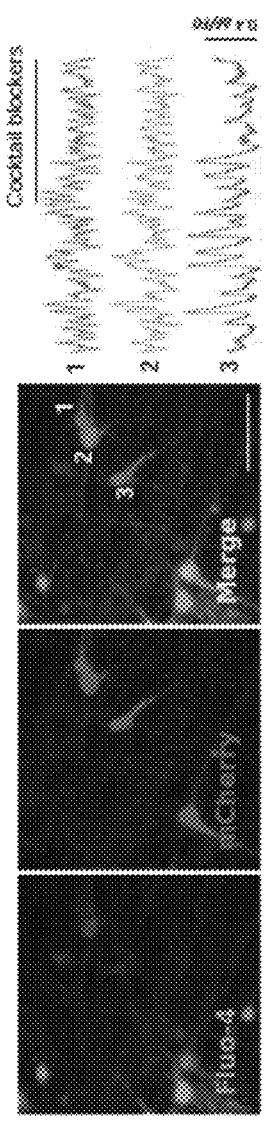
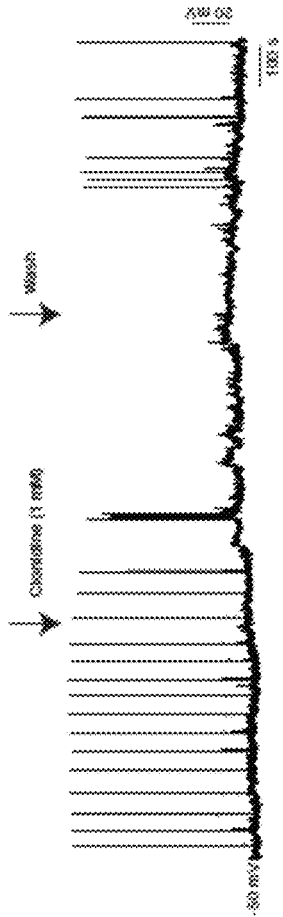
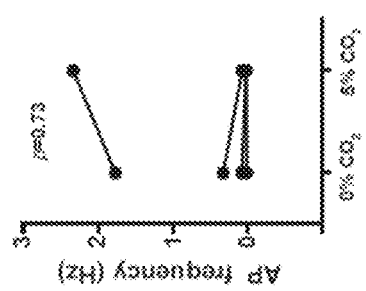
FIG. 11J  FIG. 11K  FIG. 11L  FIG. 11M  FIG. 11N ated on Dec. 30, 2020 and is 606 bytes in size. The Sequence Listing contained in this .txt file is part of the specification and is hereby incorporated by reference herein in its entirety.

GENERATION OF NOREPINEPHRINE NEURONS FROM HUMAN STEM CELLS

CROSS-REFERENCE TO RELATED APPLICATIONS

This application claims the benefit of U.S. Provisional Patent Application No. 63/133,180, filed Dec. 31, 2020, the disclosure of which is explicitly incorporated herein in its entirety by reference.

SEQUENCE LISTING

This application includes an electronically submitted Sequence Listing in .txt format. The .txt file contains a sequence listing entitled "20-1406-PRO_ST25.txt" created on Dec. 30, 2020 and is 606 bytes in size. The Sequence Listing contained in this .txt file is part of the specification and is hereby incorporated by reference herein in its entirety.

STATEMENT REGARDING FEDERALLY FUNDED RESEARCH OR DEVELOPMENT

This invention was made with government support under RD-83573701-0 awarded by the Environmental Protection Agency ("EPA") and under NS082618 awarded by the National Institutes of Health and under 1651645 awarded by the National Science Foundation. The government has certain rights in the invention.

BACKGROUND

Norepinephrine (NE) neurons (also known as noradrenaline (NA) neurons) in the central nervous system (CNS) play essential roles in a wide range of behavioral and physiological processes. NE neurons, mainly located in the locus coeruleus of the hindbrain, project nerves (axons) to virtually all brain regions. NE neurons participate in a wide spectrum of neural functions, including arousal, wakefulness, memory, focus and attention, "fight or flight" reaction, and anxiety. They are also essential for normal heartbeat, blood pressure, and breathing. Dysregulation of the NE system has been linked to Alzheimer's disease (A D; Gannon et al. 2015, Front Neurosci 9: 220; Braak & Del Trecidi, 2015, Adv Anat Embryol Cell Biol 215: 1-162; Matthews et al., 2002, Biol Psychiatry 51: 407-416), Parkinson's disease (P D; Gesi et al., 2000, Neurosci Biobehav Rev 24: 655-668; Remy et al., 2005, Brain 128: 1314-1322; Fornai et al., 2007, Curr Med Chem 14: 2330-2334; Delaville et al., 2011, Front Syst Neurosci 5: 31), Rett syndrome (Viemari et al., 2005, J Neurosci 25: 11521-11530; Taneja et al., 2009, J Neurosci 29: 12187-12195; Roux et al., 2010, J Neurosci Res 88: 1500-1509), congenital central hypoventilation syndrome (CCHS; Nobuta et al., 2015, Acta Neuropathol 130: 171-183), sleep disorders (Mitchell & Weinshenker, 2010, Biochem Pharmacol 79: 801-809; Gottesmann, 2011, Front Neurol 2: 81), ADHD, (Ulke et al., 2019, Transl Psychiatry 9: 301), anxiety, (Montoya et al., 2016, Neuropsychiatr Dis Treat 12: 541-557) and depression (Moret & Briley, 2011, Neuropsychiatr Dis Treat 7: 9-13; Montoya et al., 2016, Neuropsychiatr Dis Treat 12: 541-557). In recent years, it was discovered that NE neuron degeneration in the locus coeruleus represents an early sign in Alzheimer's disease and Parkinson's disease (Marien et al., 2004, Brain Res Brain Res Rev 45: 38-78; Haglund et al., 2006, Neuropathology 26: 528-532). Hence, the health of NE neurons in the hindbrain is not only associated with a large spectrum of psychiatric disorders but also an early predictor for a number of neurodegenerative diseases. Consequently, targeting the NE system is a potential avenue for treating a range of neurological and mental disorders (Chalermpalanupap et al., 2013, Alzheimers Res Ther 5: 21; Leanza et al., 2018, Front Mol Neurosci 11: 254; Weinshenker, 2018, Trends Neurosci 41: 211-223).

While dysregulation of NE systems is responsible for many human disorders, human NE development and its role in the pathophysiology of human diseases are poorly understood owing at least in part to the lack of models mimicking these processes. Studies on disease processes are limited by the available animal models which often do not reflect the nature of disease in human patients. Consequently, current treatments disadvantageously focus primarily on alleviating symptoms through pharmacological and surgical interventions.

Human pluripotent stem cells (hPSCs), including induced pluripotent stem cells (iPSCs) from patients with neurodegenerative diseases, offer a means for providing a cellular model for investigating neurodegenerative disease processes and a source of human NE neurons for regenerative therapy. Unfortunately, generation of NE neurons from hPSCs has not been achieved in the prior art. Moreover, although forced expression of NE determinants Phox2b or Phox2a in neural progenitors can generate NE neurons from mouse embryonic stem cells (mESCs) this stratagem has not been successful in producing NE neurons from hPSCs, suggesting there is an intrinsic difference in NE fate determination between human and mouse. This has hindered large-scale, standardized production of NE neurons from human stem cells for disease modeling, drug development, and cell therapies. Accordingly, there remains a need in the art for large-scale, standardized production of human NE neurons for disease modeling, drug development, and cell therapy-based treatment options that restore NE neurons.

SUMMARY OF THE DISCLOSURE

This invention provides methods for developing large-scale, standardized production of human NE neurons for disease modeling, drug development, and cell therapy-based treatment options that restore NE neurons.

In a first aspect, provided herein are methods for generating human norepinephrine (NE) neuron progenitor cells. The methods comprise culturing human neuroepithelial cells having hindbrain R1 regional identity for about 2 to about 4 days in a first culture medium comprising a first concentration of Activin A; and then additionally culturing these cultured cells for about 3 to about 4 days in a second culture medium comprising a second, higher concentration of Activin A to obtain a cell population comprising greater than about 40% norepinephrine (NE) neuron progenitor cells expressing MASH1+/PHOX2B+/PHOX2A+ and that are negative when assayed for Otx2 expression. The first concentration of Activin A in which human neuroepithelial cells having hindbrain R1 regional identity are cultured can be a concentration of about 10 ng/ml to about 50 ng/ml. The second concentration of Activin A in which said cells are further cultured can be a concentration of about 100 ng/ml to about 250 ng/ml. The first culture medium can comprise DMEM/F-12, N2 supplement, non-essential amino acid (NEAA) supplement, with the first concentration of Activin A. The second culture medium can comprise DMEM/F-12, N2 supplement, B27 supplement, NEAA supplement, and the second concentration of Activin A. Each of the first culture medium and the second culture medium can further comprise an inhibitor of BMP signaling, including but not limited to DMH1 or LDN-193189.

The methods provided herein can further comprise culturing the population comprising human NE neuron progenitor cells for at least 6 days in a neural differentiation medium comprising BDNF, GDNF, TGF-β1, cAMP, and ascorbic acid; and detecting within the cultured cells produced thereby a population of cells positive for tyrosine hydroxylase (TH) and dopamine β-hydroxylase (DBH) expression, whereby a population comprising at least 40% human TH+/DBH+NE neurons is obtained. The neural differentiation medium can comprise about 10 ng/ml BDNF, about 10 ng/ml GDNF, about 1 ng/ml TGF-β1, about 1 ng/ml cAMP, and about 200 μM ascorbic acid. The method can further comprise introducing into the human TH+/DBH+NE neurons a heterologous nucleotide sequence encoding human TH (tyrosine hydroxylase) operably linked to a detectable reporter. The method can further comprise introducing into the human TH+/DBH+NE neurons a heterologous nucleotide sequence encoding a β2 adrenergic G protein-coupled receptor (GPCR) Activation-Based norepinephrine ($GRAB_{NE}$) sensor operably linked to a detectable reporter. The $GRAB_{NE}$ sensor can be stably introduced into the genome of the TH+/DBH+NE neuron. The $GRAB_{NE}$ sensor can be $GRAB_{NE1m}$.

Human neuroepithelial cells having hindbrain R1 regional identity can be obtained according to methods provided herein comprising: culturing human pluripotent stem cells (hPSCs) in a culture medium comprising an inhibitor of BMP signaling, an inhibitor of TGFβ signaling, and a Wnt agonist for about 6 days, whereby a population of neuroepithelial cells having hindbrain R1 regional identity are obtained. The inhibitor of BMP signaling can be DMH1, the inhibitor of TGFβ signaling can be SB431542, and the Wnt agonist can be CHIR99021. The pluripotent stem cells can be human embryonic stem cells or human induced pluripotent stem cells.

In another aspect, provided herein is a substantially pure population of human NE neurons comprising a nucleotide sequence encoding a detectable reporter operably linked to a nucleotide sequence encoding human TH.

In a further aspect, provided herein are methods for testing a compound. The method can comprise contacting a test compound to the substantially pure population of human NE neurons comprising a nucleotide sequence encoding a detectable reporter operably linked to a nucleotide sequence encoding human TH and examining the effect of the compound on the cells. In some embodiments, the effect on the cells include detection of the detectable reporter.

In another aspect, provided herein is a substantially pure population of human NE neurons comprising a heterologous nucleotide sequence encoding a β2 adrenergic G protein-coupled receptor (GPCR) activation-based norepinephrine ($GRAB_{NE}$) sensor.

In another aspect, provided herein are methods for testing a compound wherein the compound is contacted to the substantially pure population of human NE neurons comprising a heterologous nucleotide sequence encoding a β2 adrenergic G protein-coupled receptor (GPCR) activation-based norepinephrine ($GRAB_{NE}$) sensor, and then examining the effect of the compound on the GPCR activation-based norepinephrine ($GRAB_{NE}$) sensor as an indicator of noradrenergic signaling of the contacted human NE neurons.

In a further aspect, provided herein is a substantially pure population of human NE neurons obtained according to a method of this disclosure.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIGS. 1A-1G. (FIG. 1A) Schematic representation of locus coeruleus location during embryonic development and gene markers along forebrain, midbrain and hindbrain. (FIG. 1B) Experimental design to pattern hindbrain R1 region from hPSCs during the first 6 days of neural induction. (FIG. 1C) Regional gene expression under a series of varying CHIR99021 concentrations. (FIG. 1D) Immunostaining for OTX2, EN1 and HOXA2 at day 6 when treated with 1 μM CHIR99021. Scale bars indicate 50 μm. (FIG. 1E) Schematic representation of the distribution of hindbrain R1 markers along dorsal to ventral axis and the location of locus coeruleus origin. (FIG. 1F) Immunostaining for PAX7, SOX1, SOX2 and PAX6 at day 6 from cells treated with 1 μM CHIR99021. (FIG. 1G) Quantification of SOX2, SOX1 and PAX7 expressing cells at day 6 when treated with 1 μM CHIR99021.

FIGS. 2A-2G. (FIG. 2A) Immunostaining for norepinephrine neural progenitor marker PHOX2B and PHOX2A at day 6 from cells treated with 1 μM CHIR99021. (FIG. 2B) Schematic representation of the possible pathways which can affect noradrenaline neural progenitor fate specification. (FIG. 2C) Experimental design to identify factors positively affect the norepinephrine neural progenitor specification. (FIG. 2D) Quantitative PCR (qPCR) of norepinephrine neural progenitor markers MASH1, PHOX2A and PHOX2B under treatment of BMPs, FGF8, IGF, TGF-β, ACTIVIN A and GDF. (FIG. 2E) qPCR of norepinephrine neural progenitor markers MASH1, PHOX2A and PHOX2B under a series of ACTIVIN A concentration. (FIG. 2F) qPCR of PHOX2B expression under ACTIVIN A treatment ($2^{nd}$ week) following a series of CHIR99021 concentration at the first week. (FIG. 2G) Immunostaining for the regional marker OTX2 and NE progenitor marker PHOX2B at day 12 when cells were treated with 125 ng/ml ACTIVIN A. FIGS. 3A-3L. (FIG. 3A) Experimental design to target norepinephrine neural progenitor fate specification at the second stage of differentiation. (FIGS. 3B-3C) qPCR of MASH1 and PHOX2B expression under 25 ng/ml and 125 ng/ml ACTIVIN A from day 9 to day 15. (FIGS. 3D-3F)

qPCR of gene expression of regional marker MATH1, OLIG3 and PAX7 under treatment of ACTIVIN A with or without DMH1/Cyclopamine. (FIGS. 3G-3I) qPCR of gene expression of noradrenaline neural progenitor marker MASH1, PHOX2A and PHOX2B expression under treatment of ACTIVIN A with or without DMH1/Cyclopamine. (FIGS. 3J-3K) Immunostaining of norepinephrine neural progenitor marker MASH1 and PHOX2B at day 9 (FIG. 3J) and day 11 (FIG. 3K) during differentiation under the optimized condition. (FIG. 3L) Percentage of MASH1+ and PHOX2B+ norepinephrine neurons differentiated from induced pluripotent stem cells (iPSCs).

FIGS. 4A-4S. (FIG. 4A) qPCR of norepinephrine neuronal marker TH and DBH during differentiation. (FIGS. 4B-4C) Immunostaining of norepinephrine neuronal marker PHOX2B, TH and DBH. (FIGS. 4R-4S) Immunostaining for NPY and GAL in H9 derived NE neurons at day 30. Scale bars, 20 µm.

FIGS. 5A-5L (FIG. 5A) Schematic diagram of experimental design to generate cell line expressing norepinephrine sensor $GRAB_{NE1m}$. (FIG. 5B) $GRAB_{NE1m}$ expression in ES cells and ES-derived norepinephrine neurons. Scale bar indicate 50 µm. (FIG. 5C) time lapse of $GRAB_{NE1m}$ fluorescence under the treatment of norepinephrine. Scale bar indicate 50 µm. (FIG. 5D) $GRAB_{NE1m}$ fluorescent intensity along norepinephrine treatment. $\Delta F/F_0$ refers to the peak change in fluorescence intensity. (FIG. 5E) Comparison of fluorescent intensity before and after norepinephrine administration. (FIGS. 5F-5J) Dynamic $GRAB_{NE1m}$ fluorescent intensity in norepinephrine neurons when treated with control and norepinephrine reuptake inhibitors (Maprotiline, Tomoxetine, Reboxetine, Nisoxetine). (FIG. 5K) Comparison of fluorescent intensity in (FIGS. 5F-5J) before and after drug administration. (FIG. 5L) $GRAB_{NE1m}$ fluorescent intensity along KCl (40 mM) administration with or without extracellular calcium.

(FIG. 6A) Flow cytometry quantification of OTX2 positive cell population in differentiating cells under a series of CHIR99021 concentrations. (FIG. 6B) qPCR of norepinephrine neural progenitor markers MASH1, PHOX2A and PHOX2B under treatment of a series of CHIR99021 concentration. (FIG. 6C) Immunostaining for SOX2, OTX2 and PAX6 at day 6 from cells treated with 1 µM CHIR99021.

(FIG. 7A) Immunostaining for norepinephrine neural progenitor marker MASH1 and PHOX2B at day 6 from cells treated with 1 µM CHIR99021. (FIG. 7B) qPCR of regional neural progenitor markers OLIG3, MATH1 and PAX7 under treatment of BMPs, FGF8, IGF, TGF-β, ACTIVIN A and GDF.

(FIGS. 8A8B) qPCR of MASH1 and PHOX2A expression under Activin A treatment (2nd week) following a series of CHIR99021 concentrations at the first week. (FIG. 8C) Flow cytometry quantification of PHOX2B positive cell population from cells treated ACTIVIN A after being pre-treated with a series of CHIR99021 concentration.

FIGS. 9A-9J. (FIG. 9A) Diagram of norepinephrine neural differentiation protocol disclosed herein. (FIG. 9B) Bright field microscopy of cells under different time points along norepinephrine neural differentiation pathway. (FIGS. 9C-9H) Verification of the differentiation protocol in W24B and W24M hiPSCs. (FIGS. 9I-9J) Quantification of PHOX2B and PHOX2B/TH positive cells in culture. Data are shown as mean±SD. n=5 for each condition.

(FIG. 10A) Schematic diagram of experimental design to generate cell lines expressing norepinephrine sensor $GRAB_{NE1m}$. Genotyping primers are shown by the arrows (see SEQ ID NOS: 1-2 herein). (FIGS. 10B-10C) Genotyping PCR of cell line candidates using primers to detect insertion (FIG. 10B) and homozygosity (FIG. 10C).

FIGS. 11A-11N. (FIG. 11A) Schematic diagram of design for generating TH reporter cell line. (FIG. 11B) mCherry signal and TH immunostaining in differentiated NE neurons. (FIG. 11C) Bright field microscopy and red channel of mCherry fluorescence results when performing the cell patch for electrophysiology. (FIG. 11D) Spontaneous firing from recorded noradrenaline neurons. (FIG. 11E) Na and K current recorded in noradrenaline neurons. (FIG. 11F) Spontaneous firing under 0% $CO_2$ and 5% $CO_2$. (FIG. 11G) Quantification of the firing rate change in panel FIG. 11F. (values shown as mean±SD). (FIG. 11J) Representative image and calcium signals in the TH-labeled neurons before, at, and after cocktail blockers. (FIG. 11K) Quantification of the firing rate change in panel J. Data are shown as symbols and lines in the "before-after" pattern. n=26 neurons. (FIG. 11L) Representative trace of spontaneous firing before, at, and after clonidine (1 mM) treatment. (FIG. 11M) Quantification of the firing rate change in panel L. Data are shown as symbols and lines in the "before-after" pattern. n=6 neurons. (FIG. 11N) Quantification of firing rate change in non-TH cells from the NE differentiating culture.

(FIG. 12A) Schematic diagram of experimental design to generate TH reporter cell line with insertion of Cre recombinase in C-terminal of TH gene. Horizontal arrows indicate primers designed for genotyping (see SEQ ID NOS: 1-2 herein). (FIG. 12B) Genotyping PCR of cell line candidates. Arrows indicate insertion and wild-type bands, respectively.

(FIGS. 13A-13D) immunostaining for GABA, 5HT, VGLUT1, CaMKII and PNMT in NE neurons at day 30. HO, Hoechst. Scale bars in (a-c), 50 µm; Scale bar in (d), 20 µm.

DETAILED DESCRIPTION

Figure 1C:
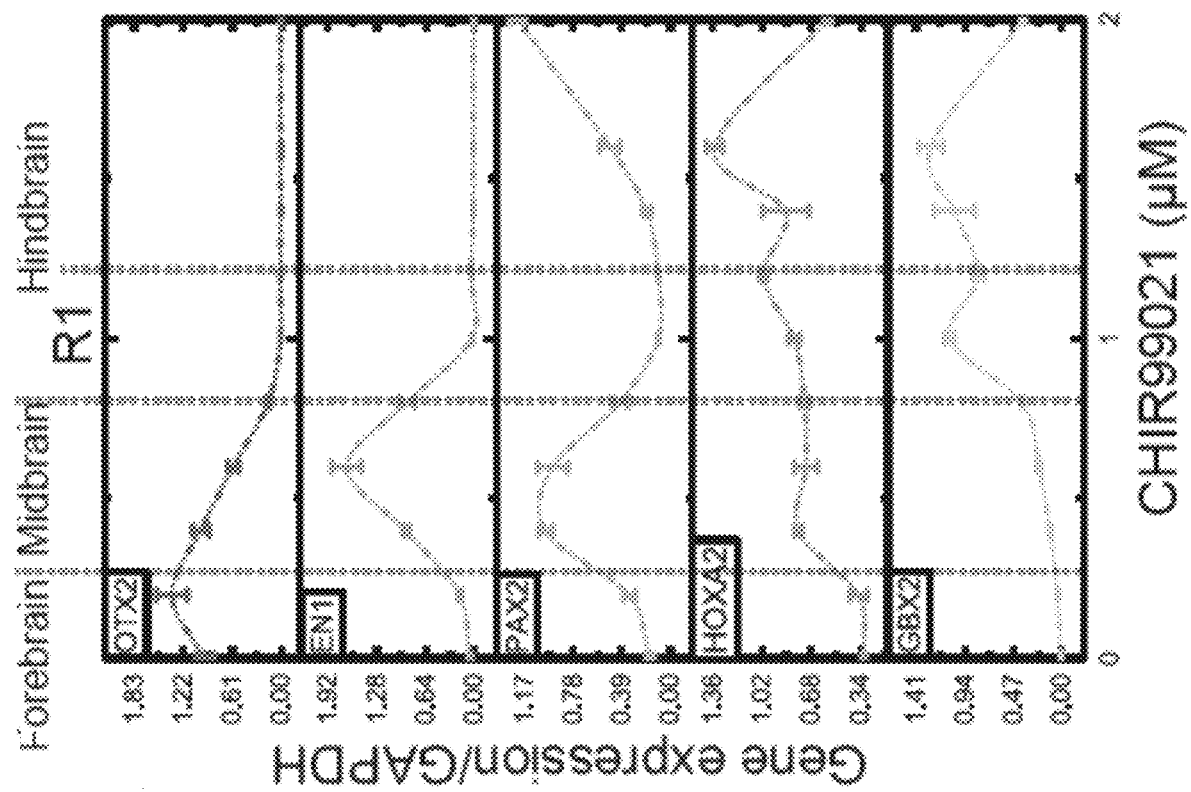

Norepinephrine (NE), also known as noradrenaline (NA), is produced by nuclei such as locus coeruleus (LC) in the central nervous system. NE neurons widely project to virtually all of brain and involve in arousal, wakefulness, memory, focus and attention, "fight or flight" reaction and anxiety. Dysregulation of noradrenergic neurotransmission, which is the neuronal process whereby norepinephrine is released by a pre-synaptic cell upon excitation and crosses the synapse to stimulate or inhibit the post-synaptic cell, has been linked to Alzheimer's disease (AD), Parkinson's disease (PD), Rett syndrome, CCHS, sleep disorders, anxiety, and depression. The methods and compositions provided herein are based at least in part on development disclosed herein of efficient, scalable methods for generating enriched populations of human central nervous system (CNS) NE neurons from human pluripotent stem cells (hPSCs) with high efficiency. In particular, identified herein is a novel and region-specific role of Activin A in directing NE cell fate specification. NE neurons produced according to the methods of this disclosure express characteristic transcription factors and enzymes, produce and release NE neurotransmitter, are regulated by known NE reuptake inhibitors, and display electrophysiological properties of endogenous NE neurons. In particular, the NE neurons provided herein increase firing rate in response to $CO_2$ stimulation, a characteristic feature of NE neurons that is essential for regulating breathing. The methods and compositions described herein enable large-scale, standardized production of human NE neurons from hPSCs for disease modeling, drug development, and cell therapies.

Methods

Accordingly, in a first aspect, this disclosure provides in vitro methods for efficiently and robustly producing human norepinephrine (NE) neurons. As used herein, the term "norepinephrine neuron" ("NE neuron") in general refers to a neuronal cell capable of expressing norepinephrine. NE neurons are characterized by noradrenergic neurotransmission and by expression of tyrosine hydroxylase (TH) and dopamine β-hydroxylase (DBH). The term "NE neuron progenitor" refers to a precursor cell of a NE neuron. NE neuron progenitors are characterized by expression of MASH1, PHOX2B, and PHOX2A, and are negative for Otx2 expression.

In some embodiments, provided herein are methods for generating human norepinephrine (NE) neuron progenitor cells comprising culturing human neuroepithelial cells having hindbrain R1 regional identity for about 2-4 days in a first culture medium comprising a first concentration of Activin A; and then culturing these cultured cells for about 2-4 days in a second culture medium comprising a second concentration of Activin A, where the second concentration is greater than the first concentration, to obtain an enriched cell population comprising greater than about 40% norepinephrine (NE) neuron progenitor cells expressing MASH1+/PHOX2B+/PHOX2A+ and negative for OTX2 and HOX2A expression. In some embodiments, the human neuroepithelial cells having hindbrain R1 regional identity where cultured in the presence of about 25 ng/ml ActivinA from day 0 to day 2 (with day 0 being the first day of generating human NE neuron progenitors). On about day 2, the cultured cells were further cultured from day 2 to day 4 in the presence of about 125 ng/ml Activin A.

As used herein, the term "neuroepithelial cells having hindbrain R1 region identity" refers to neuroepithelial precursor cells that express GBX2 but do not express OTX2 or HOXA2, and correspond to neuroepithelial cells found in hindbrain R1 region of the developing brain. As used herein, the terms "purified" or "enriched" cell populations are used interchangeably, and refer to cell populations, in vitro or ex vivo, that contain a higher proportion of a specified cell type or cells having a specified characteristic than are found in vivo (e.g., in a tissue). As used herein, an enriched population of NE neuron progenitor cells refers to a cell composition comprising at least 40%, or at least 50%, or at least 60% of norepinephrine (NE) neuron progenitor cells expressing MASH1+/PHOX2B+/PHOX2A+ and negative for OTX2 and HOX2A expression obtained by methods of this disclosure.

In some embodiments, a culture medium for use according to a method provided herein comprises a basal culture medium supplemented with chemical compounds, growth factors, or other components such as those described herein. For example, a culture medium can comprise a basal culture medium such as DMEM/F-12 or Neurobasal® culture medium (Life Technologies). Preferably, the basal culture medium is chemically defined. The term "chemically defined culture medium" or "chemically defined medium," as used herein, means that the molecular identity, chemical structure, and quantity of each medium ingredient is definitively predetermined. The term "ingredient," as used herein, refers to a component the molecular identity and quantity of which is known. In some embodiments, a chemically defined medium is free of any xenogeneic-components (termed "xeno-free" herein) and instead comprises human proteins, which can be produced using recombinant technology or derived from placenta or other human tissues in lieu of animal-derived proteins. In some embodiments, all proteins added to the medium are human recombinant proteins.

In some embodiments, the basal culture medium is supplemented to comprise one or more additional components including, without limitation, N2 neural supplement (N-2 Supplement; Gibco), B27 neural supplement (B-27 Supplement; Gibco), and non-essential amino acid (NEAA) supplement. In some embodiments, the culture medium comprises DMEM/F12+Neurobasal® medium at 1:1 ratio, 1×N2 neural, and 1×B27 neural supplement. In some embodiments, the first culture medium comprises DMEM/F-12, N2 supplement, NEAA supplement, and a first concentration of Activin A. In some embodiments, the second culture medium comprises DMEM/F-12, N2 supplement, B27 supplement, NEAA supplement, and a second concentration of Activin A.

In some embodiments, the first concentration of Activin A is a concentration of about 10 ng/ml to about 50 ng/ml. In some embodiments, the first concentration of Activin A is about 25 ng/ml. As demonstrated in the Example section, high expression of MASH1 was obtained using a first concentration of about 25 ng/ml Activin A, but the first concentration could be higher or lower amounts depending on the desired yield, provided that the first concentration is lower than the second.

In some embodiments, the second concentration of Activin A is a concentration of about 100 ng/ml to about 250 ng/ml. In some embodiments, the first concentration of Activin A is about 125 ng/ml. As demonstrated in the Example, high expression of PHOX2B was obtained using a second concentration of about 125 ng/ml Activin A, but the second concentration could be higher or lower amounts depending on the desired yield, provided that the second concentration is higher than the first. As set forth herein, "low expression" is the expression level in the cell when Activin A was not introduced into the culture, whereas "high expression" is the expression in the cell when Activin A concentration in the culture reaches 250 ng/ml.

In some embodiments, the culture medium for each culturing step further comprises an inhibitor of bone morphogenetic protein (BMP) signaling. The BMP signaling inhibitor can be DMH1 (4-[6-(4-Isopropoxyphenyl)pyrazolo[1,5-a]pyrimidin-3-yl]quinoline, 4-[6-[4-(1-Methyl ethoxy)phenyl]pyrazolo[1,5-a]pyrimidin-3-yl]-quinoline), which blocks BMP signaling by inhibiting Activin receptor-like kinase (ALK2) (Chambers et al., 2009, "Highly efficient neural conversion of human ES and iPS cells by dual inhibition of SMAD signaling." *Nat Biotechnol* Vol. 27, 275-280; Neely et al., 2012, "DMH1, a highly selective small molecule BMP inhibitor promotes neurogenesis of hiPSCs: comparison of PAX6 and SOX1 expression during neural induction." *ACS Chem Neurosci* Vol. 3, 482-491). Other small molecule inhibitors of Activin receptor-like kinases that can be used to block BMP signaling include but are not limited to Dorsomorphin and LDN-193189. Both compounds affect SMAD-dependent and SMAD-independent BMP signaling triggered by BMP2, BMP6, or GDF5. (Boergermann et al., 2010, *Int. J. Biochem. Cell Biol.* 42(11):1802-7.) As used herein, the term "LDN-193189" refers to a small molecule DM-3189, IUPAC name 4-(6-(4-(piperazin-1-yl)phenyl)pyrazolo[1,5-a]pyrimidin-3-yl)quinoline, having a chemical formula of $C_{25}H_{22}N_6$. LDN-193189 is capable of functioning as a SMAD signaling inhibitor. LDN-193189 is also a highly potent small-molecule inhibitor of ALK2, ALK3, and ALK6, protein tyrosine kinases (PTK), inhibiting signaling of members of the ALK1 and ALK3 families of type I TGFβ receptors, resulting in the inhibition of the transmission of multiple biological signals, including the bone morphogenetic proteins (BMP) BMP2, BMP4, BMP6, BMP7, and Activin cytokine signals and subsequently SMAD phosphorylation of Smad1, Smad5, and Smad8 (Yu et al., 2008, *Nat Med* 14:1363-1369; Cuny et al., 2008, *Bioorg. Med. Chem. Lett.* 18: 4388-4392, herein incorporated by reference). BMP inhibitors such as those described herein are available from commercial vendors of chemical compounds.

In some embodiments, the inhibitor of BMP signaling (including but not limited to DMH1) is provided at a concentration of about 1 μM-5 μM. In some embodiments, DMH1 is provided at a concentration of about 2 μM.

In some embodiments, the method further comprises directing differentiation of norepinephrine (NE) neuron progenitor cells obtained according to the methods of this disclosure to obtain a substantially pure population of human NE neurons that express TH and DBH. In some embodiments, the method comprises culturing the population comprising human NE neuron progenitor cells for at least 6 days in a neural differentiation medium comprising BDNF, GDNF, TGF-β1, and ascorbic acid; and detecting within the cultured cells a population of cells positive for tyrosine hydroxylase (TH) and dopamine β-hydroxylase (DBH) expression, whereby a population comprising at least 40% human TH+/DBH+NE neurons is obtained. As used herein, "an enriched population of NE neurons" refers to a cell composition comprising at least 40%, at least 50%, or at least 60% of norepinephrine (NE) neurons expressing tyrosine hydroxylase (TH) and dopamine β-hydroxylase (DBH). In some embodiments, the neural differentiation medium further comprises cyclic AMP (cAMP), which is shown in the examples to boost yield of human TH+/DBH+NE neurons.

Preferably, the neural differentiation medium comprises a basal medium such as DMEM/F12 or Neurobasal® medium supplemented to comprise one or more additional components including, without limitation, N2 neural supplement (N-2 Supplement; Gibco), B27 neural supplement (B-27 Supplement; Gibco), and non-essential amino acid (NEAA) supplement. In some embodiments, the neural differentiation medium comprises DMEM/F12+Neurobasal® medium at 1:1 ratio, 1×N2 neural, and 1×B27 neural supplement, and further comprises BDNF at an amount of about 5-15 ng/ml, GDNF at an amount of about 5-15 ng/ml, TGF-β1 at an amount of about 0.5-15 ng/ml, and ascorbic acid at an amount of about 100-400 μM. In some embodiments, the neural differentiation medium comprises DMEM/F12+Neurobasal® medium at 1:1 ratio, 1×N2 neural, and 1×B27 neural supplement, and further comprises about 10 ng/ml BDNF, about 10 ng/ml GDNF, about 200 μM ascorbic acid, about 1 μM cAMP, and about 1 ng/ml TGF-β1.

Any appropriate method(s) can be used to characterize NE neurons obtained according to the methods of this disclosure. For instance, NE neurons are responsive to $CO_2$. Accordingly, NE neurons obtained according to the methods of this disclosure can be assayed for responsiveness to levels of $CO_2$. NE neurons obtained according to the methods of this disclosure can be assayed for responsiveness to a norepinephrine reuptake inhibitor. Norepinephrine reuptake inhibitors include, without limitation, Maprotiline, Tomoxetine, Reboxetine, and Nisoxetine. As demonstrated in the Examples, exposure of NE neurons to norepinephrine reuptake inhibitors increases the level of NE released by the neurons into the supernatant.

In some embodiments, neuroepithelial cells having hindbrain R1 region characteristics and identity used in the methods set forth above are obtained from human pluripotent stem cells (hPSCs). In particular, human pluripotent stem cells can be directed to differentiate into human neuroepithelial cells having hindbrain R1 region identity and, thus, can be suitable for differentiation into human NE neurons according to the methods of this disclosure. As used herein, the term "pluripotent stem cell" (e.g., hPSC) means a cell capable of continued self-renewal and capable, under appropriate conditions, of differentiating into cells of all three germ layers. hPSCs exhibit a gene expression profile that includes $SOX2^+$ and $OCT4^+$. Examples of hPSCs include human embryonic stem cells (hESCs) and human induced pluripotent stem cells (hiPSCs). As used herein, "iPS cells" or "iPSCs" refer to cells that are substantially genetically identical to their respective differentiated somatic cell of origin and display characteristics similar to higher potency cells, such as ES cells, as described herein. Such cells can be obtained by reprogramming non-pluripotent (e.g., multipotent or somatic) cells according to methods known to practitioners in the art.

To induce the specification of neuroepithelial cells from human pluripotent cells, the dual TGFβ/BMP inhibition approach can be applied to human pluripotent stem cells in a monolayer culture. See, for review, Chambers et al., 2009, *Nature Biotech.* 27:275-280. The small molecule SB431542 represses TGFβ signaling by selectively inhibiting Activin receptor-like kinase ALK4/5/7. DMH1 represses BMP signaling by selectively inhibiting the BMP receptor kinase ALK2. In the methods set forth herein, human pluripotent stem cells are treated with DMH1 and SB431542 for about 1 week. Treated cells were then induced to differentiate into populations comprising about 85% $SOX1^+$ neuroepithelial cells but also comprising other cell lineages due to spontaneous pluripotent cell differentiation, since SB431542 and DMH1 are unable to prevent all spontaneous differentiation into other cell lineages, especially when ESC colonies are small. To further improve neural specification, inhibitors of glycogen synthase kinase-3, such as CHIR99021, can be applied in combination with DMH1 and SB431542. GSK3 negatively regulates WNT signaling, and WNT signaling promotes self-renewal of ESCs and neural progenitors. When exposed to these three molecules (CHIR99021, DMH1, and SB431542) for about 6 days, human pluripotent stem cells not only generated more pure populations of SOX1$^+$ neuroepithelial cells (e.g., at least 95% of cells in the total population were SOX1$^+$ neuroepithelial cells), but also generated 2.5-fold more neuroepithelial cells. However, CDS (CHIR99021, DMH1, and SB431542) treatment-derived neuroepithelial cells showed caudal identity as demonstrated by staining for HOXA2. By contrast, "DS" (DMH1 and SB431542) treatment-derived neuroepithelial cells showed rostral identity as demonstrated by staining for OTX2.

In some embodiments, the method comprises culturing human pluripotent stem cells (hPSCs) in a culture medium comprising an inhibitor of BMP signaling, an inhibitor of TGFβ signaling, and a Wnt agonist for about 6 days, whereby a population of neuroepithelial cells having hindbrain R1 regional identity are obtained.

In another aspect, provided herein are methods for producing and using NE neurons genetically modified to express a tyrosine hydroxylase (TH) reporter including but not limited to Tomato, a fluorescence protein. Tyrosine hydroxylase is a rate-limiting enzyme in the biosynthesis pathway of the catecholamine neurotransmitters: dopamine, epinephrine, and norepinephrine. NE neurons genetically modified to comprise the TH reporter line enable precise reporting for NE neurons in a cell culture that permit by way of example, molecular, histological, and electrophysiological analyses. The reporter also enables isolation of substantially pure NE neurons based on its detectable expression. In addition, the TH reporter can be used when differentiating patient-derived iPSCs to study various disease phenotypes specifically in NE neurons. In some embodiments, the method comprises introducing into human TH+/DBH+NE neurons obtained according to methods of this disclosure a heterologous nucleotide sequence encoding a tyrosine hydroxylase (TH) reporter operably linked to a detectable reporter. Detectable reporters that can be used according to the methods provided herein include, without limitation, biotin, digoxigenin, enzymatic reporters (e.g., β-galactosidase, alkaline phosphatase, DHFR, CAT), fluorescent or chemiluminescent reporters (e.g., fluorescein, GFP, GFP variants, mCherry, luciferase, e.g., luciferase derived from the firefly (*Photinus pyralis*) or the sea pansy (*Renilla reniformis*) and mutants thereof).

In certain aspects, provided herein is a substantially pure population of human NE neurons comprising a heterologous nucleotide sequence encoding a β2 adrenergic G protein-coupled receptor (GPCR) activation-based norepinephrine (GRAB$_{NE}$) sensor introduced thereto substantially as set forth in Feng et al., 2019, A Genetically Encoded Fluorescent Sensor for Rapid and Specific In Vivo Detection of Norepinephrine, *Neuron* 102: 745-761, which is incorporated by reference herein in its entirety.

In another aspect, provided herein are methods for producing and using NE neurons genetically modified to express a NE sensor that detects concentrations of noradrenaline in a cell culture. The NE sensor-expressing neurons can be used for drug screening, drug discovery, or drug response. For example, cells expressing the NE sensor can be used to screen candidate drugs to identify those that increase NE production. Such drugs could be used for disorders such as anxiety, depression, and attention deficit hyperactivity disorder (ADHD) that are associated with low NE levels.

As used herein, the term "genetic modification" and its grammatical equivalents can refer to one or more alterations of a nucleic acid, e.g., the nucleic acid within the genome of an organism or cells thereof. For example, genetic modification can refer to alterations, additions, and/or deletion of genes. A genetically modified cell can also refer to a cell with an added, deleted and/or altered gene. Procedures for producing genetically modified cells are generally known in the art, and are described in Sambrook et al., 1989, *Molecular Cloning, A Laboratory Manual*, Cold Spring Harbor Press, Cold Spring Harbor, N.Y., incorporated herein by reference. In some embodiments, genetic modifications are produced using a form of gene editing. The term "gene editing" and its grammatical equivalents as used herein can refer to genetic engineering in which one or more nucleotides are inserted, replaced, or removed from a genome. For example, gene editing can be performed using a nuclease (e.g., a natural-existing nuclease or an artificially engineered nuclease); an example is CRISPR (Jinek et al., 2012, *Science* 337: 816-821; Cong et al., 2013, *Science* 339: 819-823). Other methods of making genetic modifications suitable for use according to the methods provided herein include but are not limited to somatic cell nuclear transfer (SCNT) and introduction of a heterologous nucleotide sequence or "transgene." In some embodiments, the method comprises introducing into human TH+/DBH+NE neurons obtained according to methods of this disclosure a heterologous nucleotide sequence encoding a β2 adrenergic G protein-coupled receptor (GPCR) Activation-Based norepinephrine (GRAB$_{NE}$) sensor operably linked to a detectable reporter.

NE neurons genetically modified to comprise the GRAB$_{NE}$ sensor are useful for a variety of applications including, for example, screening a test compound (e.g., known or unknown chemical compounds) for effects on noradrenergic neurotransmission. In some embodiments, a screening method comprises exposing a test compound to human NE neurons genetically modified to express the GRAB$_{NE}$ sensor and examining the effect of the compound on the GRAB$_{NE}$ sensor as an indicator of noradrenergic signaling of the contacted modified human NE neurons. Preferably, results of such exposure are compared to noradrenergic signaling of a control cell population that has not been exposed to the test compound.

In some embodiments, it can be advantageous to detect and/or measure a positive or negative change in an expression level of at least one gene following exposure (e.g., contacting) of a NE neuron, including genetically unmodified ("wild-type" NE neurons) or genetically modified NE neurons of this disclosure (e.g., modified to express a TH reporter construct or a GRAB$_{NE}$ sensor). In some embodiments, detecting and/or measuring a positive or negative change in a level of expression of at least one gene following exposure (e.g., contacting) of a NE neuron to a test compound comprises whole transcriptome analysis using, for example, RNA sequencing. In such embodiments, gene expression is calculated using, for example, data processing software programs such as Light Cycle, RSEM (RNA-seq by Expectation-Maximization), Excel, and Prism. See Stewart et al., 2013, *PLoS Comput. Biol.* 9:e1002936. In some embodiments, detecting comprises performing a method such as RNA sequencing, gene expression profiling, transcriptome analysis, metabolome analysis, detecting a reporter or sensor, protein expression profiling, Forster resonance energy transfer (FRET), metabolic profiling, and microdialysis.

The term "detect" or "detection" as used herein indicates the determination of the existence, presence or fact of a target or signal, including but not limited to a sample, a reaction mixture, a molecular complex and a substrate including a platform and an array. Detection is "quantitative" when it refers, relates to, or involves the measurement of quantity or amount of a target or signal (also referred as quantitation), which includes but is not limited to any analysis designed to determine the amounts or proportions of the target or signal. Detection is "qualitative" when it refers, relates to, or involves identification of a quality or kind of a target or signal in terms of relative abundance to another target or signal, which is not quantified. An "optical detection" method indicates detection performed through visually detectable signals: fluorescence, spectra, or images from a molecule of interest or a probe attached to the molecule.

Articles of Manufacture

In another aspect, provided herein is an article of manufacture such as a kit for generating substantially pure populations of human norepinephrine neurons. In some embodiments, the kit comprises one or more of a culture medium or plurality of culture medium components (e.g., Activin A, an inhibitor of BMP signaling), or a vector to introduce a TH reporter construct or a $GRAB_{NE}$ sensor as described herein. In some embodiments, the kit further comprises reagents and other materials useful for introducing vectors into cells and for culturing modified cells according to the methods. In some embodiments, the kit further comprises instructions for performing the methods of this disclosure.

In some embodiments, the materials described above as well as other materials can be packaged together in any suitable combination as a kit useful for performing, or aiding in the performance of, a method provided herein. It is useful if the components in a kit are designed and adapted for use together in the disclosed method. For example, disclosed herein are kits comprising genetically modified human NE neurons produced by the disclosed methods. In some embodiments, kits also can contain a cell culture medium, labels, and/or other reagents for the cell culture and detection of biological markers, polypeptides, or nucleic acids of interest in the genetically modified NE neurons.

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide can refer to an individual protein or a collection of proteins. One or more of the amino acids in a protein, peptide, or polypeptide can be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide can also be a single molecule or can be a multi-molecular complex. A protein, peptide, or polypeptide can be just a fragment of a naturally occurring protein or peptide. A protein, peptide, or polypeptide can be naturally occurring, recombinant, or synthetic, or any combination thereof. A protein can comprise different domains, for example, a nucleic acid binding domain and a nucleic acid cleavage domain. In some embodiments, a protein comprises a proteinaceous part, e.g., an amino acid sequence constituting a nucleic acid binding domain.

Nucleic acids and/or other constructs of the invention can be isolated. As used herein, "isolated" means to separate from at least some of the components with which it is usually associated whether it is derived from a naturally occurring source or made synthetically, in whole or in part.

Nucleic acids, proteins, and/or other compositions (e.g., cell population) described herein can be purified. As used herein, "purified" means separate from the majority of other compounds or entities, and encompasses partially purified or substantially purified. Purity can be denoted by a weight by weight measure and can be determined using a variety of analytical techniques such as but not limited to mass spectrometry, HPLC, etc.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

In describing the embodiments and claiming the invention, certain terminology will be used in accordance with the definitions set forth herein.

As used in this specification and the appended claims, the singular forms "a," "an," and "the" include plural references unless the context clearly dictates otherwise. Any reference to "or" herein is intended to encompass "and/or" unless otherwise stated.

In interpreting this disclosure, all terms should be interpreted in the broadest possible manner consistent with the context. Variations of the term "comprising" should be interpreted as referring to elements, components, or steps in a non-exclusive manner, so the referenced elements, components, or steps can be combined with other elements, components, or steps that are not expressly referenced. In the specification and in the claims, the terms "including" and "comprising" are open-ended terms and should be interpreted to mean "including, but not limited to." These terms encompass the more restrictive terms "consisting essentially of" and "consisting of." Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

The terms "about" and "approximately" shall generally mean an acceptable degree of error for the quantity measured given the nature or precision of the measurements. Typical, exemplary degrees of error are within 10%, and preferably within 5% of a given value or range of values. Alternatively, and particularly in biological systems, the terms "about" and "approximately" can mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The phrase "and/or," as used herein in the specification and in the claims, should be understood to mean "either or both" of the elements so conjoined, i.e., elements that are conjunctively present in some instances and disjunctively present in other instances. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements).

The practice of the present invention will employ, unless otherwise indicated, conventional techniques of molecular biology, cell biology, and recombinant DNA, which are within the skill of the art. Such techniques are explained fully in the literature. See e.g., Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (TRL Press, 1986); B. Perbal, A Practical Guide To Molecular Cloning (1984)).

Various exemplary embodiments of compositions and methods according to this invention are now described in the following non-limiting Examples. The Examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

Examples

Set forth herein are methods for highly efficient generation of human central NE neurons from human pluripotent stem cells. As described herein, a novel and regional specific role of Activin A in NE cell fate specification was identified. NE neurons produced as disclosed herein are capable of producing and releasing NE neurotransmitter, which was regulated by NE reuptake inhibitors. By engineering NE neurons expressing a NE sensor, $GRAB_{NE1m}$, it was possible to screen drugs regulating extracellular NE levels, thus providing a scalable platform for drug discovery. Accordingly, the first central NE differentiation model for NE development and disease modeling is demonstrated in these Examples, which enables cell therapy and drug development for NE related diseases.

Methods hPSC culture: H9 and genetically modified cell lines derived from H9 were maintained on irradiated mouse fibroblast cells (MEFs). Cells were cultured in medium containing DMEM/F12 basal medium, 20% KnockOut serum replacement, 0.1 mM β-mercaptoethanol, 1 mM L-glutamine, 1× nonessential amino acids (NEAA), and 4 ng/mL FGF-2. The cells were passaged weekly by treatment with 1 mg/ml Dispase.

NE neuron differentiation: 2 days after hPSC passage (meaning, day 0 of NE differentiation), the cells were cultured in medium ("N2 medium") containing DMEM/F12 (1:1), 1% N2 and 1×NEAA, and supplemented with 2 µM SB431542, 2 µM DMH1, and 1 µM CHIR99021 for 4 days. On day 4, the cells were lifted by gently blowing with 1 ml pipet and cultured in the same medium for 1 additional day in suspension. On day 5, change the medium without SB431542. On day 6, floating spheres were plated on Matrigel-coated plates and cultured in N2 medium with Activin A (25 ng/ml) for 3 days. Cells were feed daily. On day 9, cells were cultured with medium ("N2B27 medium") containing DMEM/F12/Neuralbasal (1:1), 1% N2, 2% B27 and 1×NEAA, and supplemented with 125 ng/ml Activin A and 1 µM c-AMP for another 3 days. At around day 12, the cells were committed to NE fate and ready to generate NE neurons. For NE neuron differentiation, cells were digested into small clusters or single cells by Accutase and cultured in medium ("B27 medium") consisting of neurobasal, 1×B27, 1×NEAA, 1% GlutaMAX, and supplemented with 1 µM c-AMP, 0.2 mM ascorbic acid, 10 ng/ml glial cell line-derived neurotrophic factor (GDNF), 10 ng/ml brain-derived neurotrophic factor (BDNF) and 1 ng/ml transforming growth factor β1.

Genome editing: Scarless genome editing was performed using CRISPR/Cas9 following published methods. See Steyer et al., 2018, *Stem Cell Reports*, 10:642-654. FIGS. 11A-11G illustrate the methodology used for genomic editing; gRNA sequences used in these methods were:

For AAVS1 site: GGGGCCACTAGGGACAGGAT (SEQ ID NO. 1)

For TH c-terminal site: TAGGTGCACGGCGTCCCTGA (SEQ ID NO.2)

gRNA was designed according to Benchling. Donor plasmid was generated by NEBuilder® HiFi DNA Assembly Master Mix (NEB, E2621S). Briefly, hPSCs were digested by TrypLE Express. Gene Pulser Xcell (Bio-Rad) was used for CRISPR/Cas9 delivery. Two-million cells were electroporated with 15 µg of sgRNA plasmid (pLenti-CRISPR) with 30 µg donor plasmid. Cells were plated at ~150,000 cells/well of 6-well plate. Starting 24 hours after electroporation, 0.5 µg/ml puromycin were added to the culture medium. After 3 days of puromycin selection, hPSCs were switched to their normal culture medium and fed every other day until approximately 1-2 weeks after electroporation when distinct colonies were established.

Cell transplantation: Small aggregates of NE neural progenitors (day 10-day 12) were collected and suspended in artificial cerebral spinal fluid (aCSF) containing Rock inhibitor (0.5 µM), at a concentration of 100,000 cells/µl. 1 µl of cells were slowly injected into the left cortex (AP=+0.0 mm, ML=+1.8 mm, DV=-1.7 mm, from skull) of adult SCID mice (8-12 weeks) that were anesthetized with 1%-2% isoflurane mixed in oxygen.

Immunocytochemistry and flow cytometry: Immunocytochemistry was performed as described previously. See Huang et al., 2016, *Sci Rep*, 6:32600, doi:10.1038/srep32600. In brief, cells on coverslips were fixed in 4% neutral-buffered paraformaldehyde (PFA) for 10 minutes (min) at room temperature. Following rinsing with PBS, these cells were incubated in 0.2% Triton X-100 (in phosphate buffered saline (PBS)) for 10 min followed by 10% donkey serum (in PBS) at room temperature for 1 hour (h). The cells were then incubated with primary antibodies diluted in 5% donkey serum in 0.1% Triton X100 (in PBS) at 4° C. overnight, followed by fluorescently conjugated secondary antibodies at room temperature for 30 min. The nuclei were stained with Hoechst. Images were collected with a Nikon A1 laser-scanning confocal microscope. Flow cytometry was performed using Transcription Factor Buffer Set which is designed for transcription factor staining following manufacturer's instruction. Briefly, single cells were prepared using TrypLE Express Enzyme and fixed in the fixation buffer provided by the kit at 2-8° C. for 45 min. After 3 washings with the permeable buffer, primary antibodies were added to cells for 45 min at 2-8° C. in a light-tight box. Cells were washed three times before fluorescently conjugated secondary antibodies. Second antibodies were incubated with cells for 45 minutes at 2-8° C. in a light-tight box and followed by washing three times. After the last wash, cells were suspended in washing buffer and analyzed by flow cytometry (BD LSR or BD LSRII). Data analysis was performed using FlowJo.

ELISA: To detect NE release into medium during neuronal differentiation, supernatant was collected at indicated time points along differentiation. Enzyme-linked immunosorbent assay (ELISA) were performed using a Noradrenaline (Norepinephrine) ELISA Assay Kit (EAGLE, NOR31-K01) following the manufacturer's instructions.

Electrophysiology: Whole-cell patch-clamp recordings were made from human ESC-derived NE neurons at 4 weeks. Briefly, the NE neurons were held at −70 mV to record the Na+/K+ channel activities with voltage-clamp model. For recording action potentials, the cells were held at 0 pA with the current-clamp model, and with the steps of injected currents from −50 pA to +50 pA. The bath solution consisted of 135 mM NaCl, 3 mM KCl, 2 mM $CaCl_2$), 1 mM $MgCl_2$, 10 mM HEPES, 11 mM glucose, 10 mM sucrose, pH7.4. Recording pipettes were filled with an intracellular solution containing 120 mM potassium D-gluconate, 1 mM ethylene glycol-bis (β-aminoethylether) N,N,N',N'-tetraacetic acid (EGTA), 10 mM 4-(2-hydroxyethyl) piperazine-1-ethanesulfonic acid (HEPES), 4 mM ATP-Mg, 0.3 mM GTP-Na, 10 mM phosphocreatine, 0.1 mM $CaCl_2$), 1 mM $MgCl_2$, pH 7.2, 280-290 mOsm/L. An Olympus BX51WI microscope was used to visualize neurons. A MultiClamp 700B amplifier (Axon instruments, Molecular Devices, Sunnyvale, CA, USA) was used to investigate the voltage clamp and current clamp recordings. Signals were filtered at 4 kHz using a Digidata 1550B analog-digital converter (Axon instruments) and stored for further analysis. Data were analyzed with Clampfit 11.0.3 (Axon instruments), GraphPad Prism 5 (GraphPad Software Inc., La Jolla, CA, USA), CorelDraw 2019 (Corel, Canada), Igor 4.0 (WaveMetrics, Lake Oswego, OR, USA).

Calcium imaging and analysis: Neuronal $Ca^{2+}$ imaging, image processing, and data analysis were performed as described previously with modifications (Dong, Q. et al. Mechanism and consequence of abnormal calcium homeostasis in Rett syndrome astrocytes. *Elife* 7, doi: 10.7554/eLife.33417 (2018). Briefly, cells were bulk-loaded with Fluo-4/AM for 15 min at 37° C. in artificial cerebrospinal fluid (aCSF) containing Fluo-4/AM (12.5 µg/ml), pluronic acid (0.05%), and DMSO (0.1%). Then cells were transferred to a chamber, and $Ca^{2+}$ imaging was performed with a Nikon A1 confocal microscope at room temperature. All image data were taken in the frame-scanning mode at 4 frames per second. The $Ca^{2+}$ imaging data were analyzed using Python. $Ca^{2+}$ signals were presented as relative fluorescence changes (ΔF/F0) from specified regions of interest (ROIs). In this experiment, only mCherry+ cells were selected for analysis. For the traces with baseline drift, baseline correction was performed using a rolling ball algorithm. The peaks were detected using the algorithm developed by Matlab (findpeaks function). The frequency and amplitude were calculated and measured. Images with obvious motion were excluded for analysis. In experiments that examined spontaneous $Ca^{2+}$ oscillations, the $Ca^{2+}$ level was reported as ΔF/F0=(Ft−F0)/F0. Calcium elevation events were detected with thresholds of 3 times of standard deviation of the baseline.

Fluorescence imaging of $GRAB_{NE1m}$ sensor cells: The neurons were plated following the NE differentiation protocol and cultured on a 35-mm glass bottom dish (well size 14 mm, #1.5 glass-like polymer cover slip (D35-14-1.5P, Cellvis) until day 30 for maturation. Expression $GRAB_{NE1m}$ in hPSC-derived NE neurons was imaged live under the Nikon A1 confocal microscope. The cells were allowed to condition at room temperature after changed to the electrophysiological buffer consisting of 135 mM NaCl, 3 mM KCl, 2 mM $CaCl_2$), 1 mM $MgCl_2$, 10 mM HEPES, 11 mM glucose, 10 mM sucrose, pH7.4. Then the cells were recorded for 6~7 mins under 20× objective with PFS on to monitor the dynamic fluorescent intensity change before treatments with neurotransmitters (NE, DA, 5-HT or control solution) or drugs (DA, 5HT and NE reuptake inhibitors) at indicated concentration. The extracellular NE level changes were quantified by ΔF/F0=(Ft−F0)/F0 using imageJ.

Results

Dorsal Hindbrain R1 Progenitors were Efficiently Specified from hPSCs

Figure 1D:
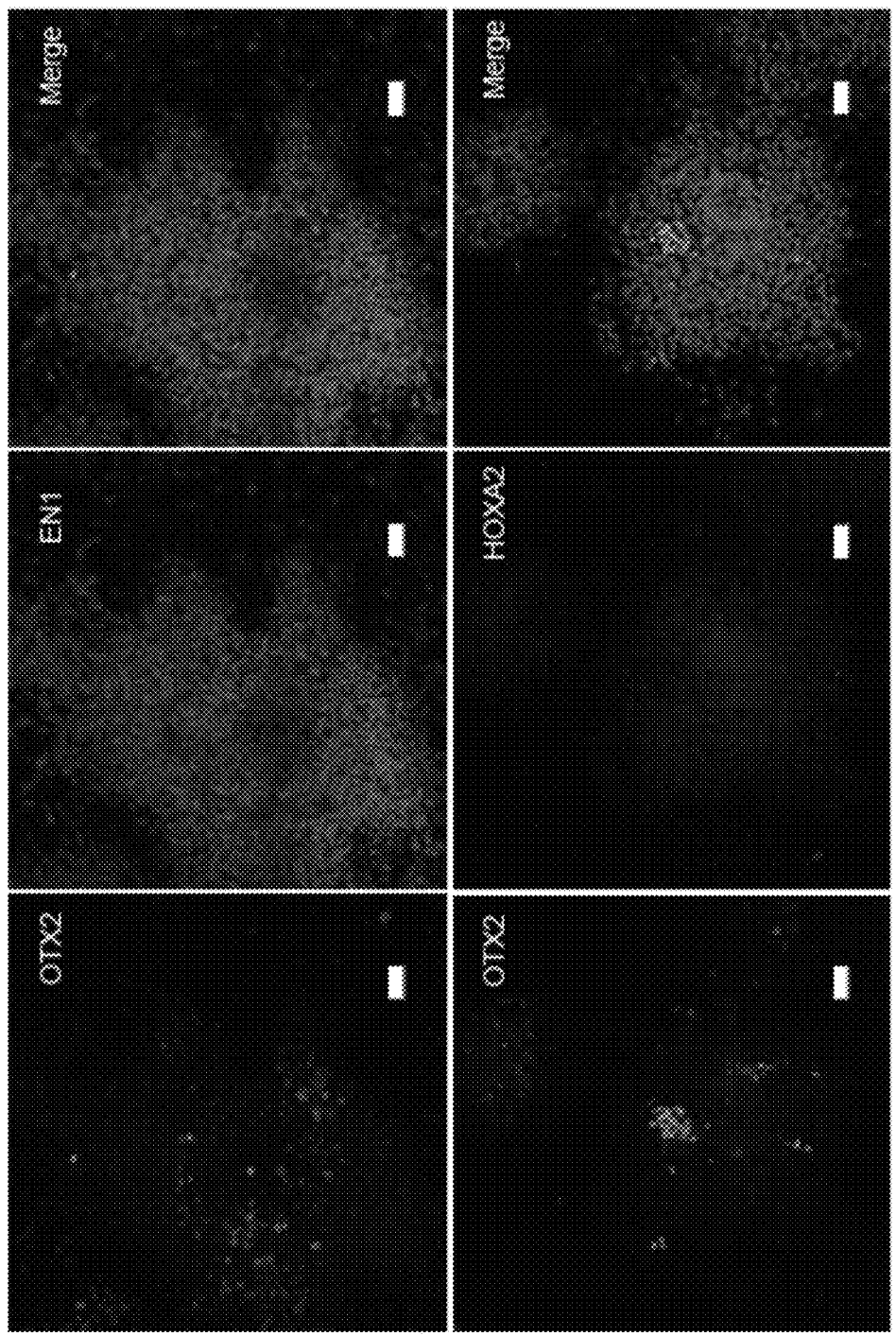
Figure 1E:
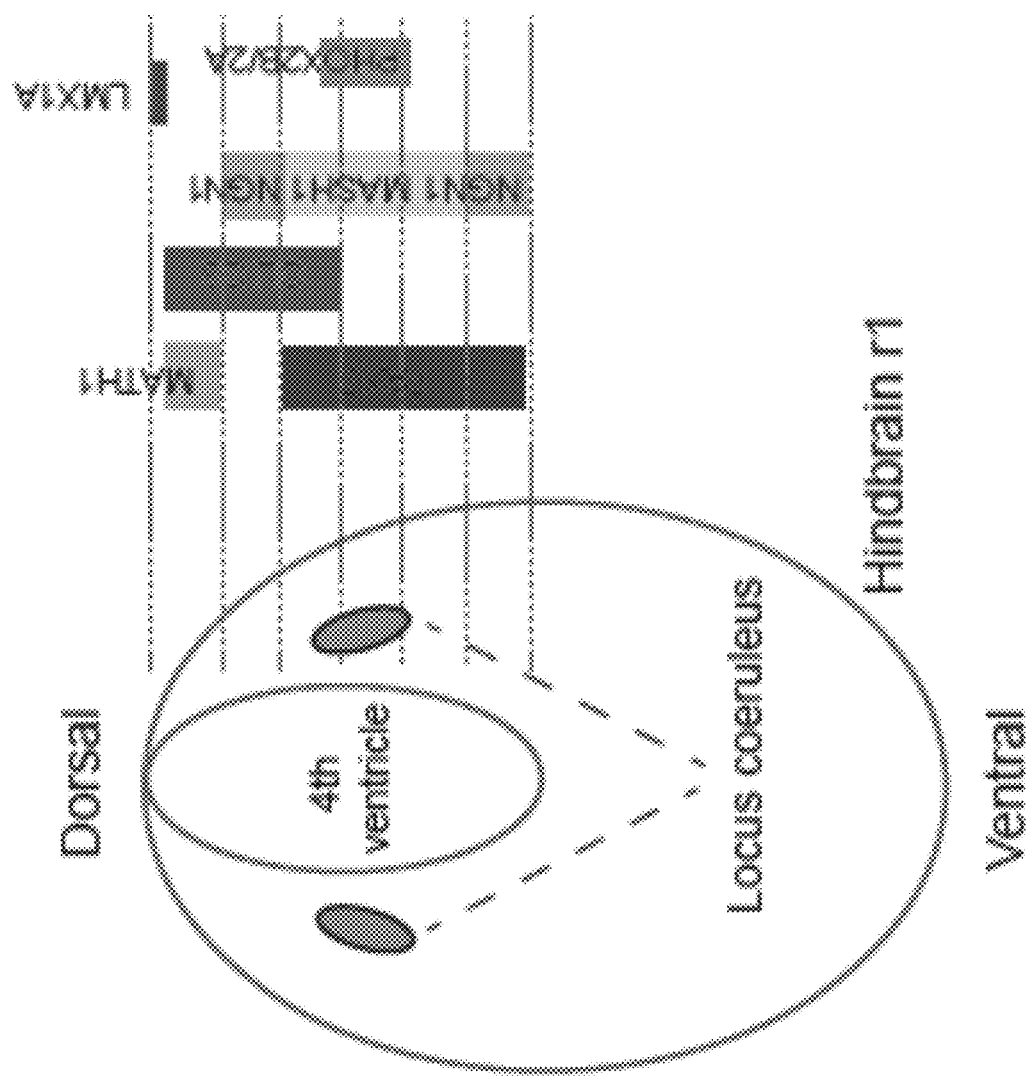
Figure 1F:
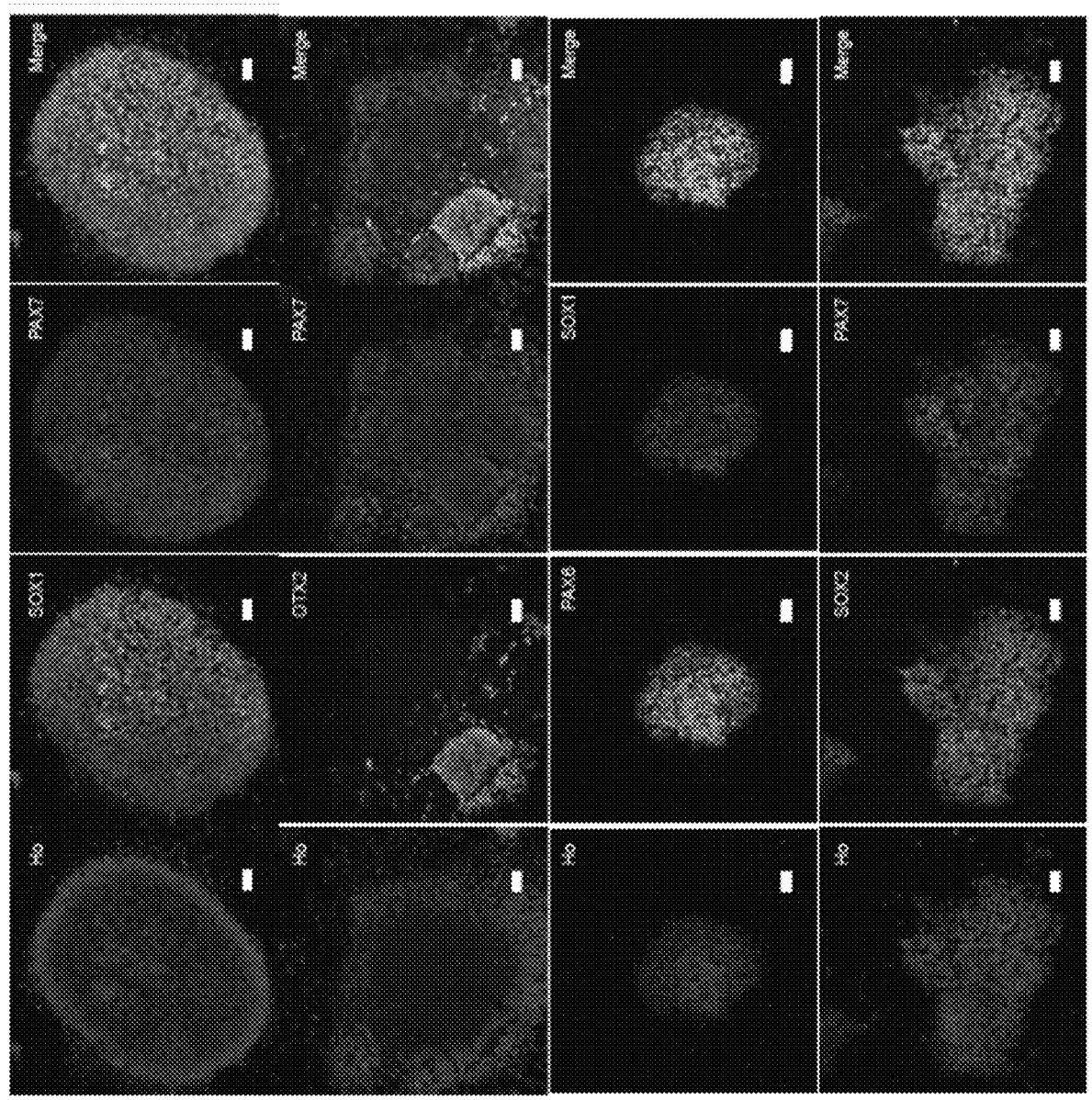
Figure 6A:
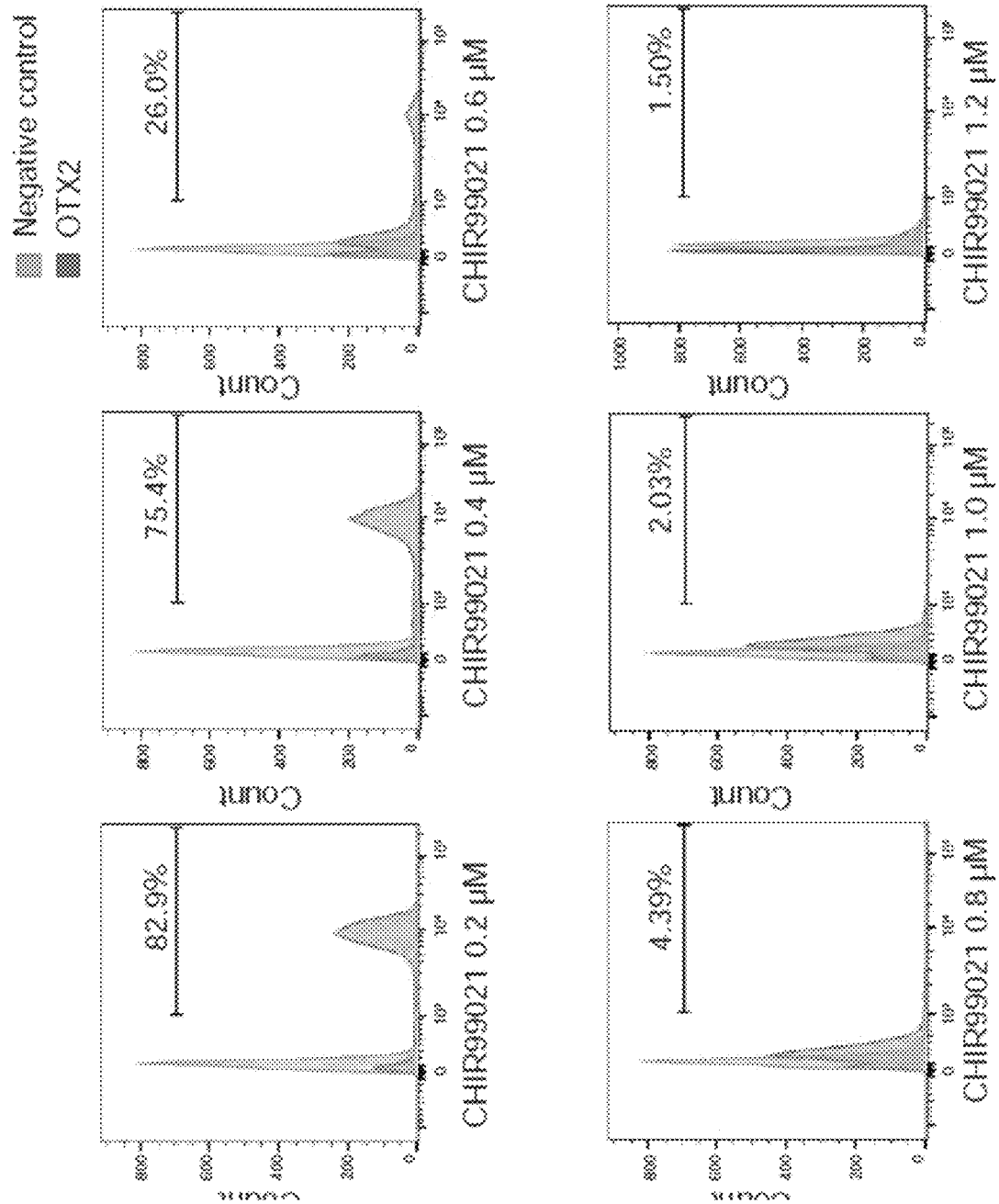
FIGS. 6A-6C.
Figure 6B:
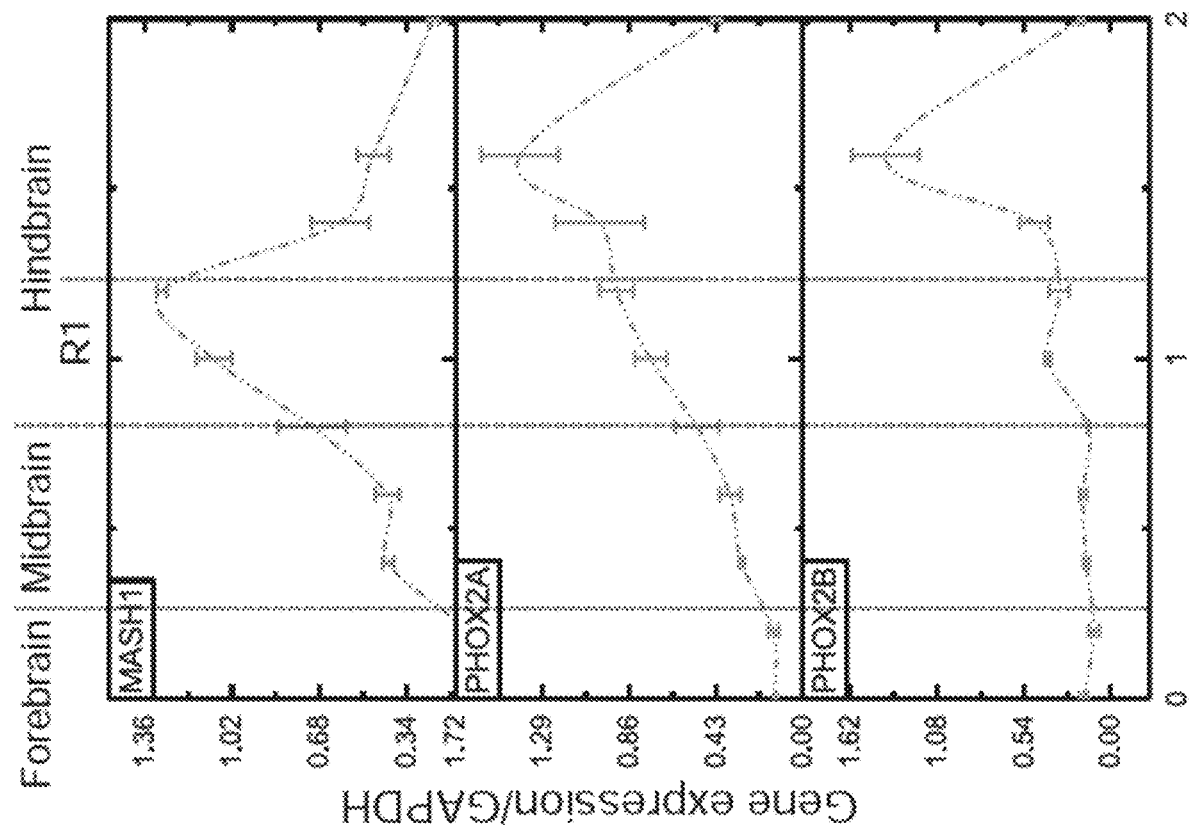
Figure 6C:
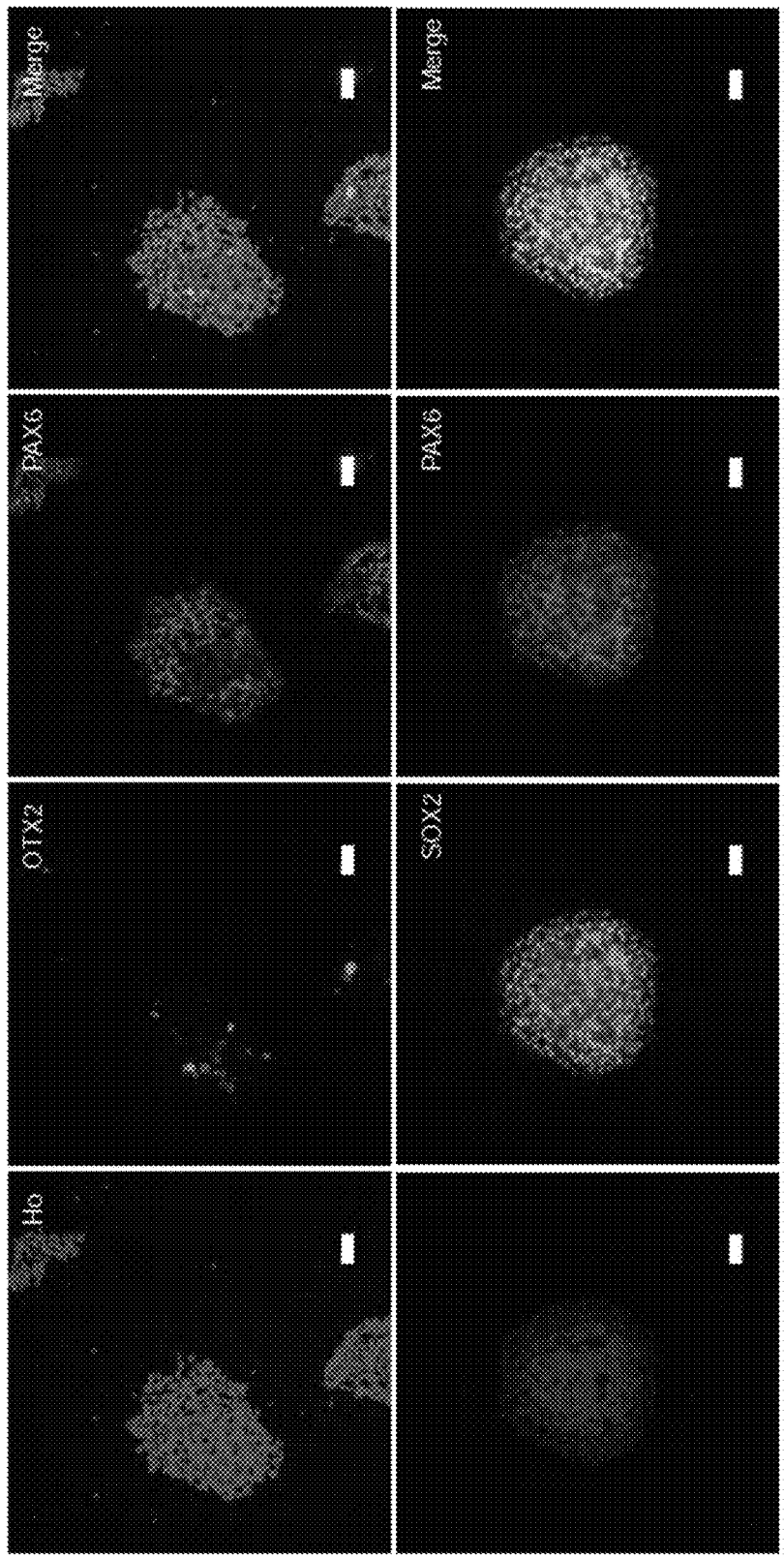

NE neurons in the locus coeruleus (LC) originate from progenitors in the dorsal hindbrain rhombomere 1 (R1) during embryonic development (see Robertson et al., 2013, *Nat Neurosci*, 16:1016-1023) (FIG. 1A). hESCs (H9 line) were differentiated to neuroepithelial cells in the presence of DMH1 (2 µM) and SB431542 (2 µM). Meanwhile, a series of doses of WNT agonist (CHIR99021) was added to specify the neuroepithelial cells to the hindbrain R1 regional identity (FIG. 1B). Progenitors in the R1 segment express EN1/2 and GBX2 but neither OTX2 nor HOXA24. With increasing concentrations of CHIR99012 over 6 days, differentiating cells were found to have down-regulated expression of OTX2, transcription factors expressed in the forebrain and midbrain, at both the mRNA and protein levels, revealed by RT-qPCR and Flow cytometry, respectively (FIG. 1C, FIG. 6A). At the same time, midbrain transcription factor genes, EN1, EN2, and PAX2, were upregulated. At CHIR99021 concentrations above 0.6 µM, these midbrain transcription factor genes began to down-regulate at the mRNA level whereas hindbrain transcription factor genes, HOXA2 and GBX2 showed increased expression (FIG. 1C). NE neural markers PHOX2B and PHOX2A also increased along with the CHIR99021 dose increment and reached their highest level around 1 µM (FIG. 1C). This pattern of gene expression was confirmed by immunocytochemistry, showing expression of EN1 in a majority of the cells, whereas few or no cells were positive for OTX2 and HOXA2 at 1 μM (FIG. 1D, FIG. 6A). Thus, 1 μM CHIR99021 was selected to pattern hindbrain r1 region identity from hPSCs, which matched results of a previous study using 1.4 μM CHIR99021 to pattern Hindbrain R2-R3 region from hPSCs. Lu et al., 2016, *Nat Biotechnol*, 34:89-94.

Figure 1G:
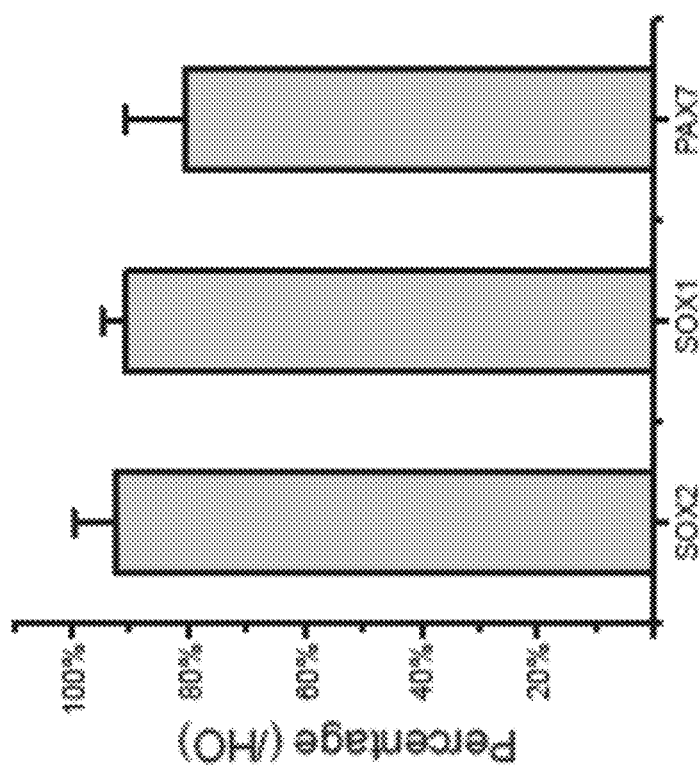

In vivo, locus coeruleus NE neurons are located bilaterally at the 4th ventricle and their progenitors express PAX7 (FIG. 1G). In the experiments disclosed herein, over 80% of the neuroepithelial cells at day 6, identified by SOX1 and SOX2 expression, were also PAX7 positive (FIGS. 1H, 1I). Thus, the neuroepithelial cells at day 6 possessed dorsal hindbrain R1 identity without additional treatment.

Activin A Specified NE Fate in a Region- and Dose-Dependent Manner

Figure 2D:
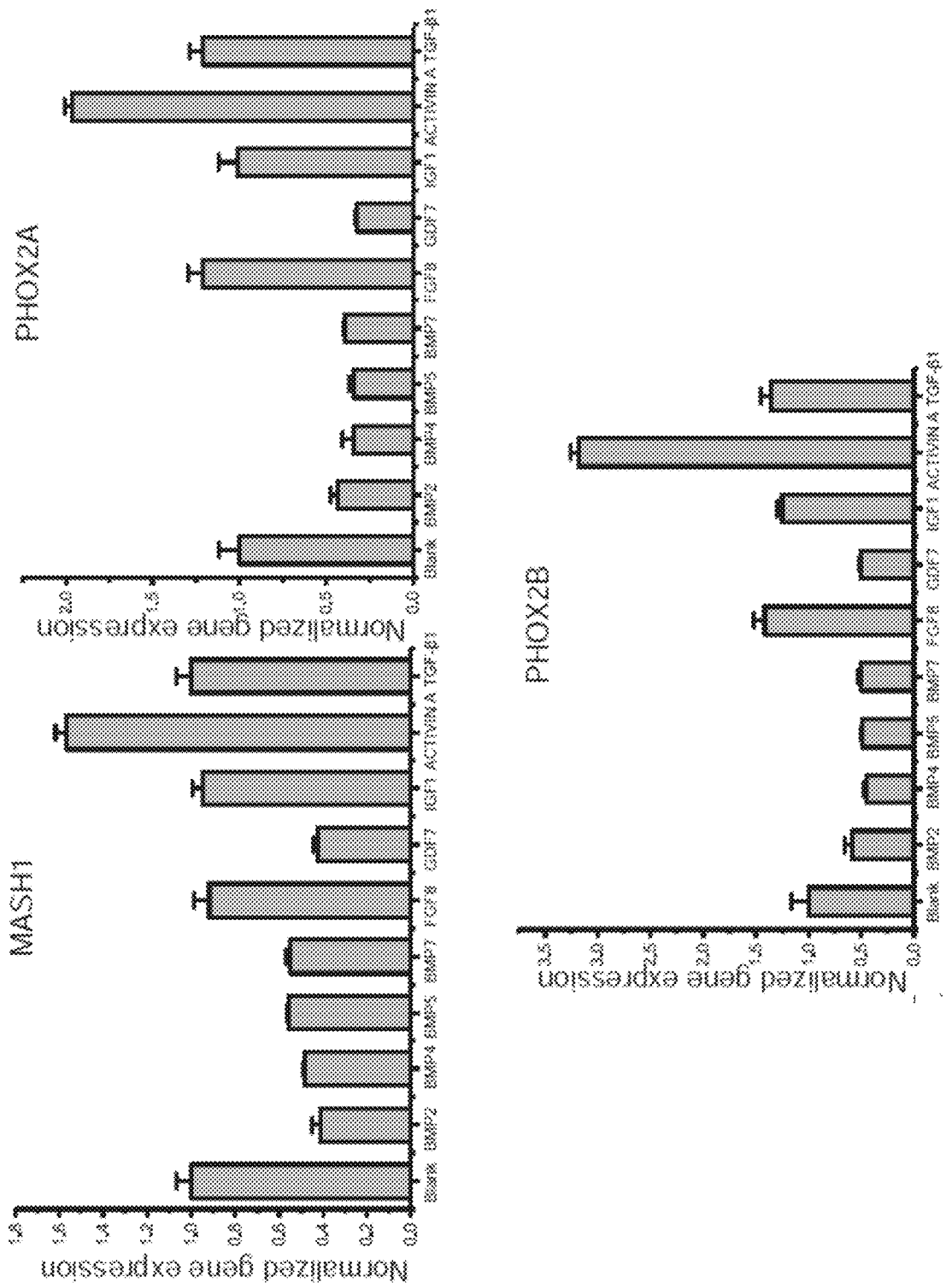
Figure 7A:
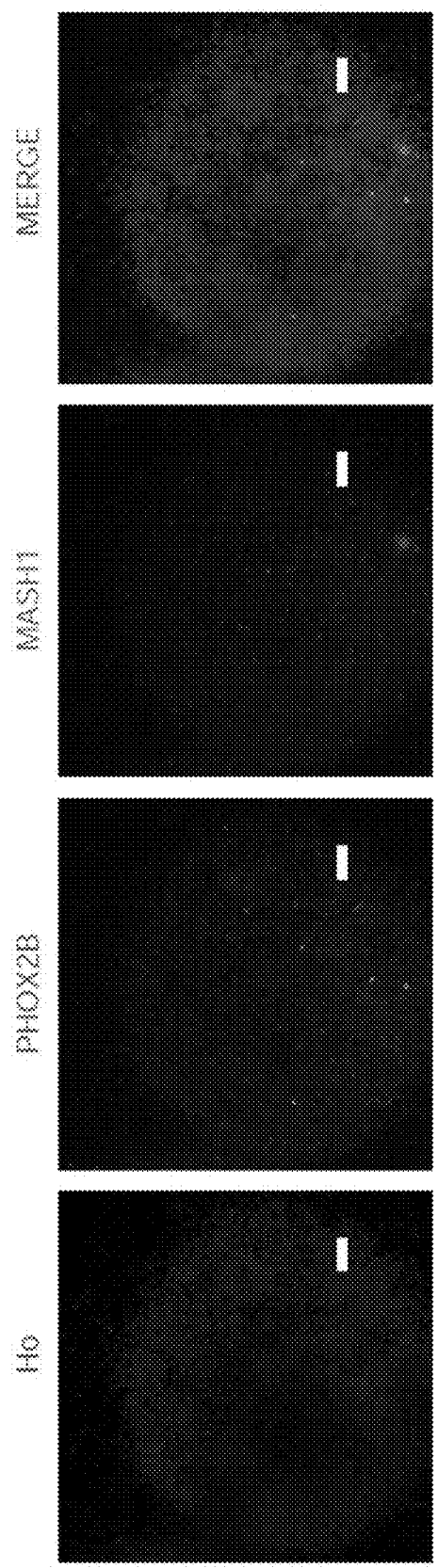
FIGS. 7A-7B.

Development of NE neurons in LC depends on expression of Mash1, Phox2b and Phox2a in a stage dependent manner. See Pattyn et al., 2000, *Mol Cell Neurosci*, 15:235-243; Morin et al., 1997, *Neuron*, 18:411-423; Hirsch et al., 1998, *Development*, 125:599-608. Mash1 is expressed in the proliferative progenitor cells, while Phox2b and Phox2a are expressed when cells became postmitotic precursors and neurons. Pattyn al., 2000. Immunocytochemical analysis of dorsal hindbrain R1 progenitors indicated that very few cells (<1%) were positive for MASH1, PHOX2B and PHOX2A (FIG. 2A, FIG. 7A), suggesting that additional signals can be required for NE fate specification. In zebrafish, FGF8 and BMPs are essential for NE differentiation 9 (FIG. 2A). Thus, the effects of FGF8 and BMPs were tested in the second week of differentiation (FIG. 2B). Treatment of hindbrain R1 neuroepithelial cells from day 6 to day 12 with 100 ng/ml FGF8, or 10 ng/ml BMP2, 4, 5, and 7, or 10 ng/ml GDF7 had no obvious effects on expression of MASH1, PHOX2B, and PHOX2A (FIG. 2D). To the contrary, BMPs and GDF7 decreased expression of MASH1, PHOX2B, and PHOX2A, suggesting that these compounds can inhibit NE neuron fate specification. Increased expression of dorsal transcription factor genes (OLIG3 and MATH1) by BMPs (FIG. 7B) was observed, suggesting that the inhibitory role of BMPs can be due to their dorsalization effect on the progenitors. Ligands in TGF-β pathway were examined and found that Activin A (10 ng/ml) but not TGF-β1 (10 ng/ml) had a positive effect on expression of MASH1, PHOX2B, and PHOX2A (FIG. 2D), suggesting a unique role of Activin A in human NE neuron specification.

Figure 2F:
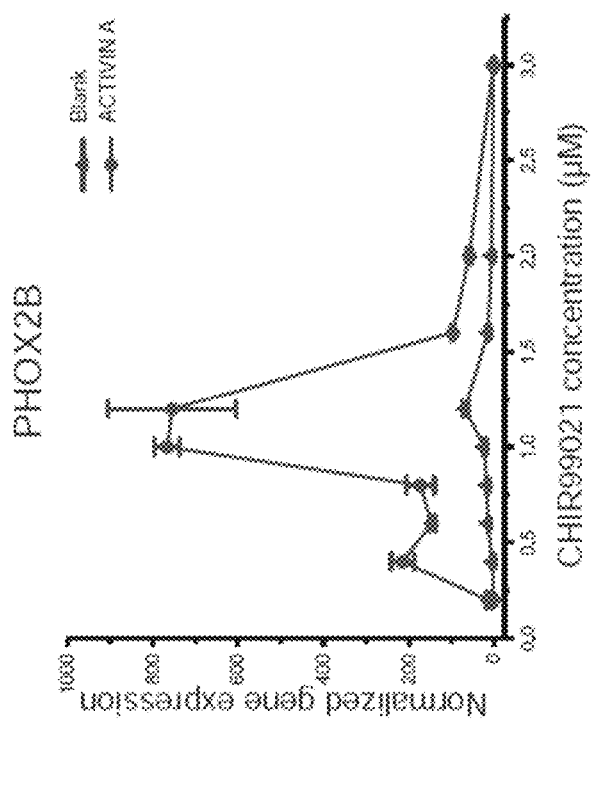
Figure 8A:
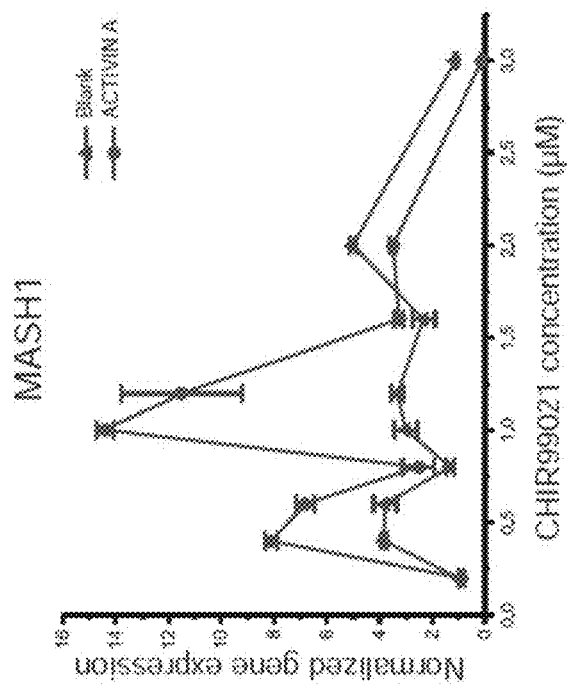
FIGS. 8A-8C.
Figure 8B:
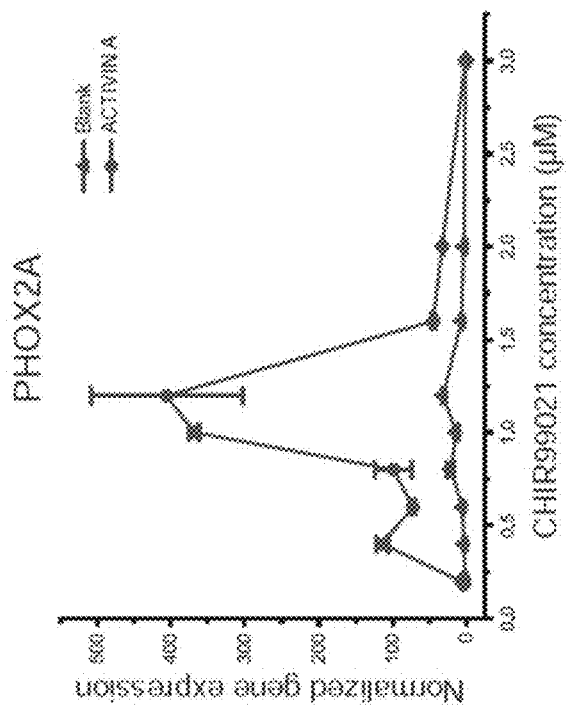

The dose effect of Activin A was examined and Activin A was found to increase expression of MASH1, PHOX2B, and PHOX2A in a dose-dependent manner. MASH1 reached a maximum expression level when 25 ng/ml of Activin A was used while PHOX2B and PHOX2A reached their maximum level when Activin A concentration reached 250 ng/ml (FIG. 2E). This patterning effect of Activin A on expression of MASH1 vs. PHOX2B/PHOX2A suggested that a high concentration (100-250 ng/ml) Activin A boosts MASH1$^+$ progenitor cells to enter postmitotic stage where the cells express PHOX2B or PHOX2A. At day 12, immunostaining for MASH1, PHOX2B and PHOX2A expression revealed that a large portion of cells differentiated in this manner were positive for MASH1, PHOX2B and PHOX2A (FIGS. 2F, FIGS. 8A-8B).

Figure 2G:
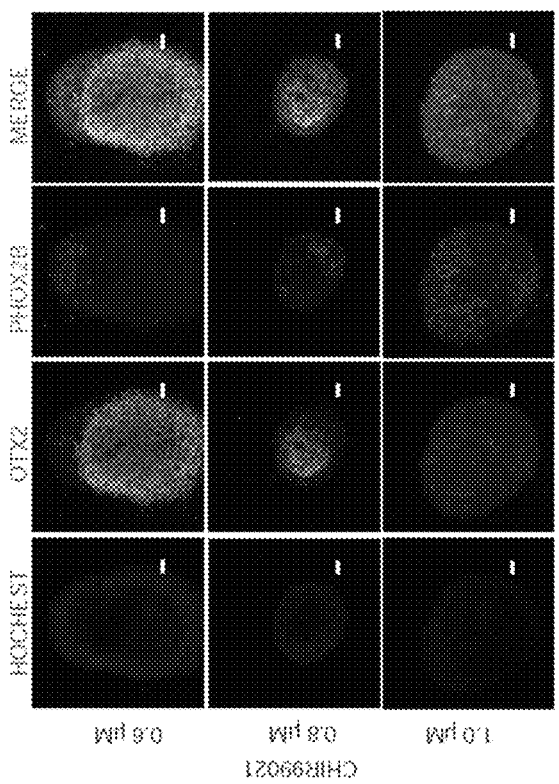
Figure 8C:
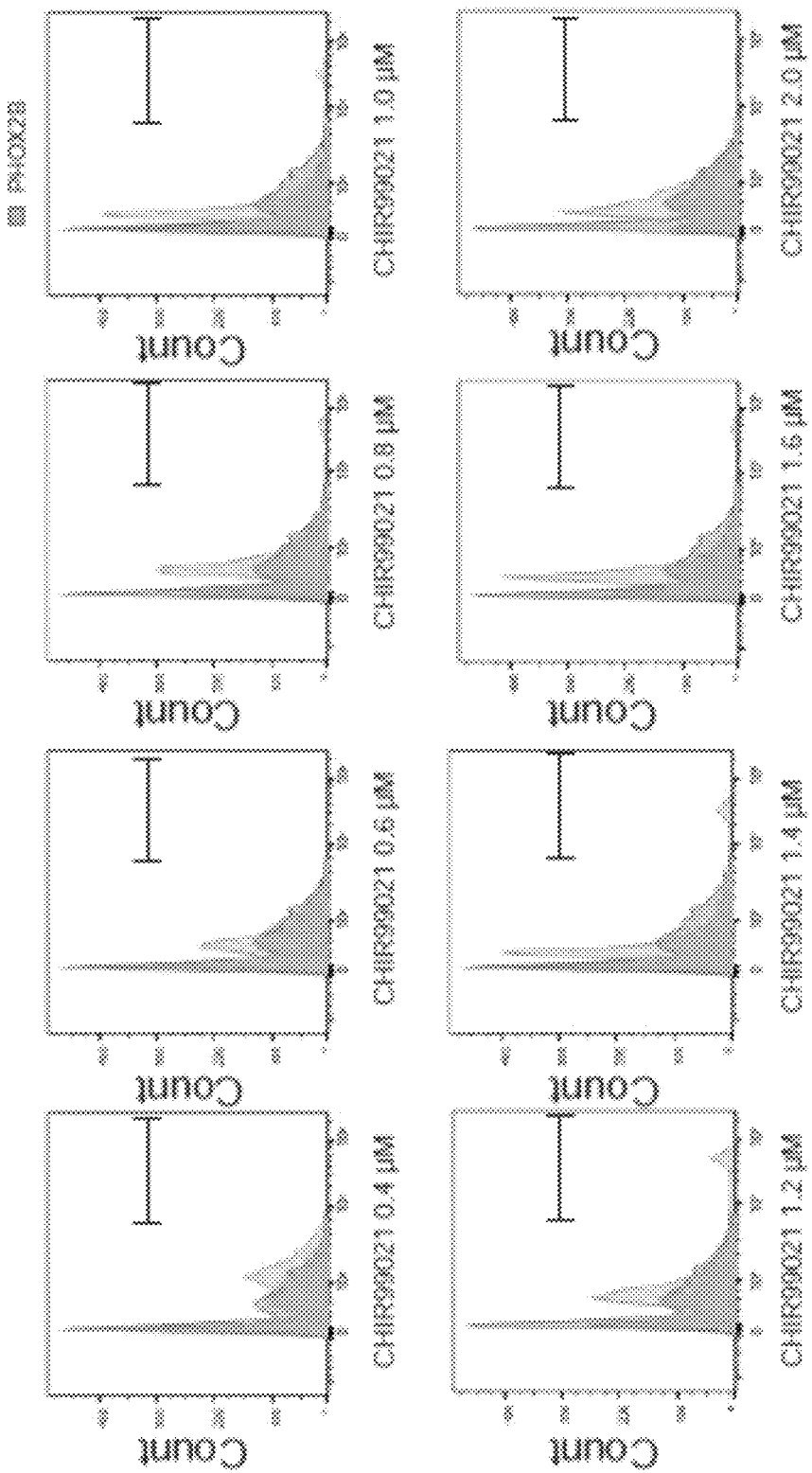

In further experiments it was determined whether the unique role of Activin A on human NE neuron specification was regional identity dependent. Neuroepithelial cells ranging from anterior forebrain to posterior hindbrain were obtained using different doses of CHIR99021, and then these neuroepithelial cells were treated with 25 ng/ml Activin A for 6 days. Only cells having rostral hindbrain identity ("hindbrain R1 neuroepithelial cells"), i.e., those treated with CHIR99021 from 1.0 to 1.4 μM, exhibited the highest level of PHOX2B expression as well as MASH1 and PHOX2A (FIGS. 2G-2H, FIG. 8C). Immunostaining showed that MASH1, PHOX2B and PHOX2A positive cells were all OTX2 negative (FIG. 8D), indicating NE fate could only be specified in cells where OTX2 expression was absent. These results were confirmed by flow cytometry analysis of PHOX2B expression in cells treated with Activin A after patterning by different CHIR99021 concentration (FIG. 8E). Together, these results suggested that Activin A acts on dorsal R1 progenitors to specify NE identity.

Optimization of NE Specification by Activin A

Figure 3A:
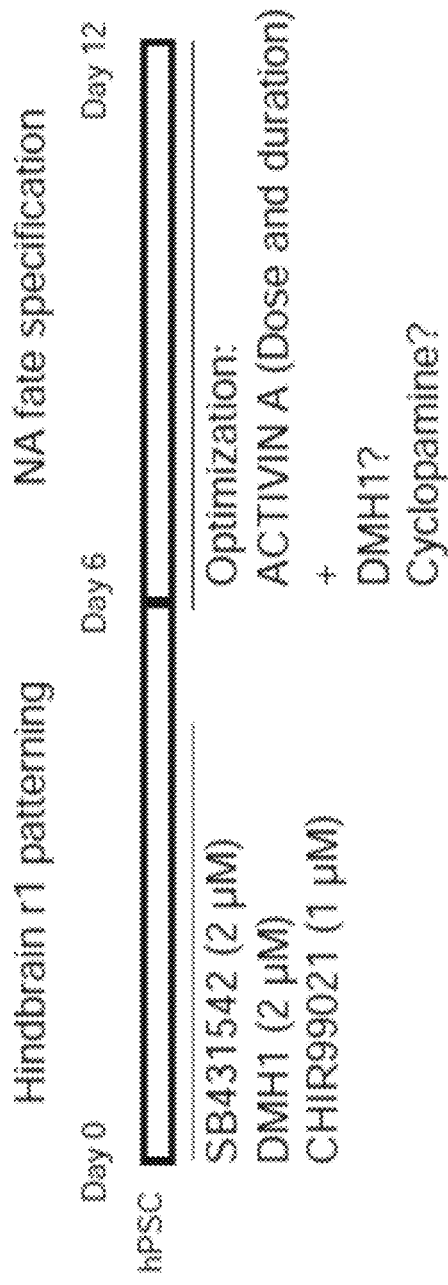
Figure 3B:
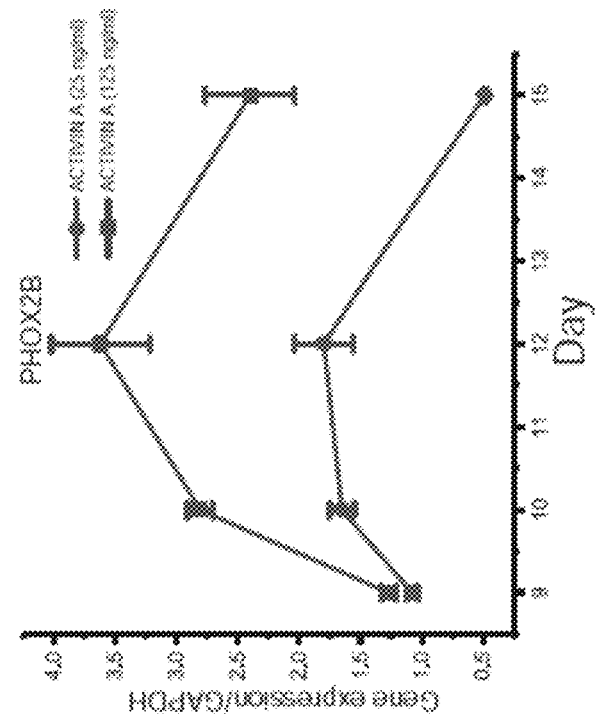
Figure 3C:
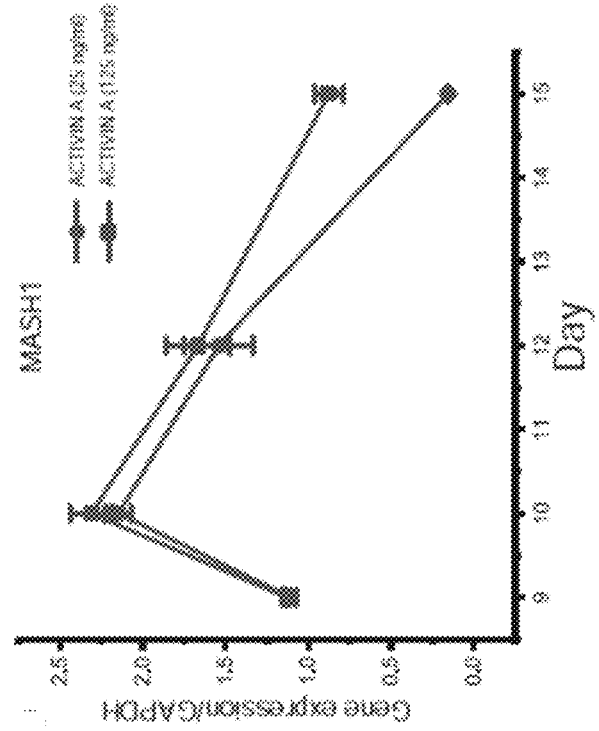
Figure 3F:
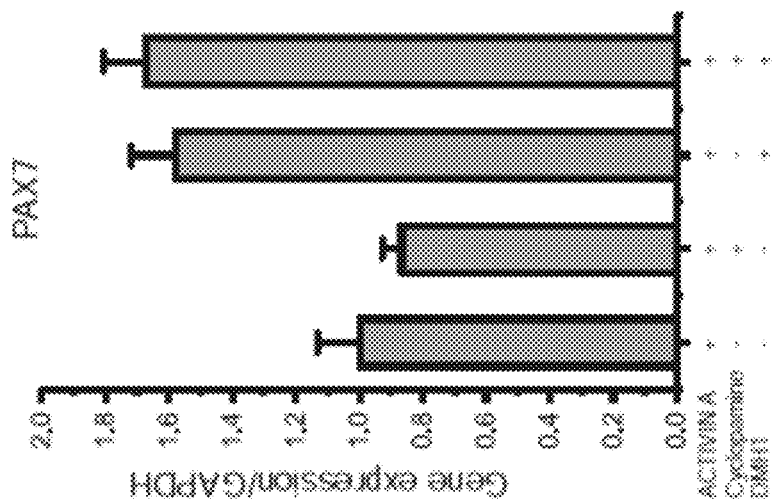

Because a different dose-dependent pattern of MASH1 and PHOX2A/2B was observed when using a higher concentration of Activin A, causing MASH1+ cells to become PHOX2A/2B+ cells, the timing and doses of Activin A required during the second week of differentiation was investigated for maximal induction of MASH1 and PHOX2A/2B (FIG. 3A). Specifically, gene expression of MASH1 and PHOX2A/2B at different times was observed when NE progenitors were cultured in the presence of a low dose of Activin A (25 ng/ml) or a high dose of Activin A (125 ng/ml). There was no obvious difference in MASH1 expression from day 9 to day 12 (FIG. 3B). PHOX2B was expressed at higher levels under high Activin A dose conditions after day 9 and peaked at day 12. Expression was over 2-fold higher under high dose conditions at day 12, but levels were similar at day 9. These data suggested that low Activin A doses were sufficient for days 6 through 9 of culture to maximize MASH1 expression, but high doses were required for days 9 through 12 to maximize PHOX2B expression.

Figure 7B:
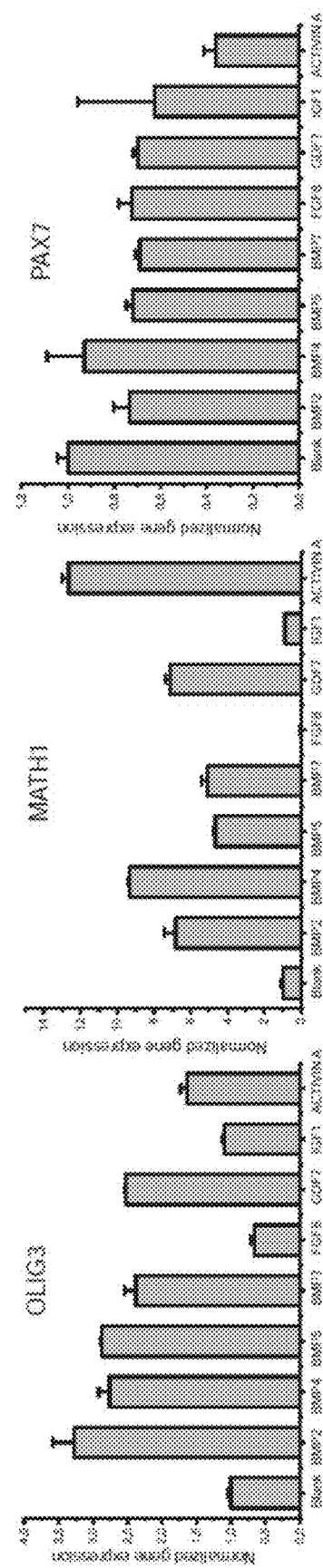

Besides the dose and timing of Activin A administration, high BMP signal activity negatively regulated NE fate specification (FIG. 2D, FIG. 7B). To determine whether blockade of BMP pathway or SHH pathway could facilitate NE specification, which could narrow the domain along the dorsal to ventral axis, hindbrain R1 neuroepithelial cells were treated with Activin A with or without BMP and SHH antagonist (FIGS. 3D-3I). Treating with the SHH antagonist cyclopamine (2 μM) had only minor effects on NE progenitor markers MASH1 (FIG. 3G) and PHOX2A/2B (FIGS. 3H, 3I), but increased expression of dorsal marker MATH1 (FIG. 3D) and OLIG3 (FIG. 3E) as expected. Meanwhile, treating with BMP antagonist DMH1 (2 μM) significantly increased NE progenitor markers (FIGS. 3G-3I) by 1.5-fold.

Immunostaining for differentiating cells between day 9 and day 12 using these conditions exhibited dynamic induction of NE progenitor markers (FIG. 3J). In particular, 90% of cells were MASH1+ at day 9, while 40% MASH1+ and 45% PHOX2B+ cells were observed at day 12.

Generating Mature NE Neurons from hPSCs

Figure 3E:
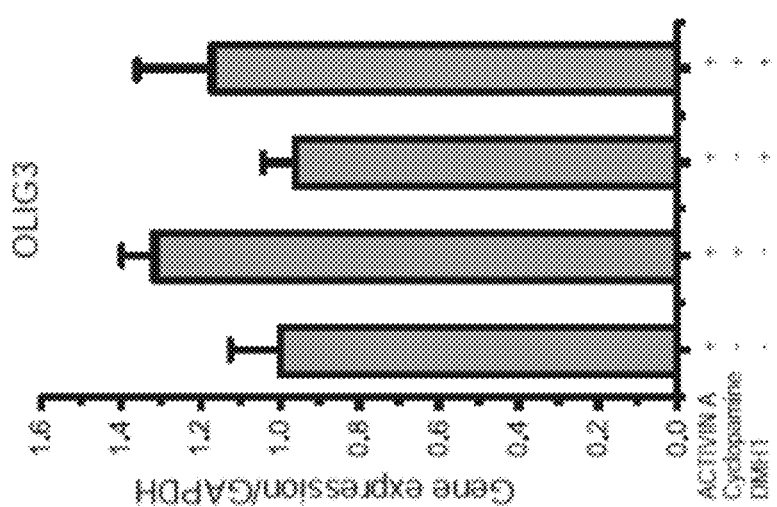
Figure 3D:
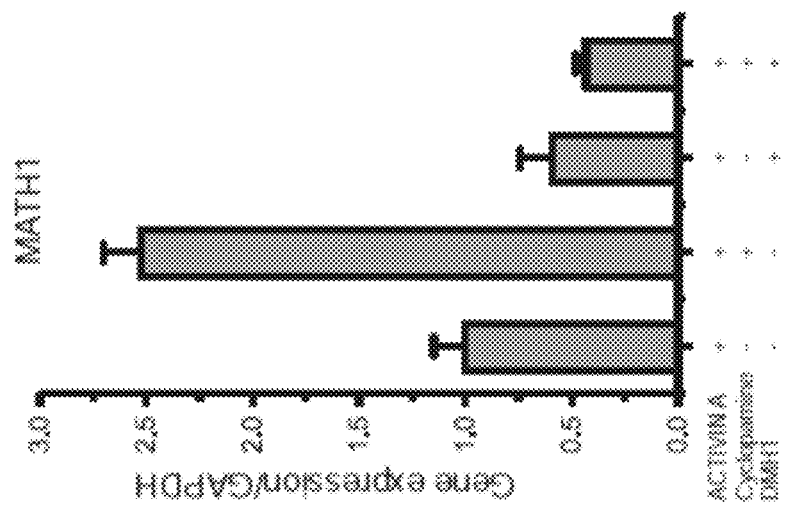
Figure 4D:
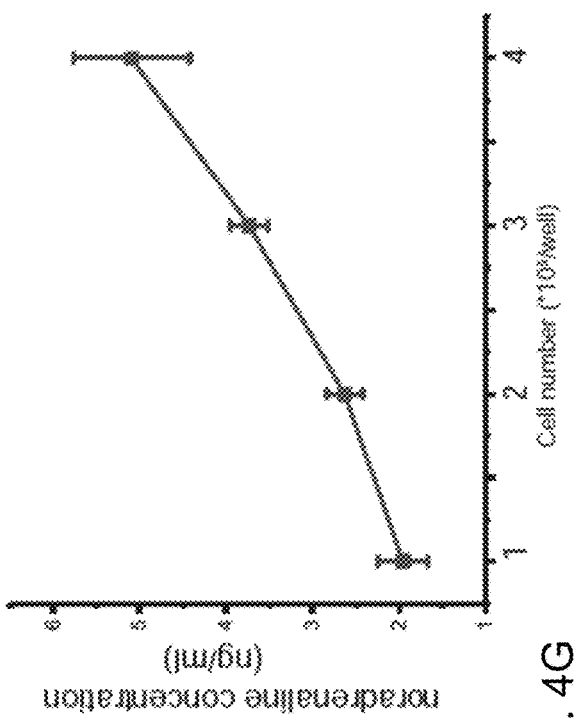
(FIG. 4D) Quantification of PHOX2B and PHOX2B/TH positive cells in culture.
Figure 4E:
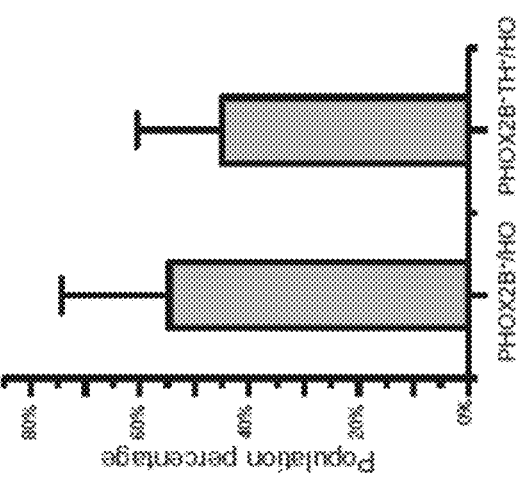
(FIG. 4E) Supernatant norepinephrine concentration from different density of noradrenaline neurons.
Figure 4F:
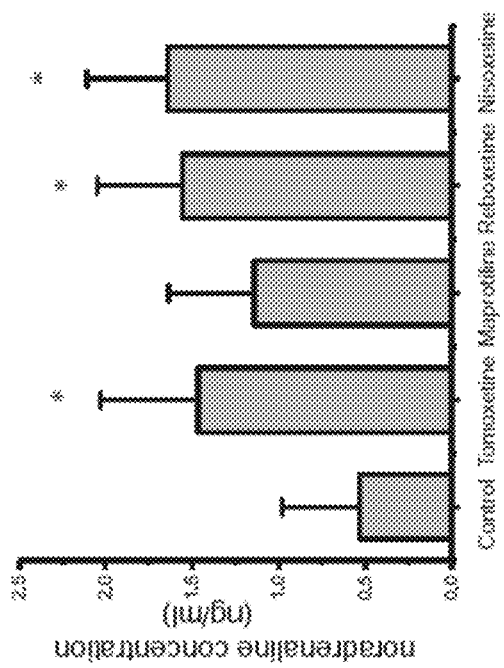
(FIG. 4F) Supernatant norepinephrine release from the neurons during neuronal maturation.
Figure 4G:
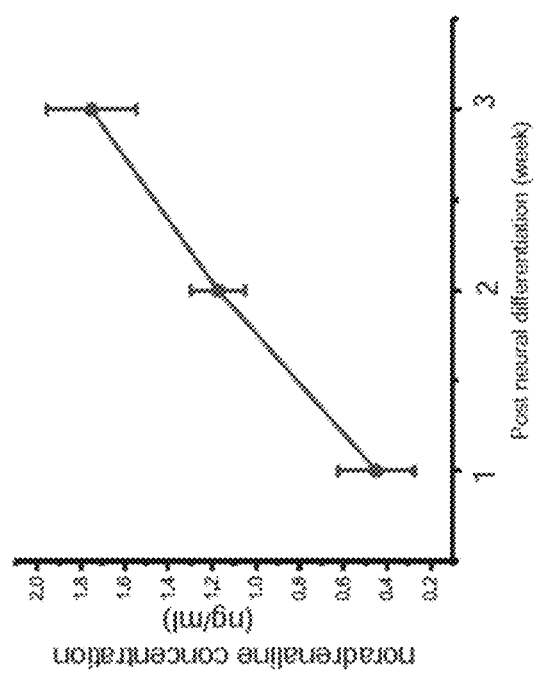
(FIG. 4G) Supernatant norepinephrine content under treatment of norepinephrine reuptake inhibitors.
Figure 4I:
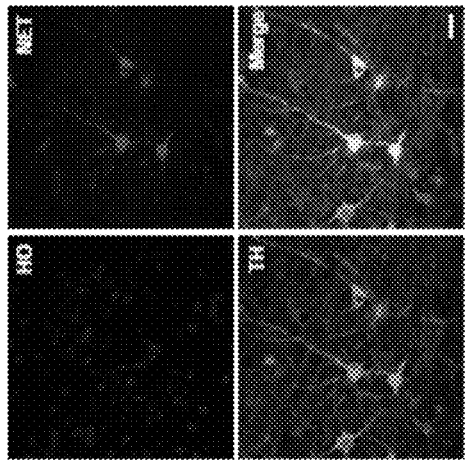
(FIGS. 4I-4L) Immunostaining of NE markers NET, MAO, COMT and ADRA2 in H9 derived NE neurons at day 30. HO, Hoechst. Scale bars, 20 µm.
Figure 9A:
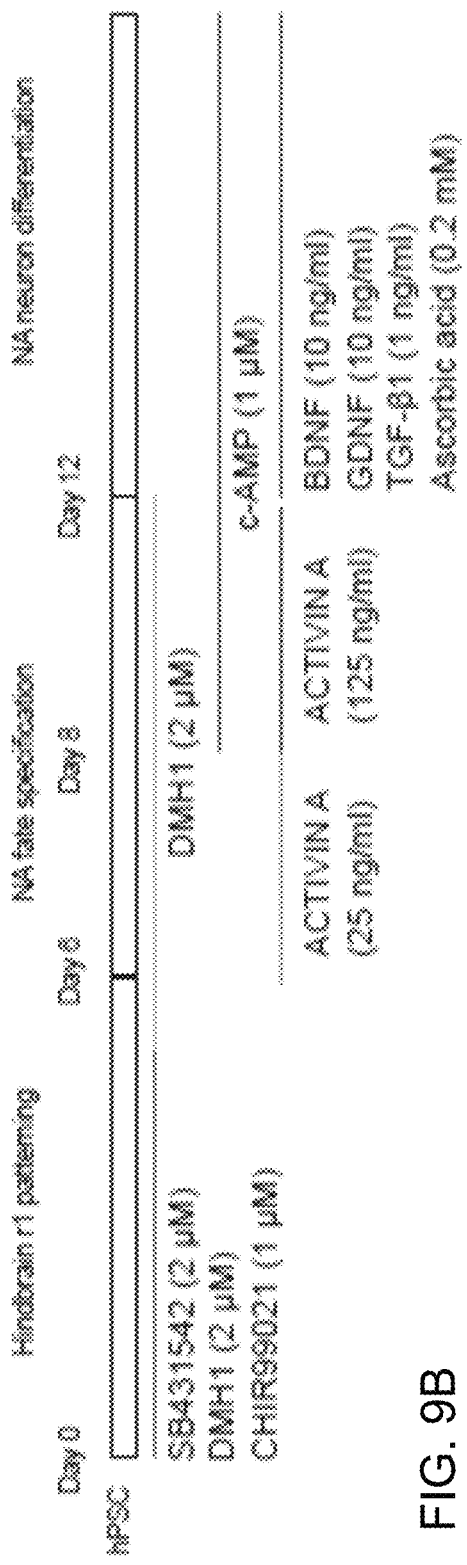
Figure 9B:
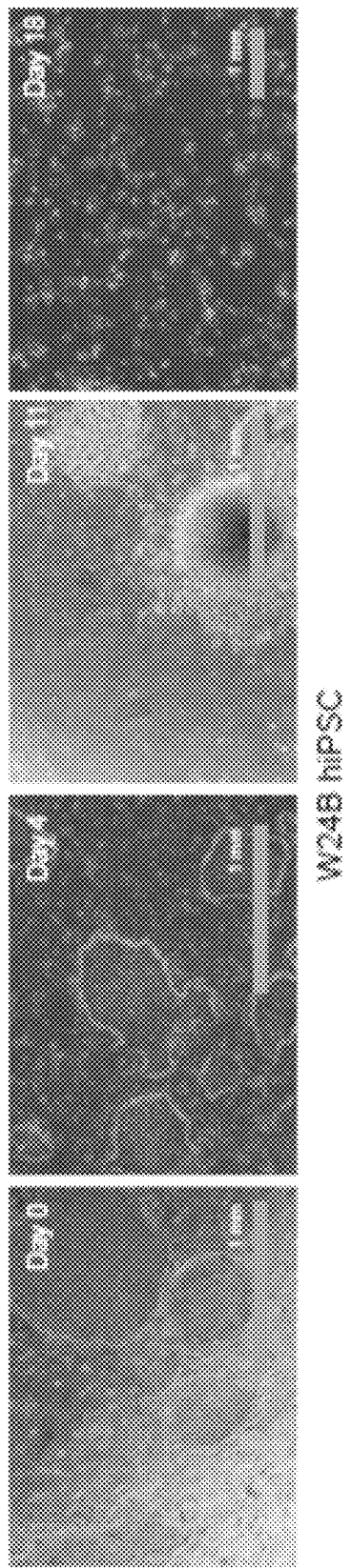
Figures 9C, 9D, 9E:
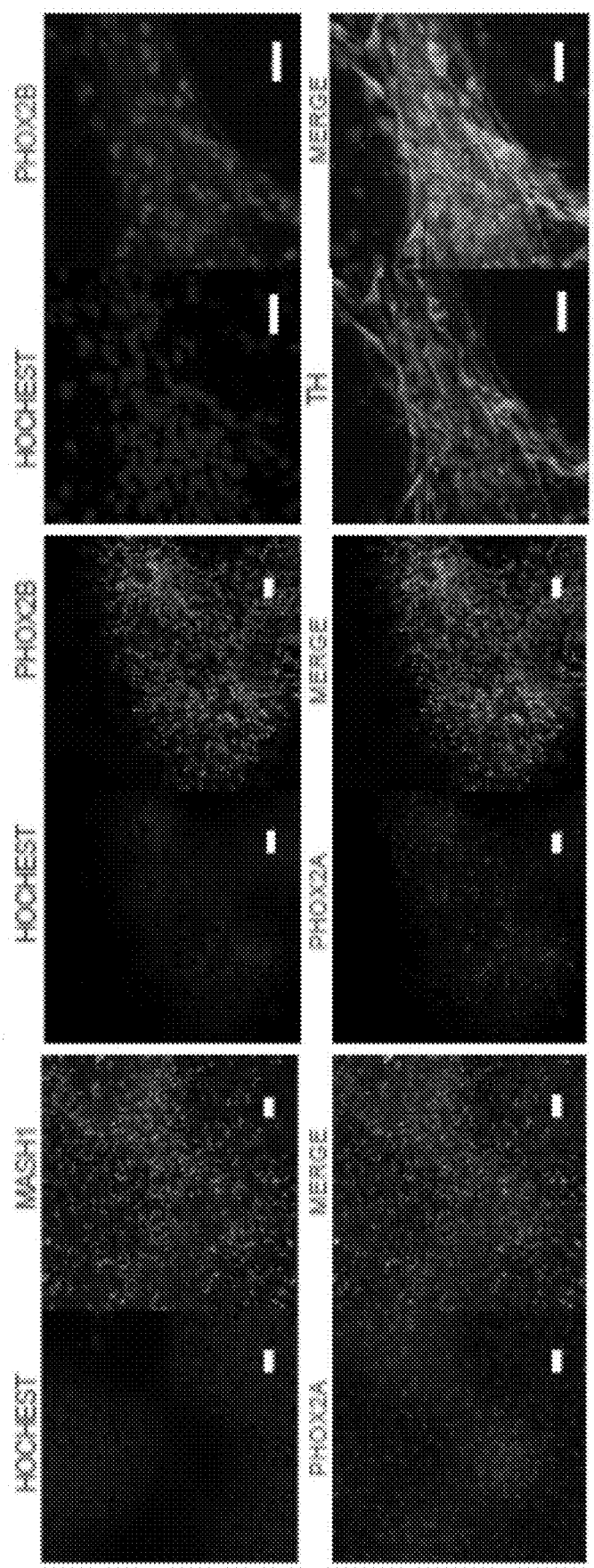

To determine the differentiation potential of the specified NE progenitors, NE progenitor clusters were disrupted and dispersed as single cells at day 12 and then cultured under neuronal differentiation conditions (FIG. 9A). RT-PCR analysis indicated that the expression of tyrosine hydroxylase (TH) and dopamine β-hydroxylase (DBH), the rate-limiting enzymes for synthesizing norepinephrine, increased by 16- and 36-fold from day-6 to day-12, respectively (FIG. 4A). By 18 days of differentiation (from hESCs), immunostaining showed that ~40% of the cells expressed TH and DBH (FIGS. 4B, 4C). The percentage of PHOX2B+/TH+ (double positive cells) was about 45% in the whole culture, while about 55% of the total cells were singly positive for PHOX2B expression (and negative for TH expression) (FIG. 3D). Efficient generation of NE neurons was reproduced using two additional iPSC cell lines, line W24b and line W24M (FIGS. 9C-9H).

Figure 4H:
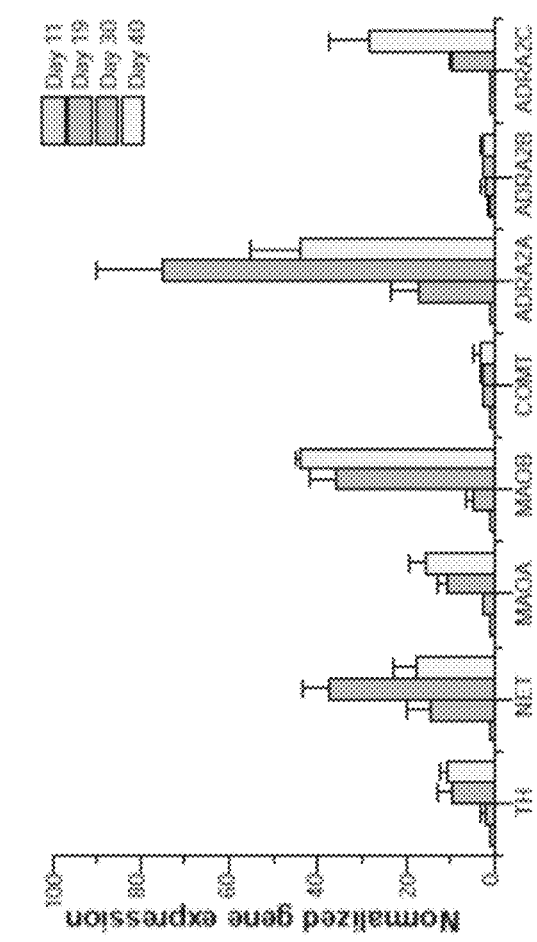
(FIG. 4H) qPCR analysis of gene expression following neuronal differentiation at day 11, 19, 30 and 40. Data are shown as mean±SEM. n=3 for each condition.
Figure 4J:
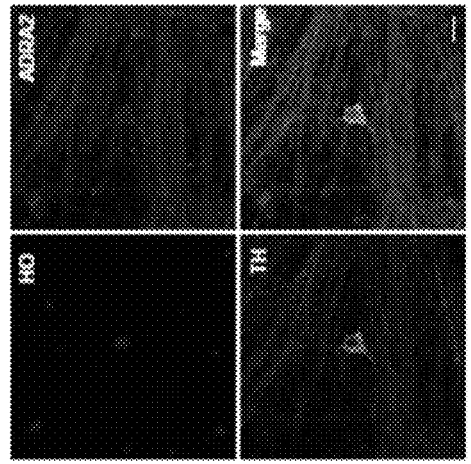
Figure 4K:
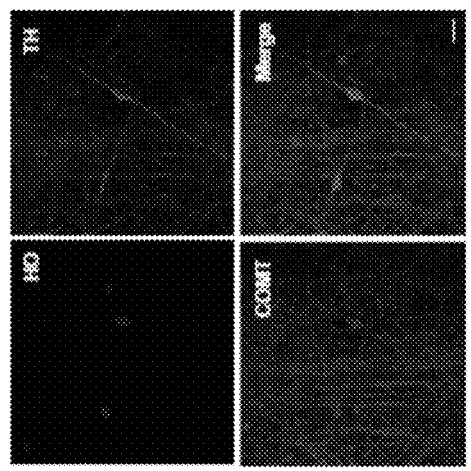
Figure 4L:
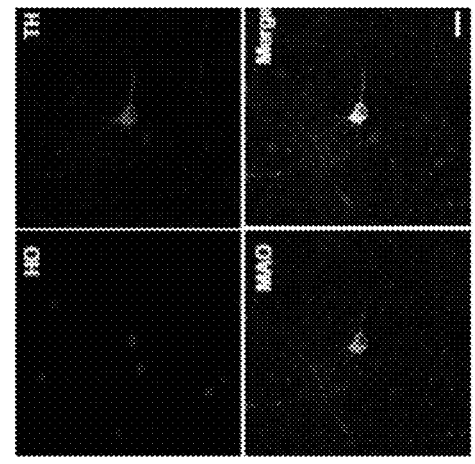

Other NE neuronal markers such as norepinephrine transporter (NET), monoamine oxidase (MAO), catechol-O-methyltransferase (COMT) and adrenoceptor alpha 2A (ADRA2) were upregulated from day 11 to day 40 (FIG. 4H). Their protein expression was confirmed by immunocytochemistry in the NE neurons at day 30 (FIGS. 4I-4L).

Figure 4M:
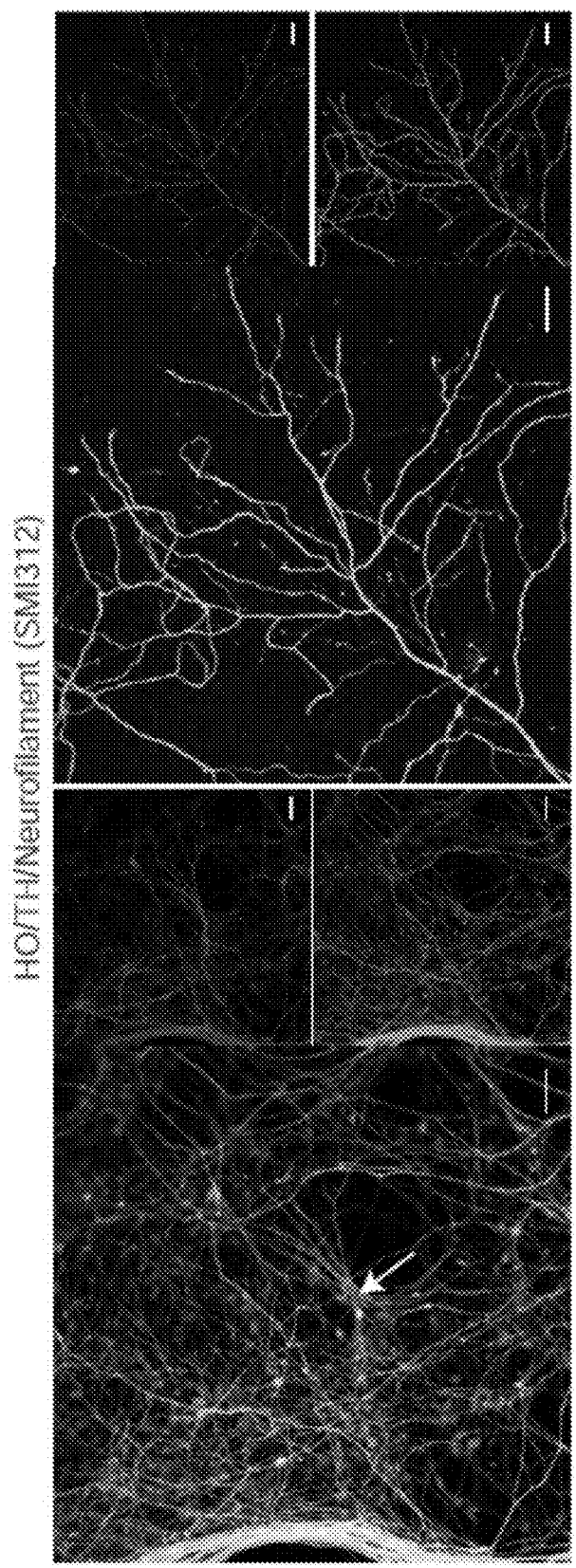
(FIG. 4M) Immunostaining of neurofilament in NE neuron cell body, dendries and axons. The white arrow points to the NE cell body which is not stained by neurofilament (SM312). HO, Hoechst. Scale bars, 50 µm.
Figure 4N:
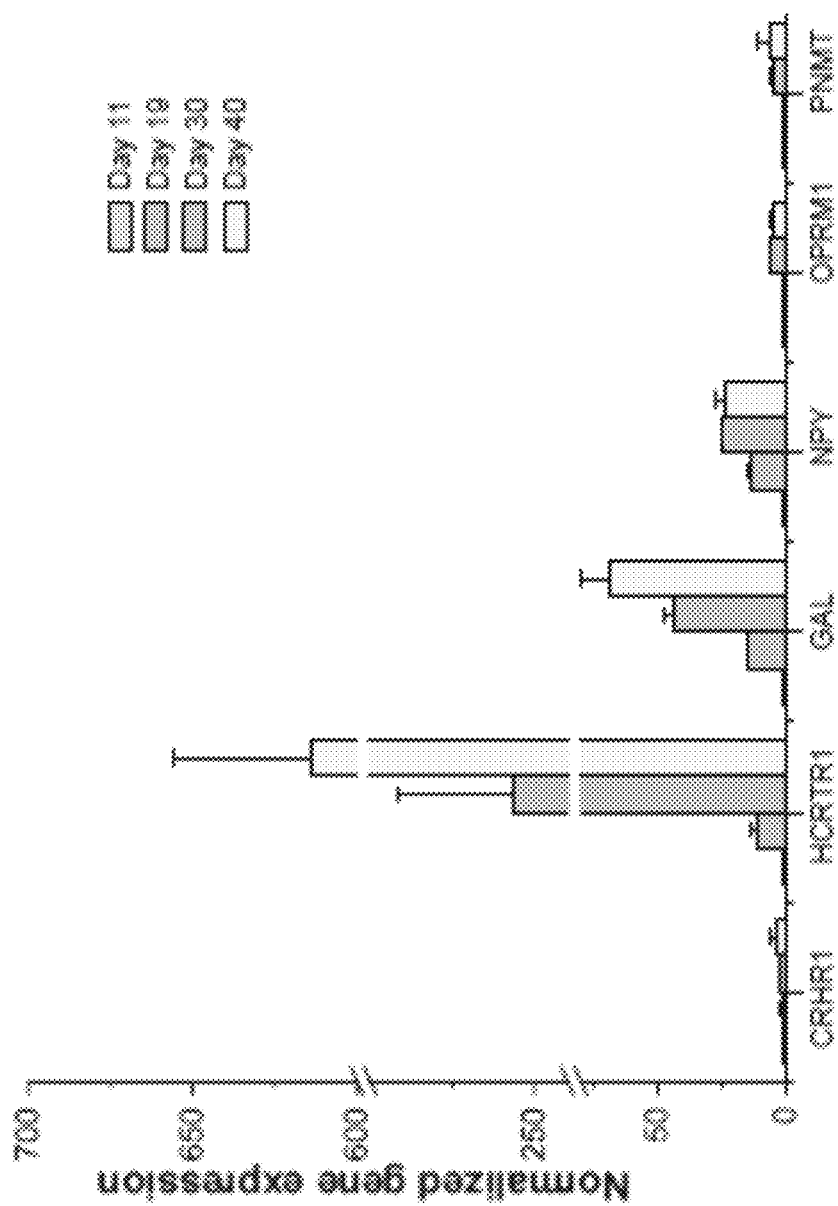
(FIG. 4N) qPCR of gene expression following NE neuronal differentiation at day 11, 19, 30 and 40. Data are shown as mean±SEM. n=3 for each condition.
Figures 4O, 4P:
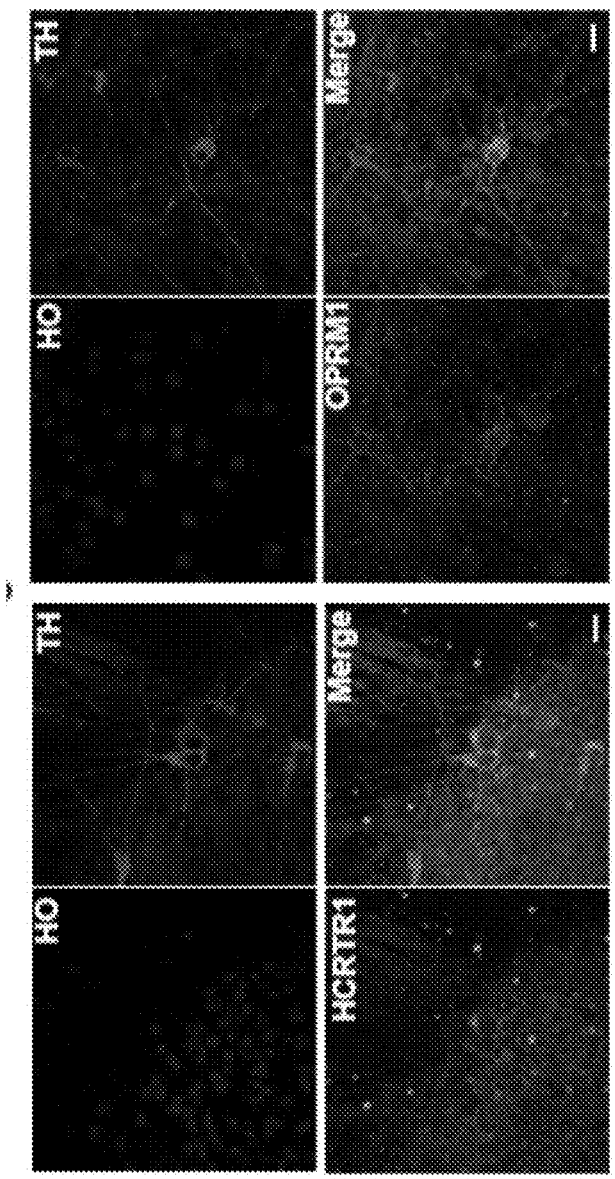
(FIGS. 4O-4P) Immunostaining for HCRT1 and OPRM1 in H9 derived NE neurons at day 30. Scale bars, 20 µm.
Figure 4S:
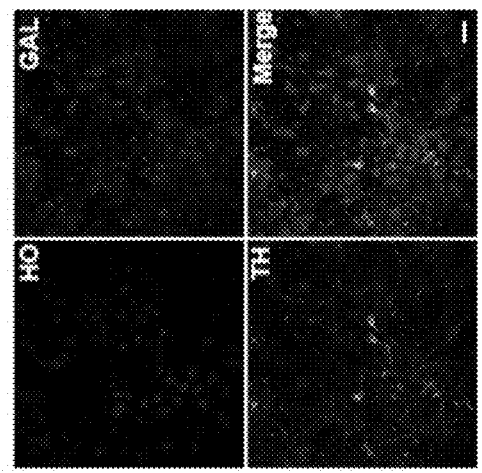
Figure 4R:
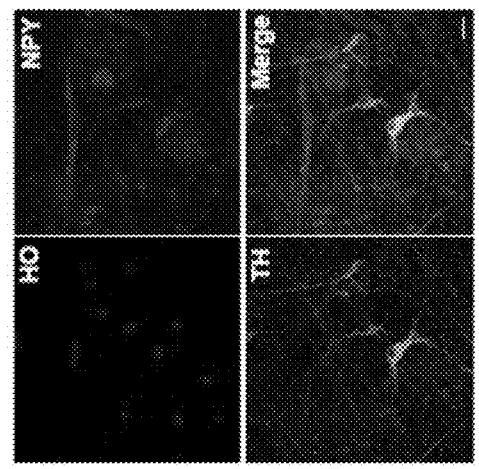
Figure 4Q:
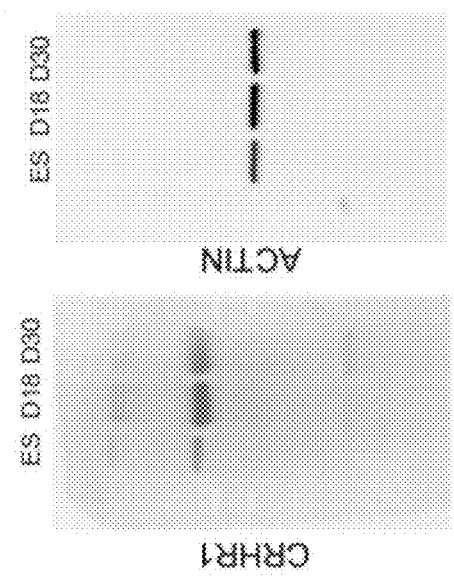
(FIG. 4Q) The expression of CRHR1 by western blot at Day 0 (ES), Day 18 (D18) and Day 30 (D30) along NE differentiation.
Figure 9I:
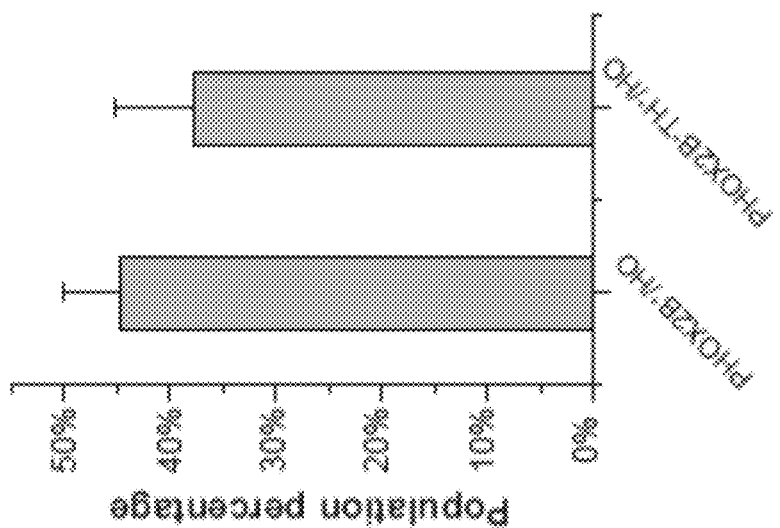
Figure 9J:
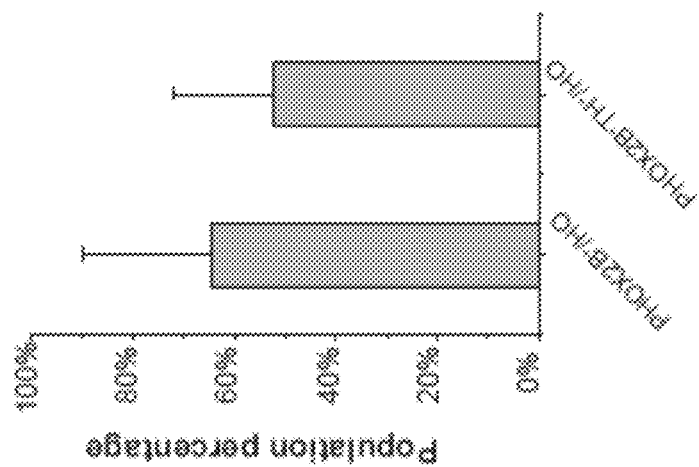

With long term differentiation (2 months), extensive dendrite and axonal branches were present in the NE neurons. The identity of the NE axons was confirmed by their colabeling of TH and SMI312, an antibody specifically labels axons (FIG. 4M). Besides NE neurons, some of the neurons in the cultures were positive for GABA (~5%) and CaMKII or VGLUT1 (~40%) at day 30. Few cells were positive for PNMT (<1%) while no 5-HT neurons were detected (FIGS. 13A-13D). The PNMT positive cells were also observed in iPSC derived NE cultures (FIGS. 9I and 9J).

To evaluate the functional attributes of the NE neurons, NE neurotransmitter content in the supernatant of NE neuron culture was measured by ELISA. NE concentrations increased with the culture period from 1 to 3 weeks after plating (FIG. 3F), suggesting that NE production correlated with neuronal maturation. At 3 weeks post-plating, NE concentration increased with an increasing number of neurons in each culture (FIG. 3E). These results indicated that the hESC-derived NE neurons release NE and its release was activity-dependent.

Figures 3G, 3H, 3I:
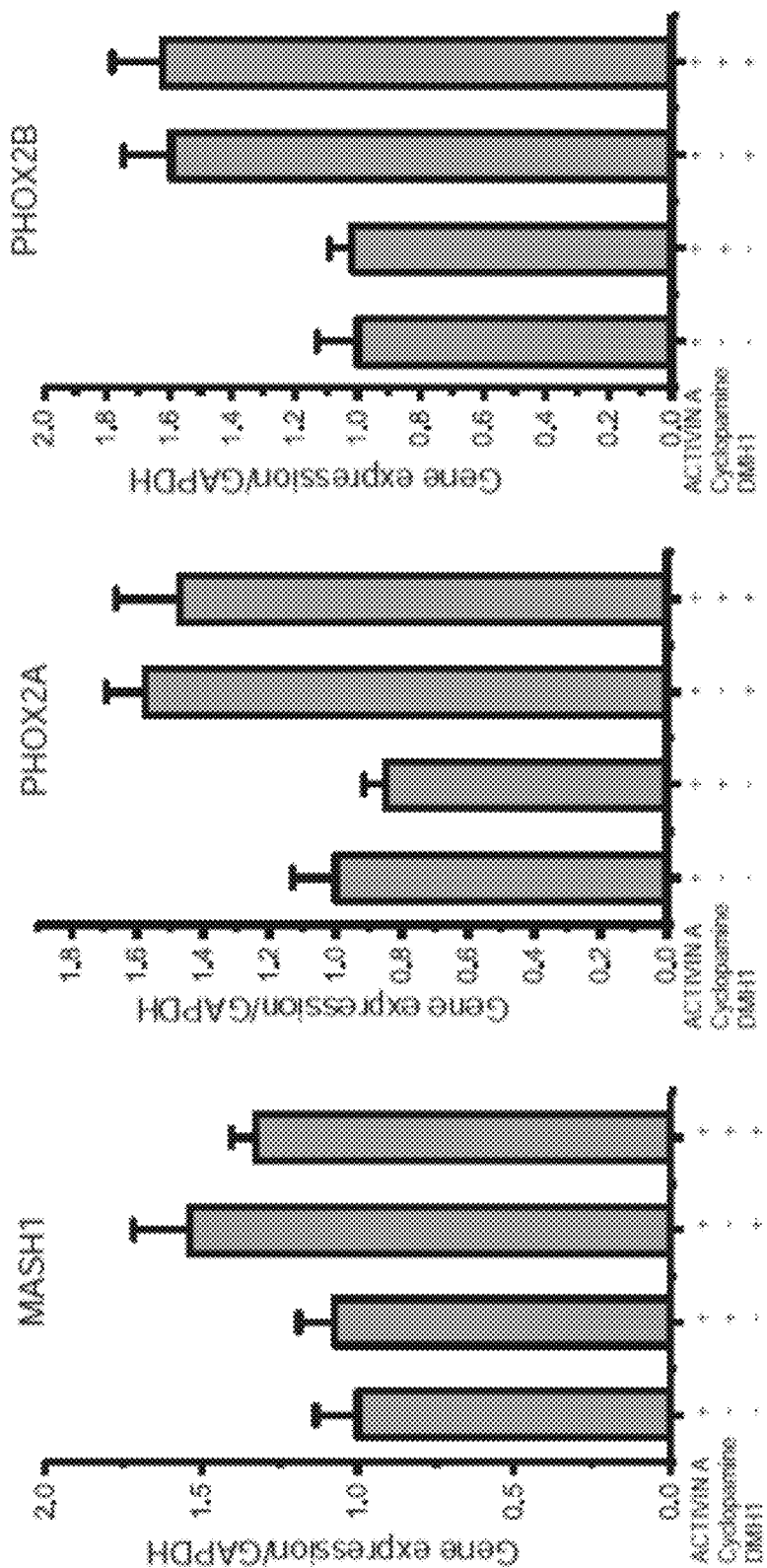

NE reuptake inhibitors were used to examine their effect on NE release. Four NE reuptake inhibitors (Tomoxetine, Maprotiline, Reboxetine and Nisoxetine) were tested in our cells. Tomoxetine, Maprotiline and Reboxetine were FDA-approved drugs and have been used to treat attention deficit hyperactivity disorder (ADHD), depression and anxiety. Treating with NE reuptake inhibitors increased the NE content in the supernatants (FIG. 3G).

Mature NE Neurons Exhibit Chemoreceptor Activity

Figure 11I:
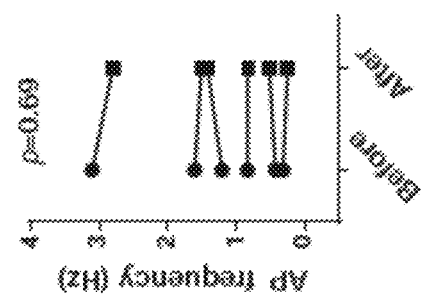
(FIG. 11I) Quantification of the firing rate change in panel H. Data are shown as symbols and lines in the "before-after" pattern. n=7 neurons.
Figure 11H:
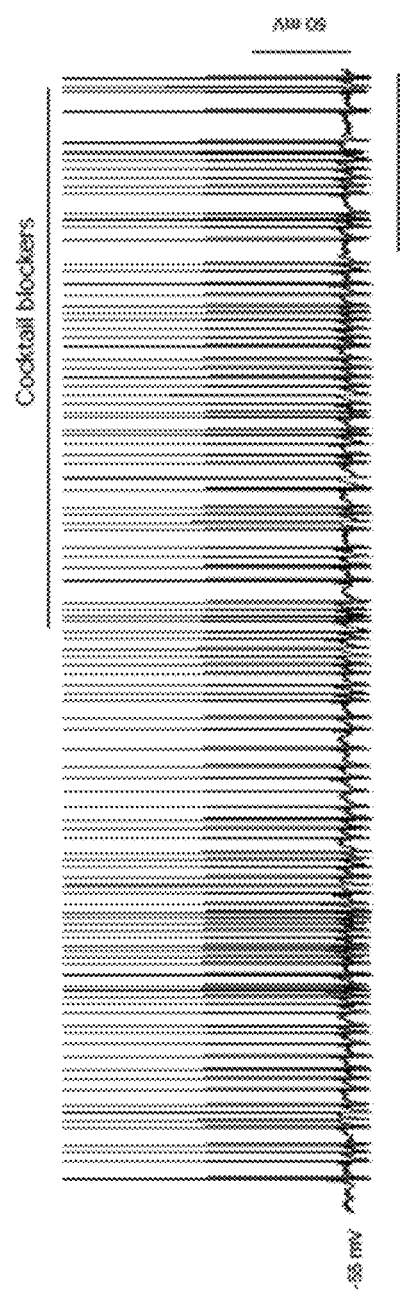
(FIG. 11H) Representative trace of spontaneous firing before, at, and after cocktail blockers.
Figures 12A, 12B:
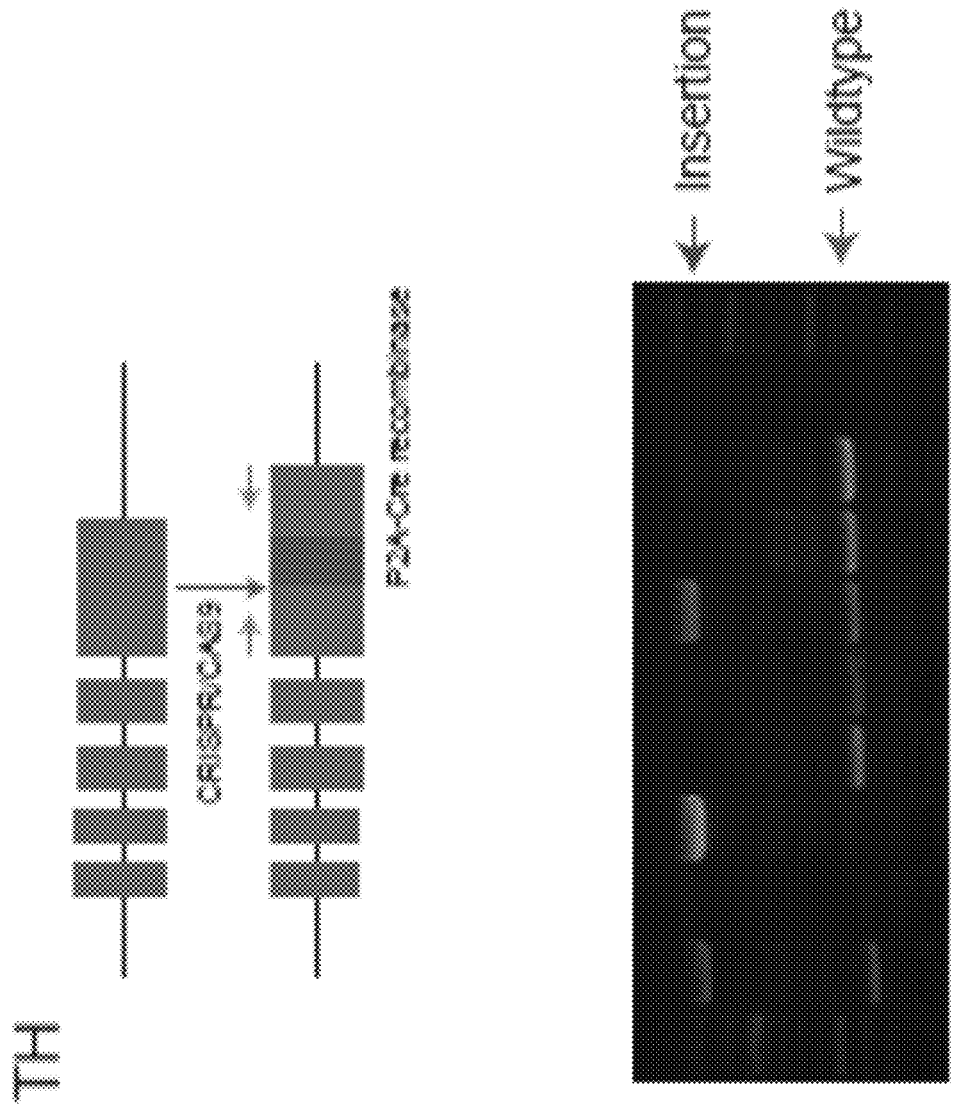
FIGS. 12A-12B.
Figures 13A, 13B, 13C, 13D:
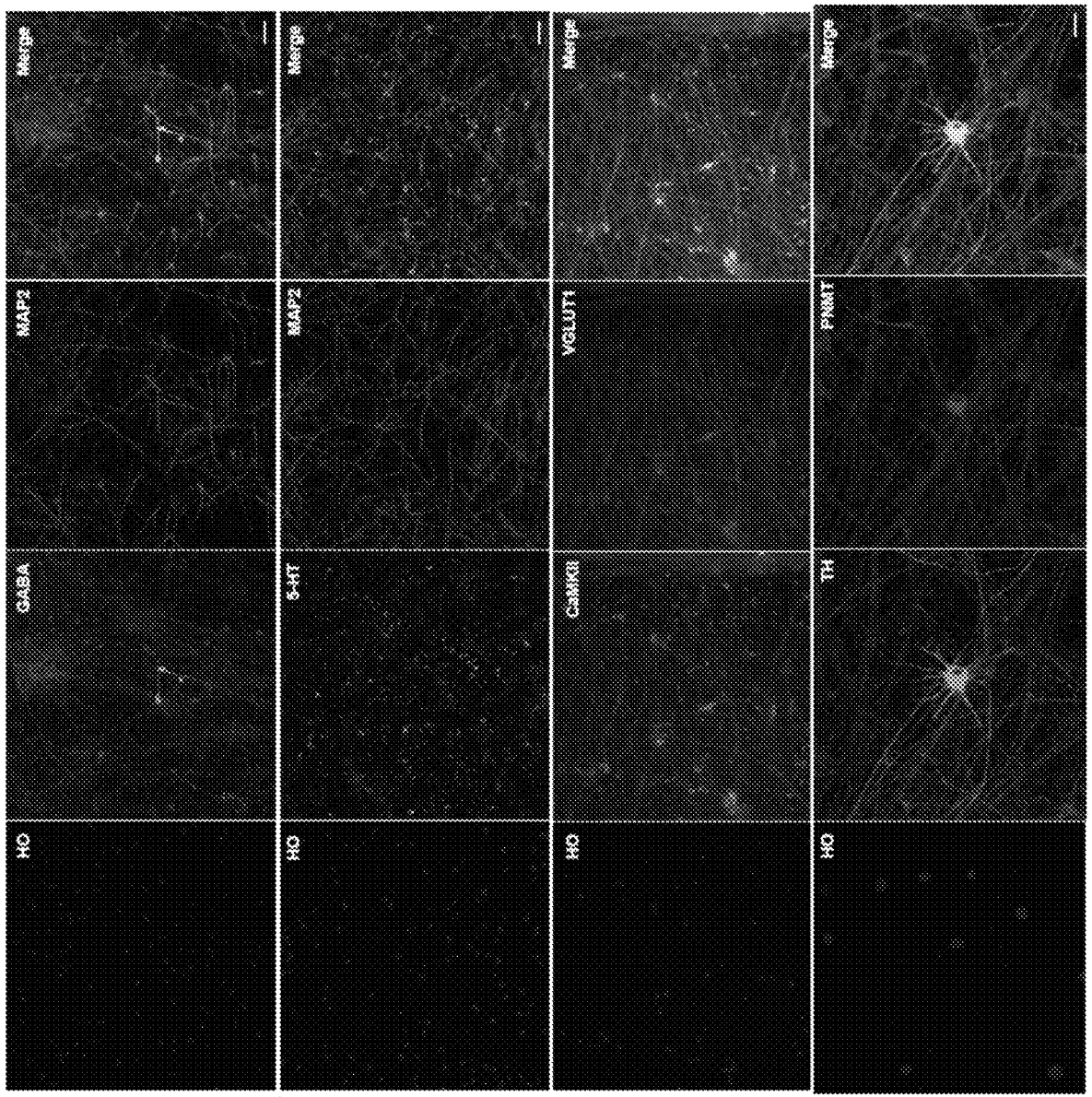
FIGS. 13A-13D.

To facilitate the study of NE neurons in culture, a TH-reporter line was developed to specifically label NE neurons. In this cell line, recombinase Cre was inserted into the C-terminal of the TH gene. The cell line also contained a DIO-mCherry element in the AAVS1 site of the genome, which is driven by a CAG promoter (FIGS. 11A, 12A & 12B). In embodiments where the cell expresses the TH gene, the Cre was also capable of being generated, resulting in expression of mCherry. Genome editing was confirmed by DNA sequencing and immunostaining. Results confirmed that mCherry can reliably indicate TH expression (FIG. 11B), and the brightness observed under regular fluorescent microscope allows for easy targeting of the labeled NE neurons (FIG. 11C). Whole-cell patch clamp recording was performed on neurons at 4-8 weeks post plating (6-10 weeks from hESCs). Results indicated that among 88 recorded cells, the mean cell capacitance (Cap) was 20.33±0.69 pF. Approximately 37.5% (33 out of 88) neurons displayed spontaneous action potential (sAP) production with an average firing rate at 0.75±0.17 Hz (FIG. 11D). Inward Na+ and outward K+ currents were observed in these cells by voltage steps from −70 mV to +70 mV (FIG. 11E). Surprisingly, the results revealed that approximately 40% of the NE neurons responded to $CO_2$ concentration change and increased the firing rate when the medium included 5% $CO_2$ (FIGS. 11F & 11G). In contrast, non-TH neurons in the same culture did not increase the firing rate when exposed to 5% $CO_2$ (FIG. 11N). Treatment with a cocktail containing antagonists for NMDA receptor (50 μM D-AP5), non-NMDA glutamate receptors (20 μM CNQX), GABA receptor (20 μM bicuculline), and glycine receptor (10 μM strychnine) to block the presynaptic inputs did not significantly change the firing frequency (FIGS. 11H and 11I), suggesting the autonomous pacemaker activity in the NE neurons. Accompanying with the sAP firing, large calcium oscillations in the NE neurons using the cell-permeable, fluorescent $Ca^{2+}$ indicator Fluo-4 AM were observed (FIG. 11J). Consistent with the pacemaker feature, the calcium oscillation frequency and amplitude were not altered by the cocktail blockers (FIG. 11K). Clonidine (1 mM) reduced the sAP firing rating significantly, which was reversed upon washing away clonidine (FIGS. 11L and 11M).

Engineering a Scalable Drug Screen Platform for NE Release

Norepinephrine released by NE neurons in the brain plays a vital role in sleep-awake cycle, focus, fight or flight reaction and stress response. Problems with norepinephrine levels are associated with depression, anxiety, Parkinson's Disease and Alzheimer's Disease. Low levels can cause depression, ADHD, low blood pressure and lack of attention/concentration. Patients with depression can be treated by a class of drug called serotonin-norepinephrine reuptake inhibitors (SNRIs), which raise the level of norepinephrine and serotonin in the brain. Here, a scalable drug screen platform for NE release was designed by combining hPSC derived NE neurons and newly developed NE sensor ($GRAB_{NE1m}$) (see Feng et al., 2019, Neuron, 102:745-761), which could specifically detect extracellular norepinephrine levels. As described by Feng et al. 2019, $GRAB_{NE1m}$ contains a glycine-to-threonine mutation at position C1 of circular permutated EGFP (enhanced GFP).

Figure 5B:
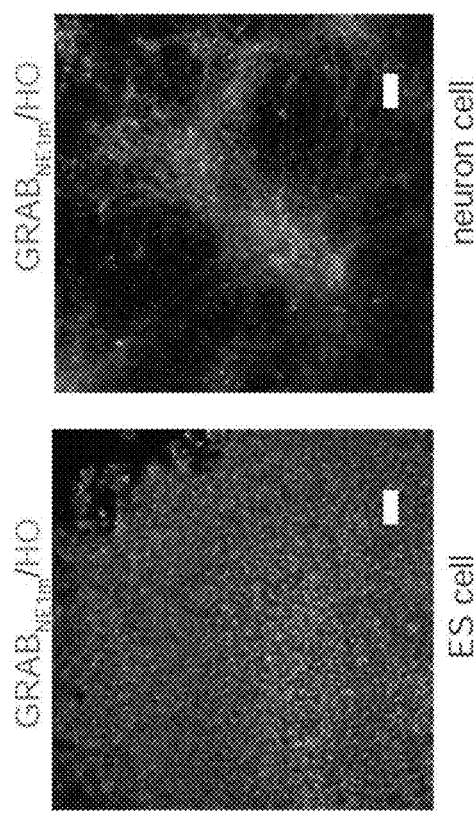
Figure 5A:
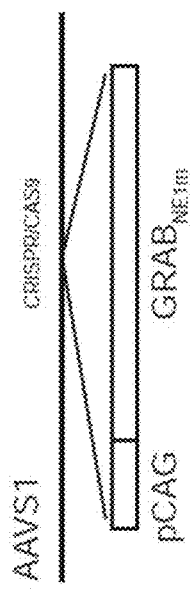
Figure 5C:
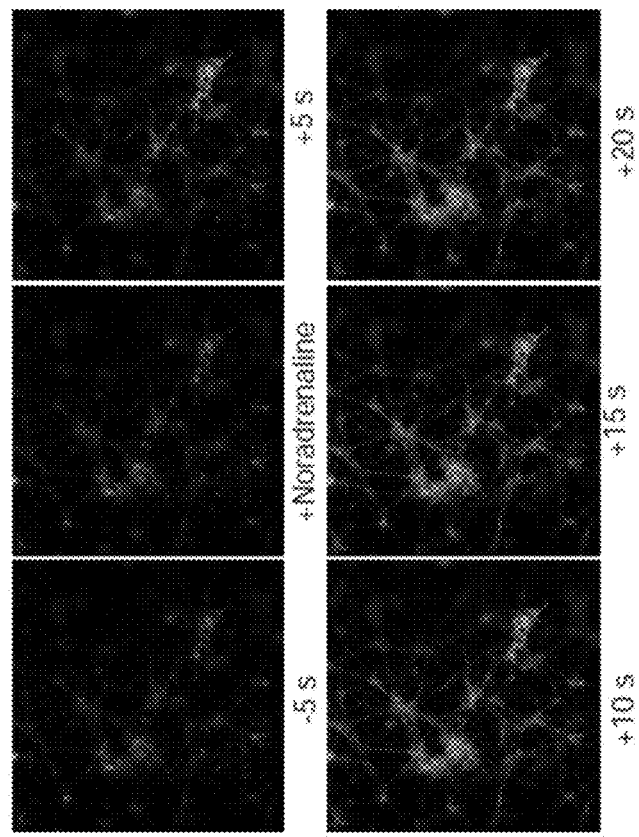
Figure 5F:
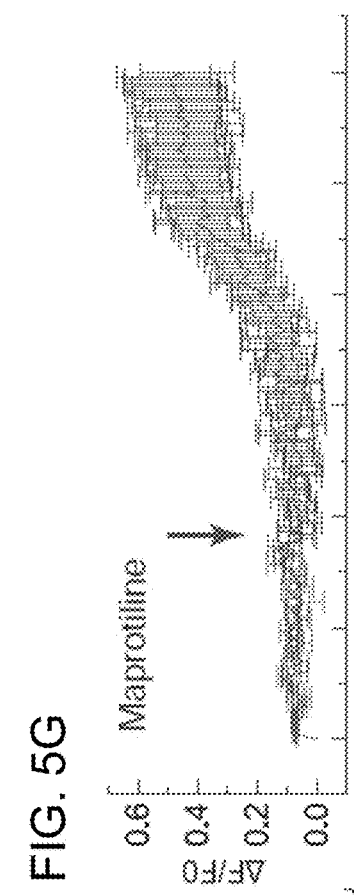
Figure 5G:
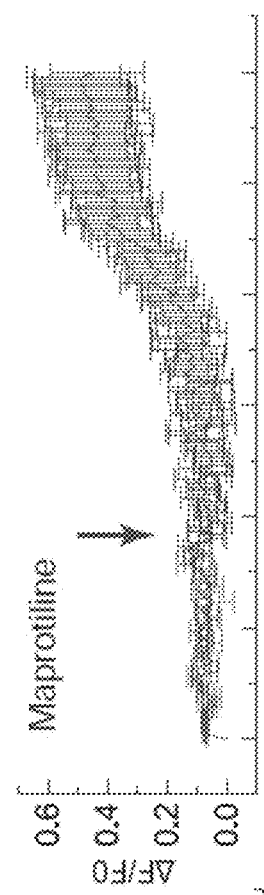
Figure 5H:
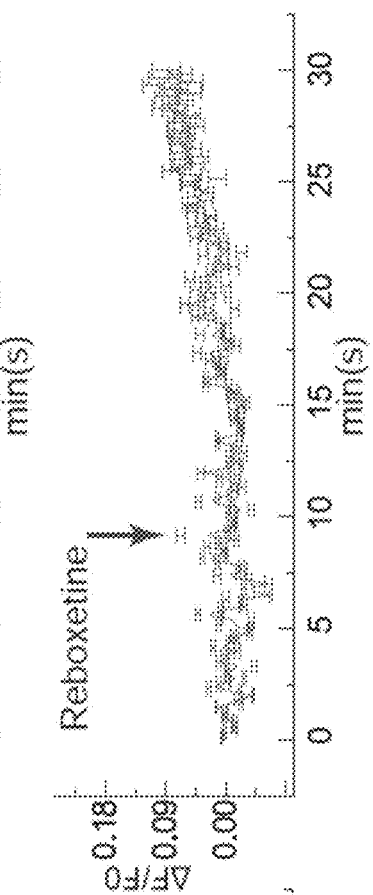
Figure 5I:
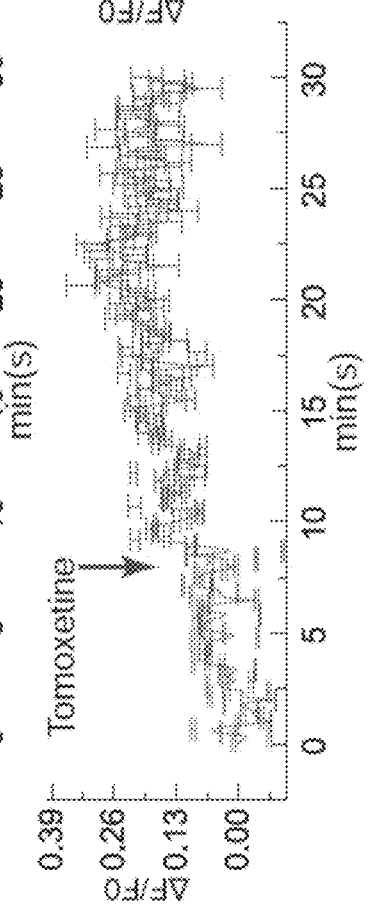
Figure 5J:
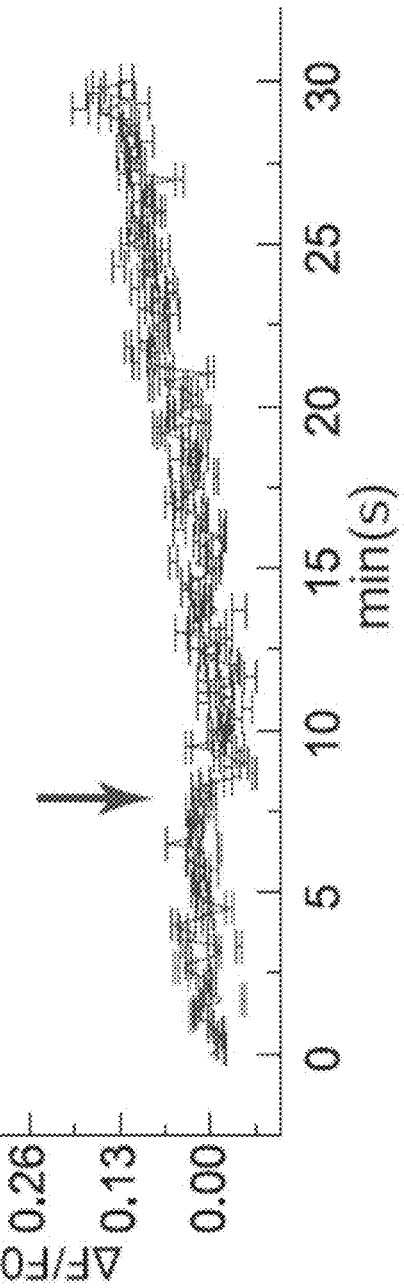
Figure 5K:
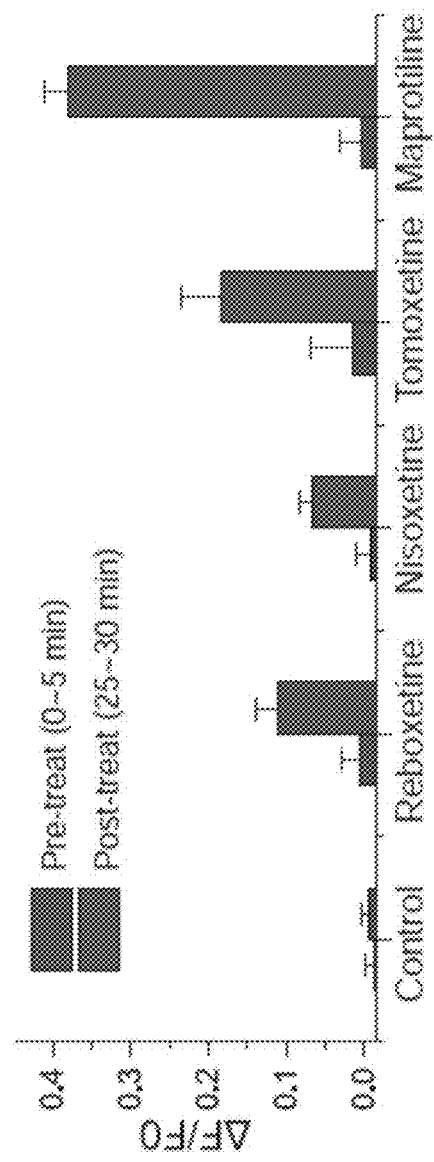
Figure 5L:
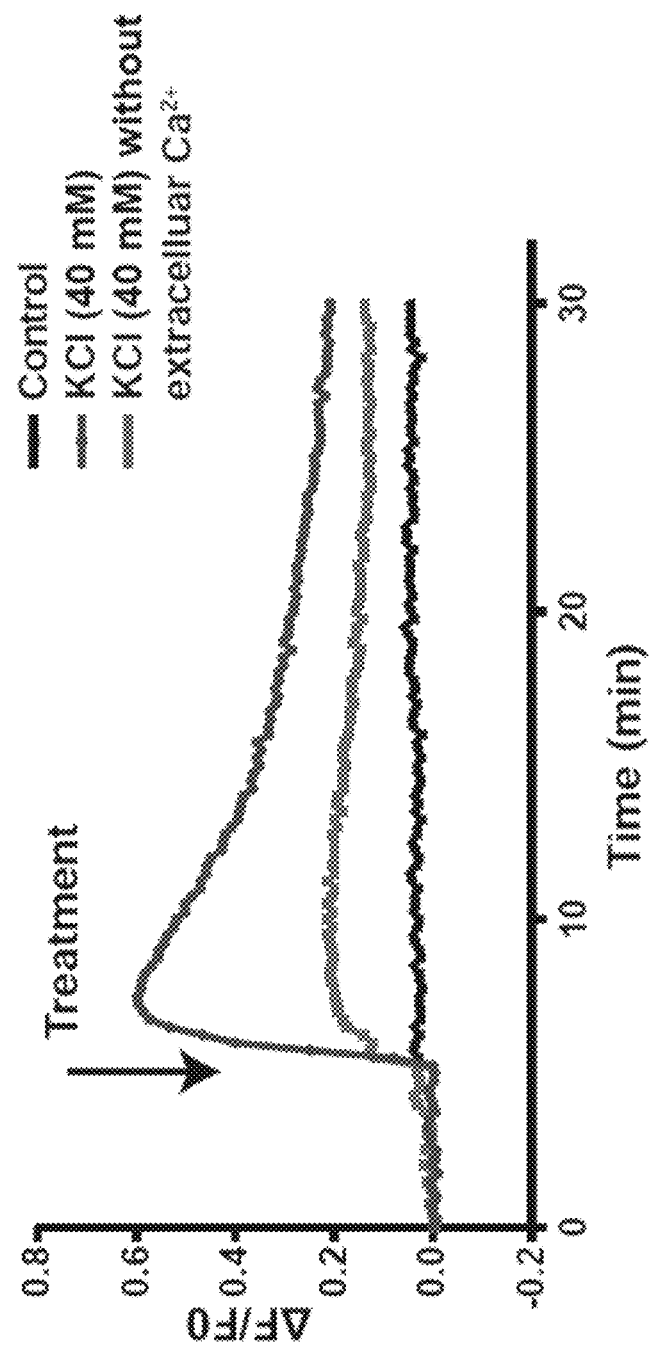
Figure 10A:
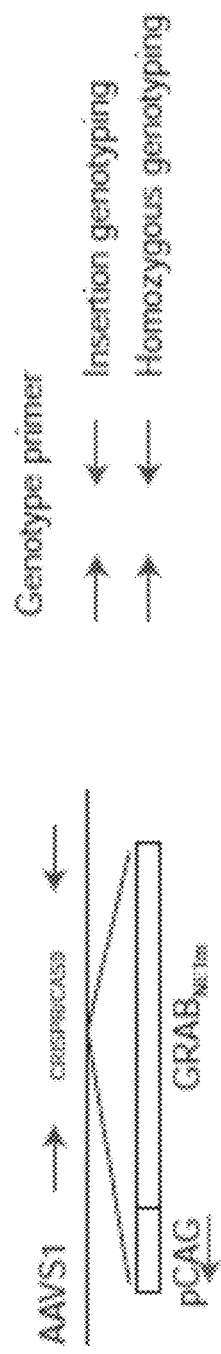
FIGS. 10A-10C.
Figure 10B:
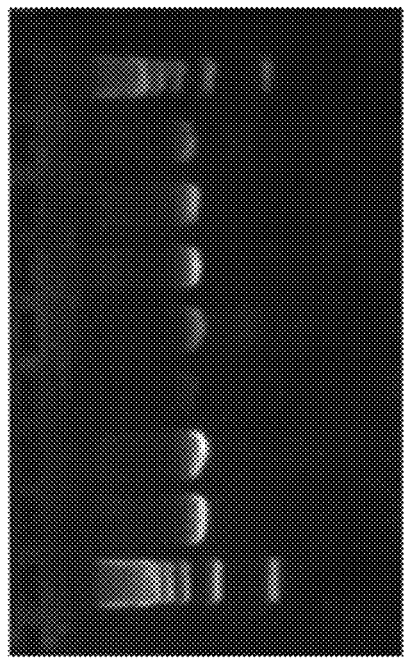
Figure 10C:
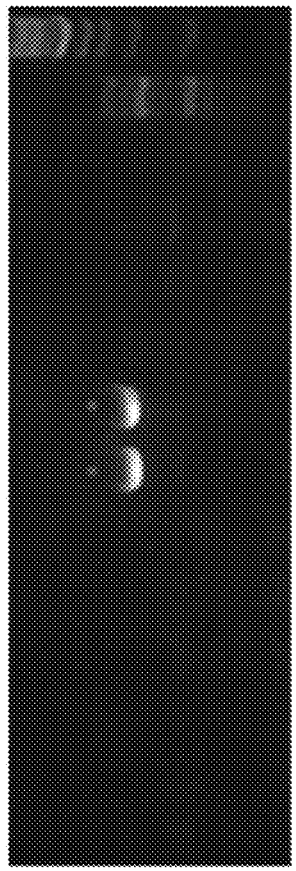

CRISPR/CAS9 was used to generate a cell line (H9) with $GRAB_{NE1m}$ sensor inserted at the AAVS1 site (FIG. 5A, FIG. 10). $GRAB_{NE1m}$ sensor can normally express in ES cells and ES-derived neurons (FIG. 5B). The intensity of $GRAB_{NE1m}$ sensor fluorescence increased after treatment of Norepinephrine (1 μM) (FIG. 5C). A dynamic change of extracellular norepinephrine level was observed during live image (FIG. 5D) and the intensity along treatment quantified (FIG. 5E). Next, this cell line was used to check if it is suitable for drug screen. Four norepinephrine reuptake inhibitors (NRIs) (Tomoxetine, Maprotiline, Reboxetine and Nisoxetine) were used to treat $GRAB_{NE1m}$ sensor-expressing NE neurons and monitor the fluorescent intensity. All drugs were observed to increase $GRAB_{NE1m}$ sensor intensity, indicating an increase of extracellular norepinephrine (FIGS. 5F-5K). Importantly, the fluorescent intensity changed in response to KCl (40 mM), which was largely attenuated by removing the extracellular calcium (FIG. 5L), suggesting that the $GRAB_{NE1m}$ senses neuronal activity-dependent NE release/uptake. This drug screen system was thus capable of finding novel drugs that increase norepinephrine release from NE neurons, thereby providing a scalable drug screen platform for NE related diseases.

The results set forth herein demonstrated an efficient method to derive locus coeruleus (LC) NE neurons from human pluripotent stem cells. A novel and regional specific role of Activin A was identified in NE fate specification. hPSCs-derived NE neurons can produce norepinephrine and were responsive to norepinephrine reuptake inhibitor (NRI) treatment. Engineering an ES cell line expressing norepinephrine sensor ($GRAB_{NE1m}$) provided a scalable drug screen platform for NE-related diseases.

Dysregulation of NE system has been linked to Alzheimer's disease (AD), Parkinson's disease (PD), Rett syndrome, congenital central hypoventilation syndrome (CCHS), sleep disorders, ADHD, anxiety and depression. These data demonstrate that in vitro-derived human NE neurons can be used for cell therapy and for drug discovery to treat such neurological disorders. For instance, PD is characterized by its motor symptoms including bradykinesia, rigidity, and tremor at rest. In addition to motor deficits, PD has non-motor symptoms such as autonomic dysfunction, sensory and sleep difficulties, cognitive, and neurobehavioral problems (dementia and depression). However, depletion of dopamine (DA) alone was not sufficient to elicit both the motor and non-motor deficits of PD in animal models. In PD, significant cell death in LC coincides with DA neuron loss in the substantia nigra. Forno, 1996, *J Neuropathol Exp Neurol*, 55:259-272. LC NE neurons have been shown to be protective for DA neurons and are involved in the pathophysiology of PD. Gesi et al., 2000, *Neurosci Biobehav Rev*, 24:655-668; Delaville et al., 2011, *Front Syst Neurosci*, 5:31, doi:10.3389/fnsys.2011.00031. hPSC-derived DA neurons have been used to treat PD in non-human primates. Kikuchi et al., 2017, *Nature*, 548:592-596. However, work to date has focused on the motor function recovery instead of non-motor symptoms. Considering the function of NE neuron in autonomic behavior, sleep, cognition and depression, it would be interesting to study the therapeutic effects of NE neurons in PD models.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A method of generating human norepinephrine (NE) neuron progenitor cells, the method comprising
   (a) culturing in vitro human neuroepithelial cells having hindbrain rhombomere 1 (R1) regional identity for about 2 to about 4 days in a first culture medium comprising a first concentration of Activin A; and
   (b) culturing the cultured cells of (a) for about 3 to about 4 days in a second culture medium comprising a second concentration of Activin A, wherein the second concentration is B greater than the first concentration, to obtain a cell population comprising greater than 40% norepinephrine (NE) neuron progenitor cells expressing MASH1+/PHOX2B+/PHOX2A+ and negative for Otx2 expression
   wherein the human neuroepithelial cells are obtained from human pluripotent stem cells (hPSCs) in vitro,
   wherein the first concentration of Activin A is a concentration of about 10 ng/ml to about 50 ng/ml,
   wherein the second concentration of Activin A is a concentration of about 100 ng/ml to about 250 ng/ml.
2. The method of claim 1, wherein the first culture medium further comprises DMEM/F-12, N2 supplement, and non-essential amino acid (NEAA) supplement.
3. The method of claim 1, wherein the second culture medium further comprises DMEM/F-12, N2 supplement, B27 supplement, and NEAA supplement.
4. The method of claim 1, wherein each of the first culture medium and the second culture medium further comprises an inhibitor of bone morphogenic protein (BMP) signaling.
5. The method of claim 4, wherein the inhibitor of BMP signaling is selected from dorsomorphin homolog 1 (DMH1) and LDN-193189.
6. The method of claim 1, wherein the human neuroepithelial cells having hindbrain R1 regional identity are

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
ggggccacta gggacaggat                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
taggtgcacg gcgtccctga                    20 obtained according to a method comprising: culturing human pluripotent stem cells (hPSCs) in a culture medium comprising an inhibitor of BMP signaling, an inhibitor of TGFβ signaling, and a Wnt agonist for about 6 days, whereby a population of neuroepithelial cells having hindbrain R1 regional identity are obtained.

7. The method of claim 6, wherein the inhibitor of BMP signaling is DMHI, the inhibitor of TGFβ signaling is SB431542, and the WNT agonist is CHIR99021.

8. The method of claim 6, wherein the pluripotent stem cells are human embryonic stem cells or human induced pluripotent stem cells.

* * * * *